US009376610B2

(12) United States Patent
Hendrickson et al.

(10) Patent No.: US 9,376,610 B2
(45) Date of Patent: Jun. 28, 2016

(54) **METHODS, STRAINS, AND COMPOSITIONS USEFUL FOR MICROBIALLY ENHANCED OIL RECOVERY: *ARCOBACTER* CLADE 1**

(75) Inventors: Edwin R. Hendrickson, Hockessin, DE (US); Scott Christopher Jackson, Wilmington, DE (US); Abigail K Luckring, West Chester, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 792 days.

(21) Appl. No.: 13/280,972

(22) Filed: Oct. 25, 2011

(65) Prior Publication Data

US 2012/0277127 A1 Nov. 1, 2012

Related U.S. Application Data

(60) Provisional application No. 61/408,739, filed on Nov. 1, 2010.

(51) Int. Cl.

*C09K 8/58* (2006.01)
*C09K 8/582* (2006.01)
*C12N 1/20* (2006.01)
*C12R 1/01* (2006.01)

(52) U.S. Cl.

CPC . *C09K 8/582* (2013.01); *C12N 1/20* (2013.01); *C12R 1/01* (2013.01)

(58) Field of Classification Search

CPC .... C09K 8/805; C09K 2208/00; C09K 5/048; C09K 5/10; C09K 8/035; C09K 8/42; C09K 8/514; C09K 8/54; C09K 8/584; C09K 8/594; C09K 8/74; E21B 33/13; E21B 43/26; E21B 43/2406; E21B 10/32; E21B 10/567; E21B 33/03; E21B 43/12; E21B 43/25; E21B 10/26; E21B 10/46; E21B 10/55; E21B 10/5673; E21B 10/5735; E21B 19/22; E21B 33/068; E21B 2023/008; E21B 2034/005; E21B 2034/007; E21B 21/015; E21B 21/063; E21B 21/08; E21B 23/01; E21B 23/04; E21B 25/16; E21B 33/043; E21B 33/10; E21B 33/12; E21B 33/126; E21B 33/127

See application file for complete search history.

(56) References Cited

U.S. PATENT DOCUMENTS 4,558,739 A 12/1985 McInerney et al.
4,717,653 A 1/1988 Webster
4,800,959 A 1/1989 Costerton et al.
5,083,611 A 1/1992 Clark et al.
5,163,510 A 11/1992 Sunde
5,174,378 A 12/1992 Costerton et al.
7,708,065 B2 5/2010 Hendrickson et al.
7,776,795 B2 8/2010 Keeler et al.
2009/0082227 A1* 3/2009 Hnatow .................. C02F 3/344 507/201
2010/0044031 A1* 2/2010 Fallon .................... C09K 8/582 166/246
2010/0047793 A1* 2/2010 Toledo .................. C09K 8/582 435/6.12
2011/0030956 A1 2/2011 Choban et al.
2011/0277991 A1* 11/2011 Toledo .................. C09K 8/582 166/246
2012/0241148 A1* 9/2012 Alsop .................... E21B 43/20 166/246
2013/0079259 A1* 3/2013 Perry .................... C09K 8/584 507/201
2013/0095562 A1* 4/2013 Perry ....................... C10G 1/04 435/281

OTHER PUBLICATIONS

N. Fernandez, E. E. Diaz, R. Amils and J. L. Sanz, Analysis of microbial community during biofilm development in an anaerobic wastewater treatment reactor, Microb Ecol, 2008, 56, 121-132.*

Ross et al., "Clogging of a limestone fracture by stimulating groundwater microbes", Water Research, vol. 35, No. 8, 2001, pp. 2029-2037 (Abstract).

Bennasar et al., "16S rRNA gene sequence analysis relative to genomovars of *Pseudomonas stutzeri* and proposal of *Pseudomonas balearica* sp. nov.", Int. J. of Syst. Bacteriol., vol. 46, 1996, pp. 200-205.

Fredrickson et al., "Towards Environmental Systems Biology Shewanella", Nature Reviews Microbiology, vol. 6, No. 8, 2008, pp. 592-603.

Hau et al., "Ecology and Biotechnology of the Genus *Shewanella*", Annual Review of Microbiology, vol. 61, 2007, pp. 237-258.

Moreno-Vivian et al., "Prokaryotic nitrate reduction: molecular properties and functional distinction among bacterial nitrate reductases" J. Bacteriol., vol. 181, 1999, pp. 6573-6584.

Grabowski et al., "Microbial diversity in production waters of a low-temperature biodegraded oil reservoir", FEMS Microbiology Ecology, vol. 3, 2005, pp. 427-443.

Bruce, "Automated system rapidly identifies and characterizes microorganisms in food", Food Technology, vol. 50, 1996, pp. 77-81.

Sethi, "Fully automated microbial characterization and identification for industrial microbiologists", Am. Lab. vol. 5, 1997, pp. 31-35.

Brosius et al., "Gene Organization and primary structure of a ribosomal RNA operon from *Escherichia coli*", Journal of Molecular Biology, vol. 148, No. 2, 1981, pp. 107-127.

Woese, "Bacterial Evolution", Microbial Rev., vol. 51, 1987, pp. 221-271.

Donachie et al., "*Arcobacter halophilus* sp. nov., the first obligate halophile in the genus *Arcobacter*", Int. J. Syst. Evol. Microbiol., vol. 55, 2005, 1271-1277.

Kim et al., "*Arcobacter marinus* sp. nov.", Int. J. Syst. Evol. Microbiol., vol. 60, 2010, pp. 531-536.

Teske et al., "Molecular identification of bacteria from a coculture by denaturing gradient gel electrophoresis of 16S ribosomal DNA fragments as a tool for isolation in pure cultures", Appl. Environ. Microbiol., vol. 62, 1996, 4210-4215.

* cited by examiner

*Primary Examiner* — Susannah Chung
*Assistant Examiner* — Kumar R Bhushan

(57) ABSTRACT

Methods, microorganisms, and compositions are provided wherein oil reservoirs are inoculated with microorganisms belonging to *Arcobacter* clade 1 and medium including an electron acceptor. The *Arcobacter* strains grow in the oil reservoir to form plugging biofilms that reduce permeability in areas of subterranean formations thereby increasing sweep efficiency, and thereby enhancing oil recovery.

6 Claims, 15 Drawing Sheets

```
                                                                                  |--------Variable region 1------------------>
    Insertion (><) or Deletion (<>)                  10        20        30        40        50        60        70        80
                                                  8 --+---------+---------+---------+---------+---------+---------+--------< >+-------
Arcobacter sp clade 1 Consensus                      AGAGTTTGATCCTGGCTCAGAGTGAACGCTGGCGGCGTGCTTAACACATGCAAGTCGAACGAGAACGGGAT - TAGCTTGC
Arcobacter sp clade 1 Degenerate Consensus           AGTCGAGCGGYMTGGCTCAGAGTGAACGCTGGCGGCGTGCTTAACACATGCAAGTCGAACGAGAACGGRWT[A]TAGCTTGC
97AE3-12                                             AGAGTTTGATTATGGCTCAGAGTGAACGCTGGCGGCGTGCTTAACACATGCAAGTCGAACGAGAACGGGAT - TAGCTTGC
Arcobacter sp clade 2 Degenerate Consensus           AGTCGAGCGGYMTGGCTCAGAGTGAACGCTGGCGGCGTGCTTAACACATGCAAGTCGAACGAGAACGGRTT A WAGCTTGC
Arcobacter sp clade 3 Degenerate Consensus           AGTCGAGCGGYMTGGCTCAGAGTGAACGCTGGCGGCGTGCTTAACACATGCAAGTCGAACGAGAACGGATT A TAGCTTGC

                                                <----------------------------|         |------------------------Variable region 2------->
Insertion(><) or Deletion(<>)                        90        100       110       120       130          140       150       160
                                               88 --> <+---------> <+---------+---------+---------+--> <--------+---------+---------+-------
Arcobacter sp clade 1 Consensus                 TA - ATCTGTCAGC T AAGTGGCGCACGGGTGAGTAATATATAGGTAAC G TGCCTTCAAGAGGGGGATAACAGATGGAAACGTCT
Arcobacter sp clade 1 Degenerate Consensus      TA[T]ATCTGTCAGC T AAGTGGCGCACGGGTGAGTAATRTATAGGTAAC R.TGCCYYYAAGAGGGGGATAACAGWTGGAAACGWCT
97AE3-12                                        TA - ATCTGTCAGC T AAGTGGCGCACGGGTGAGTAATATATAGGTAAC G TGCCTTCAAGAGGGGGATAACAGATGGAAACGTCT
Arcobacter sp clade 2 Degenerate Consensus      TW W WWYTGTCAGC T AAGTGGCGCACGGGTGAGTAATRTATAGGTAAC M TGCCCTMDAGARRRGRATAACAGWTGGAAACGWCT
Arcobacter sp clade 3 Degenerate Consensus      TA T ARTTGTCAGC T AAGTGGCGCACGGGTGAGTAATRTATAGGTAAC T TGCCTCTTACTAAGGGATAACARWTGGAAACGWYT
                                                <---------------------------------------------------------------------------------->
Insertion(><) or Deletion(<>)                    170       180       190       200       210            220       230       240
                                              168 --+---------+---------+---------+---------+>(+1)<--------+---------+---------+-------
Arcobacter sp clade 1 Consensus                 GCTAAAACCCCATATGCCTTTAATACGAAAGTATGCAAGGGAAA - TATTTATAGCTTGAAGATCGGCCTGTACAGTATCAG
Arcobacter sp clade 1 Degenerate Consensus      GCTAADRYCYYATATGCCTTTAATRCDAAAGTATGMAAGGGAAA(C)KYTTWAKWGCTTRRRGATYGGCCTGTAYWGTATCAG
97AE3-12                                        GCTAAAACCCCATATGCCTTTAATGCGAAAGTATGCAAGGGAAA - TATTTATAGCTTGAAGATCGGCCTGTACAGTATCAG
Arcobacter sp clade 2 Degenerate Consensus      GCTAADRYCYYATATGCCTTTAAKACHYAWGTYTGCAAGGGAAA[W]CATTTATGGCTCTAGGATKGGYCTGTAYRGTATCAG
Arcobacter sp clade 3 Degenerate Consensus      GCTAACACCCCATAYTCCWYYYYAWCHWAAGWTRRWAAGGGAAA - GATTTATTGGTAAGAGATTAGCCTGTATTGTATCAG

                                                <----------------------------------------------------|
Insertion(><) or Deletion(<>)                    250       260       270       280       290       300       310       320
                                              248 --+---------+---------+---------+---------+---------+---------+---------+-------
Arcobacter sp clade 1 Consensus                 ATAGTTGGTGAGGTAATAGCTCACCAAGTCAATGACGCTTAACTGGTTTGAGAGGATGATCAGTCACACTGGAACTGAGA
Arcobacter sp clade 1 Degenerate Consensus      MTAGTTGGTGRGGTAAKAGCYYACCAAGDCAATGACGCWTAACTGGTTTGAGAGGATGATCAGTCACACTGGAACTGAGA
97AE3-12                                        ATAGTTGGTGAGGTAATAGCTCACCAAGTCAATGACGCTTAACTGGTTTGAGAGGATGATCAGTCACACTGGAACTGAGA
Arcobacter sp clade 2 Degenerate Consensus      MTMGTTGGTGAGGTAATGGCTCACCAAGRCAATGACRCYTAACTGGTTTGAGAGGATGATCAGTCACACTGGAACTGAGA
Arcobacter sp clade 3 Degenerate Consensus      TTAGTTGGTGGGGTAATGGCCTACCAAGACDATGACGCATAACTGGTTTGAGAGGATGATCAGTCACACTGGAACTGAGA
```

*FIG. 3A*

| FIG. 3B | |
|---|---|
| FIG. 3BA | FIG. 3BB |

```
Insertion(><) or Deletion(<>)              330       340       350       360       370       380       390       400
                                       328 --+---------+---------+---------+---------+---------+---------+---------+-------
Arcobacter sp clade 1 Consensus            CACGGTCCAGACTCCTACGGGAGGCAGCAGTGGGGAATATTGCACAATGGGGGAAACCCTGATGCAGCAACGCCGCGTGG
Arcobacter sp clade 1 Degenerate Consensus CACGGTCCAGACTCCTACGGGAGGCAGCAGTGGGGAATATTGCACAATGGGGGRAACCCTGATGCAGCAACGCCGCGTGG
97AE3-12                                   CACGGTCCAGACTCCTACGGGAGGCAGCAGTGGGGAATATTGCACAATGGGGGAAACCCTGATGCAGCAACGCCGCGTGG
Arcobacter sp clade 2 Degenerate Consensus CACGGTCCAGACTCCTACGGGAGGCAGCAGTGGGGAATATTGCACAATGGACGAAAGTCTGATGCAGCAACGCCGCGTGG
Arcobacter sp clade 3 Degenerate Consensus CACGGTCCAGACTCCTACGGGAGGCAGCAGTGGGGAATATTGCACAATGGACGAAAGTCTGATGCAGCAACGCCGCGTGG

                                           <----------------------------------------------------------------------|
Insertion(><) or Deletion(<>)              410       420       430       440       450(-25)480       490       500       510
                                       408 --+---------+---------+---------+---------+-< >---+---------+---------+---------+
Arcobacter sp clade 1 Consensus            AGGATGACACATTTCGGTGCGTAAACTCCTTTTATATAAGAAGA - TAATGACGGTATTATATGAATAAGCACCGGCTAA
Arcobacter sp clade 1 Degenerate Consensus AGGATGACACATTTCGGTGCGTAAACTCCTTTTATATARGAAGA - WAATGACGGTAYTATATGAATAAGCRCCGGCTAA
97AE-12                                   AGGATGACACATTTCGGTGCGTAAACTCCTTTTATATAAGAAGA - TAATGACGGTATTATATGAATAAGCACCGGCTAA
Arcobacter sp clade 2 Degenerate Consensus AGGATGACACATTTCGGTGCGTAAACTCCTTTTATATAGGAAGA - TAATGACGGTAYYATATGAATAAGCACCGGCTAA
Arcobacter sp clade 3 Degenerate Consensus AGGATGACACATTTCGGTGCGTAAACTCCTTTTATATAAGAAGA - TAATGACGGTATTATATGAATAAGCACCGGCTAA

                                                                                                          |--------------->
Insertion(><) or Deletion(<>)                       520       530       540       550       560       570       580       590
                                       511 ---------+---------+---------+---------+---------+---------+---------+---------+
Arcobacter sp clade 1 Consensus            CTCCGTGCCAGCAGCCGCGGTAATACGGAGGGTGCAAGCGTTACTCGGAATCACTGGGCGTAAAGAGCGTGTAGGCGGAT
Arcobacter sp clade 1 Degenerate Consensus CTCCGTGCCAGCAGCCGCGGTAATACGGAGGGYGCAAGCGTTACTCGGAATCACTGGGCGTAAAGAGCGTGTAGGCGGAT
97AE3-12                                   CTCCGTGCCAGCAGCCGCGGTAATACGGAGGGTGCAAGCGTTACTCGGAATCACTGGGCGTAAAGAGCGTGTAGGCGGAT
Arcobacter sp clade 2 Degenerate Consensus CTCCGTGCCAGCAGCCGCGGTAATACGGAGGGTGCAAGCGTTACTCGGAATCACTGGGCGTAAAGAGCRTGTAGGCGGGT
Arcobacter sp clade 3 Degenerate Consensus CTCCGTGCCAGCAGCCGCGGTAATACGGRGGGTGCAAGCGTTACTCGGAATCACTGGGCGTAAAGAGCRTGTAGGCGGAT
```

FIG. 3BA

```
------------------------------------------------------------------------------------------------------------------------------
                                              <-------------------------------------------------------------------------------->
Insertion(><) or Deletion(<>)                          600       610       620       630       640       650       660       670
                                          591 ---------+---------+---------+---------+---------+---------+---------+---------+
Arcobacter sp clade 1 Consensus               AGATAAGTCAGAAGTGAAATCCAATAGCTTAACTATTGAACTGCTTTTGAAACTGTCTATCTAGAGTATGGGAGAGGTAG
Arcobacter sp clade 1 Degenerate Consensus    MRATAAGTYAGRAGTGAAATCCWATRGCTYAACYATWGAACTGCTTYTRAAACTGTYWATCTAGAGTATGGGAGAGGTAG
97AE3-12                                      AGATAAGTCAGAAGTGAAATCCAATAGCTTAACTATTGAACTGCTTTTGAAACTGTCTATCTAGAGTATGGGAGAGGTAG
Arcobacter sp clade 2 Degenerate Consensus    AWWTAAGTYDGAAGTGAAATCCWATRGCTYAACYATWGAACTGCTTCCAAAACTGKTAACCTAGAATRTGGGAGAGGTAG
Arcobacter sp clade 3 Degenerate Consensus    TRATAAGTTTGAAGTGAAATCCTATAGCTTAACTATAGAACTGCTTTGAAAACTGTTAACCTAGAATGTGGGAGAGGTAG

                                              <--------------------------------Variable region 4------------------------------|
Insertion(><) or Deletion(<>)                          680       690       700       710       720       730       740       750
                                          671 ---------+---------+---------+---------+---------+---------+---------+---------+
Arcobacter sp clade 1 Consensus               ATGGAATTTCTGGTGTAGGGGTAAAATCCGTAGAGATCAGAAGGAATACCGATTGCGAAGGCGATCTACTGGAACATAAC
Arcobacter sp clade 1 Degenerate Consensus    ATGGAATTTCTGGTGTAGGGGTAAAATCCGTAGAGATCAGAAGGAATACCGATTGCGAAGGCGATCTACTGGAACATAAC
97AE3-12                                      ATGGAATTTCTGGTGTAGGGGTAAAATCCGTAGAGATCAGAAGGAATACCGATTGCGAAGGCGATCTACTGGAACATAAC
Arcobacter sp clade 2 Degenerate Consensus    ATGGAATTTCTGGTGTAGGGGTAAAATCCGTAGAKATCAGAAGGAATACCGATTGCGAAGGCGATCTACTGGAACAYWAT
Arcobacter sp clade 3 Degenerate Consensus    ATGGAATTTCTGGTGTAGGGGTAAAATCCGTAGAGATCAGAAGGAATACCGATTGCGAAGGCGATCTACTGGAACAHTAT
```

*FIG. 3BB*

| FIG. 3C | |
|---|---|
| FIG. 3CA | FIG. 3CB |

```
Insertion(><) or Deletion(<>)                         760       770       780       790       800       810       820       830
                                               751 ---------+---------+---------+---------+---------+---------+---------+---------+
Arcobacter sp clade 1 Consensus                    TGACGCTGAGACGCGAAAGCGTGGGGAGCAAACAGGATTAGATACCCTGGTAGTCCACGCCCTAAACGATGTACACTAGT
Arcobacter sp clade 1 Degenerate Consensus         TGACGCTGAGACGCGAAAGCGTGGGGAGCAAACAGGATTAGATACCCTGGTAGTCCACGCCCTAAACGATGTACACTAGT
97AE3-12                                           TGACGCTGAGACGCGAAAGCGTGGGGAGCAAACAGGATTAGATACCCTGGTAGTCCACGCCCTAAACGATGTACACTAGT
Arcobacter sp clade 2 Degenerate Consensus         TGACGCTGAGAYGCGAAAGCGTGGGGAGCAAACAGGATTAGATACCCTGGTAGTCCACGCCCTAAACGATGYACACTAGT
Arcobacter sp clade 3 Degenerate Consensus         TGACGCTGAGAYGCGAAAGCGTGGGGAGCAAACAGGATTAGATACCCTGGTAGTCCACGCCCTAAACGATGTACACTAGT

                                                   <----------Variable region 5---------------------|
Insertion(><) or Deletion(<>)                         840       850       860       870       880       890       900       910
                                               831 ---------+---------+---------+---------+---------+---------+---------+---------+
Arcobacter sp clade 1 Consensus                    TGTTGCTATGCTCGACATAGCAGTAATGCAGTTAACACATTAAGTGTACCGCCTGGGGAGTACGGTCGCAAGATTAAAAC
Arcobacter sp clade 1 Degenerate Consensus         TGTTGCYATRCTCGACATDGCAGTAATGCAGTTAACACATTAAGTGTACCGCCTGGGGAGTACGGTCGCAAGRTTAAAAC
97AE3-12                                           TGTTGCTATGCTCGACATAGCAGTAATGCAGTTAACACATTAAGTGTACCGCCTGGGGAGTACGGTCGCAAGATTAAAAC
Arcobacter sp clade 2 Degenerate Consensus         TGTTGTGAGGCTAGACCTTGCAGTAATGCAGTTAACACATTAAGTGTRCCGCCTGGGGAGTACGGTCGCAAGATTAAAAC
Arcobacter sp clade 3 Degenerate Consensus         TGTTGTGAGRCTYGAYCTTGCAGTAATGCAGTTAACACATTAAGTGTACCGCCTGGGGAGTACGGTCGCAAGATTAAAAC

Insertion(><) or Deletion(<>)                         920       930       940       950       960       970       980       990
                                               911 ---------+---------+---------+---------+---------+---------+---------+---------+
Arcobacter sp clade 1 Consensus                    TCAAAGGAATAGACGGGGACCCGCACAAGCGGTGGAGCATGTGGTTTAATTCGACGATACGCGAAGAACCTTACCTGGTC
Arcobacter sp clade 1 Degenerate Consensus         TCAAAGGAATAGACGGGGACCCGCACAAGCGGTGGAGYATGTGGTTTAATTCGACGATACGCGAAGAACCTTACCTGGTC
97AE3-12                                           TCAAAGGAATAGACGGGGACCCGCACAAGCGGTGGAGCATGTGGTTTAATTCGACGATACGCGAAGAACCTTACCTGGTC
Arcobacter sp clade 2 Degenerate Consensus         TCAAAGGAATAGACGGGGACCCGCACAAGCGGTGGAGCATGTGGTTTAATTCGACGATACRCGAAGAACCTTACCTGGWC
Arcobacter sp clade 3 Degenerate Consensus         TCAAAGGAATAGACGGGGACCCGCACAAGCGGTGGAGCATGTGGTTTAATTCGACGATACACGAAGAACCTTACCTGGAC
```

FIG. 3CA

```
                                            |--------------------- Variable region 6------------------------|
Insertion(><) or Deletion(<>)                       1000      1010      1020     (+4)1030      1040      1050      1060
                                        991 ---------+---------+---------+------->   <+---------+---------+---------+------
Arcobacter sp clade 1 Consensus              TTGACATAGTAAGAACCATTTAGAGATAGATGGGTGTCTGCTTGCAGAAACTTATATACAGGTGCTGCACGGCTGTCGTC
Arcobacter sp clade 1 Degenerate Consensus   TTGACATAGWAAGAAYHMTYYAGAGATAGATGGGTGYYWGCTTGCWRRARCTTWYATACAGGTGCTGCACGGCTGTCGTC
97AE3-12                                     TTGACATAGTAAGAACCATTTAGAGATAGATGGGTGTCTGCTTGCAGAAACTTATATACAGGTGCTGCACGGCTGTCGTC
Arcobacter sp clade 2 Degenerate Consensus   TTGACATAGWAAGAACNTWHYAGAGATAGATGGGTGYYWGCTTGCWRRARCTWWYATACAGGTGCTGCACGGCTGTCGTC
Arcobacter sp clade 3 Degenerate Consensus   TTGACATAGTAAGAAYKWTYWAGAGATAGATGGGTGTCTGCTTGCAGAAACTTRYATACAGGTGCTGCACGGCTGTCGTC

                                                                                 |------------- Variable region 7--------->
Insertion(><) or Deletion(<>)                  1070      1080      1090      1100      1110      1120      1130      1140
                                       1067 ---+---------+---------+---------+---------+---------+---------+---------+------
Arcobacter sp clade 1 Consensus              AGCTCGTGTCGTGAGATGTTGGGTTAAGTCCCGCAACGAGCGCAACCCTCGTCATTAGTTGCTAACACTTCGGGTGAGAA
Arcobacter sp clade 1 Degenerate Consensus   AGCTCGTGTCGTGAGATGTTGGGTTAAGTCCCGCAACGAGCGCAACCCTCGTCRTTAGTTGCTAASACTWCGGSTGAGAA
97AE3-12                                     AGCTCGTGTCGTGAGATGTTGGGTTAAGTCCCGCAACGAGCGCAACCCTCGTCATTAGTTGCTAACACTTCGGGTGAGAA
Arcobacter sp clade 2 Degenerate Consensus   AGCTCGTGTCGTGAGATGTTGGGTTAAGTCCCGCAACGAGCGCAACCCTCGTSDTTAGTTGCTAAGACTTCGGCTGAGAA
Arcobacter sp clade 3 Degenerate Consensus   AGCTCGTGTCGTGAGATGTTGGGTTAAGTCCCGCAACGAGCGCAACCCTCGTCBTTAGTTGCTAAGACTTCGGCTGAGAA
```

*FIG. 3CB*

| FIG. 3D | |
|---|---|
| FIG. 3DA | FIG. 3DB |

```
Insertion(><) or Deletion(<>)            1150      1160    (-1)1170      1180      1190      1200      1210      1220
                                     1147 ---+---------+------< >--+---------+---------+---------+---------+---------+----
Arcobacter sp clade 1 Consensus            CTCTAATGAGACTGCCTACG - CAAGTAGGAGGAAGGTGAGGACGACGTCAAGTCATCATGGCCCTTACGACCAGGGCTA
Arcobacter sp clade 1 Degenerate Consensus CTCTAAYGAGACTGCCTRSG - CAASYAGGAGGAAGGTGAGGACGACGTCAAGTCATCATGGCCCTTACGACCAGGGCTA
97AE3-12                                   CTCTAATGAGACTGCCTACG - CAAGTAGGAGGAAGGTGAGGACGACGTCAAGTCATCATGGCCCTTACGACCAGGGCTA
Arcobacter sp clade 2 Degenerate Consensus CTCTAAHGAGACTGCCTRSG - CAASYAGGAGGAAGGTGAGGACGACGTCAAGTCATCATGGCCCTTACGWCCAGGGCTA
Arcobacter sp clade 3 Degenerate Consensus CTCTAARGAGACTGCCTRSG - CAAGTAGGAGGAAGGTGAGGAYGACGTCAAGTCATCATGGCCCTTACGTCCAGGGCTA

                                                          |-------------------------------------------------------------->
Insertion(><) or Deletion(<>)             1230      1240      1250      1260      1270      1280   (-1) 1290      1300
                                     1226 ----+---------+---------+---------+---------+---------+-----< >---+---------+----
Arcobacter sp clade 1 Consensus            CACACGTGCTACAATGGGGTATACAAAGAGCAGCGATACAGTGATGTGGAGCAAATCTAA - AAAATACCTCCCAGTTCG
Arcobacter sp clade 1 Degenerate Consensus CACACGTGCTACAATGGGGTATACAAAGAGCAGCRATACRGYGAYGTGGAGCRAATCTHA - AAAATRYCTCYCAGTTCG
97AE3-12                                   CACACGTGCTACAATGGGGTATACAAAGAGCAGCGATACAGTGATGTGGAGCAAATCTAA - AAAATACCTCCCAGTTCG
Arcobacter sp clade 2 Degenerate Consensus CACACGTGCTACAATGGGGTATACAAAGAGCAGCRATACRGYGAYGTGGAGCRAATCTYA - AAAATRYCTCCCAGTTCG
Arcobacter sp clade 3 Degenerate Consensus CACACGTGCTACAATGGGRTATACARWGAGCNGCRATACGGTGACGTGGAGCAAATCTYA(T)AAAATRYCTCCCAGTTCG

                                           <----------------------Variable region 8-------------------------------|
Insertion(><) or Deletion(<>)               1310      1320      1330      1340 (+1)    1350      1360(+1)    1370        1380
                                     1305 -----+---------+---------+---------+--> - <-----+---------+> - <-------+    ---------+
Arcobacter sp clade 1 Consensus            GATTGTAGTCTGCAACTCGACTACATGAAGTTGGAATCG - CTAGTAATCGTAGATCAG C AATGCTACG -.GTGAATACGT
Arcobacter sp clade 1 Degenerate Consensus GATTGTAGTCTGCAACTCGACTACRTGAAGTTGGAATCG(G)CTAGTAATCGTAGATCAG C WAYGCTACG - GTGAATACGT
97AE3-12                                   GATTGTAGTCTGCAACTCGACTACATGAAGTTGGAATCG - CTAGTAATCGTAGATCAG C AATGCTACG - GTGAATACGT
Arcobacter sp clade 2 Degenerate Consensus GATTGWAGTCTGCAACTCGACTRCYTGAAGTTGGAATCG - CTAGTAATCGTAGATCAG C WAWGCTACG - GTGAATACGT
Arcobacter sp clade 3 Degenerate Consensus GATTGTAGTCTGCAACTCGACTACATGAAGTTGGAATCG - CTAGTAATCGTAGATCAG C TATGCTACG(A)GTGAATACGT
```

FIG. 3DA

```
------------------------------------------------------------------------------------------------------------------------------------
                                                                      |--------------Variable region 9-------------->
Insertion(><) or Deletion(<>)                 1390      1400      1410      1420      1430      1440      1450      1460
                                         1381 ---------+---------+---------+---------+---------+---------+---------+<(-6)>--+
Arcobacter sp clade 1 Consensus              TCCCGGGTCTTGTACTCACCGCCCGTCACACCATGGGAGTTGATTTCACTCGAAGCGGGGATGCTAAGAT------AGCT
Arcobacter sp clade 1 Degenerate Consensus   TCCCGGGTCTTGTACWCACCGCCCGTCACACCATGGGAGTTGAWTTCACYCGAAGCRGGGATGYTAARRT------ARCT
97AE3-12                                     TCCCGGGTCTTGTACTCACCGCCCGTCACACCATGGGAGTTGATTTCACTCGAAGCGGGGATGCTAAGAT------AGCT
Arcobacter sp clade 2 Degenerate Consensus   TCCCGGGTCTTGTACTCACCGCCCGTCACACCATGGGAGTTGAWYTCACTCGAAGCRGRGATGCTAAART------AGCT
Arcobacter sp clade 3 Degenerate Consensus   TCCCGGGTCTTGTACTCACCGCCCGTCACACCATGGGAGTTGAACTCACTCGAAGCGGGGATGCTAAART------AGCT

                                             <--------------------|
Insertion(><) or Deletion(<>)                 1470      1480      1490      1500      1510    SEQ ID NO
                                         1361 ---------+---------+---------+---------+---------+--
Arcobacter sp clade 1 Consensus              ACCCTCCACAGTGGAATTAGCGACTGGGGTGAAGTCGTAACAAGGTAACCG      39
Arcobacter sp clade 1 Degenerate Consensus   ACCYTCCHCAGTGGAWTYAGCGACTGGGGTGAAGTCGTAACARGGTAACCG      40
97AE3-12                                     ACCCTCCACAGTGGAATTAGCGACTGGGGTGAAGTCGTAACAAGGTAACCG       1
Arcobacter sp clade 2 Degenerate Consensus   ACCYTCCACAGTGGAWTYAGCGACTGGGGTGAAGTCGTAACARGGTAACCG      41
Arcobacter sp clade 3 Degenerate Consensus   ACCTTCCACAGTGGATTYAGCGACTGGGGTGAAGTCGTAACAAGGTAACCG      42
```

*FIG. 3DB*

```
A. Signature Sequence Variable region 2 34 bases
SEQ ID
 No.
                                          170      180       190        200  203
                                           +---------+---------+---------+---
47  Shewanella dominant signature          GCATACGCCCTACGGGGGAAAGAGGGGGACTTTC   203
48 Shewanella degenerate signature         GCATACGCCCTACGGGGGAAARRRGGGGMNYYTM   203

B. Signature Sequence Variable région 5 41 bases
                                          820       830       840       850       860
                                           +---------+---------+---------+---------+
49 Shewanella dominant signature           TCGGAGTTTGGTGTCTTGAACACTGGGCTCTCAAGCTAACG 860
50 Shewanella degenerate signature         TCGGARTTTGGTVHCTTRRACACTGGKYTYYMAAGCTAACG 860

C. Signature Sequence Variable region 8 96 bases
                                  1230      1240      1250      1260      1270     1379
                                   +---------+---------+---------+---------+---------
51 Shewanella dominant signature    ACAATGGCGAGTACAGAGGGTTGCAAAGCCGCGAGGTGGAGCTAATCTCA 1379
52 Shewanella degenerate signature  ACAATGGBVDDTACAGAGGGTTGCRAAGCCGCRAGGTSDAGCTAATCYCA 1379

                                           1280      1290      1300      1310      1320
                                             +---------+---------+---------+---------+-----
Shewanella dominant signature continued   CAAAGCTCGTCGTAGTCCGGATTGGAGTCTGCAACTCGACTCCATG 1325
Shewanella degenerate signature continued BAAAGBHBGTCGTAGTCCGGATYGGAGTCTGCAACTCGACTCCRTG 1325
```

Legend
R=A/G; Y=T/C; M=A/C; W=A/T; S=G/C; N=A/C/G/T; H=A/C/T/not G; V=A/C/G/not T B=C/G/T/ not A D=A/G/T/not C

*FIG. 5*

SEQUENCE LISTING

<160> NUMBER OF SEQ ID NOS: 52

<210> SEQ ID NO 1
<211> LENGTH: 1477
<212> TYPE: DNA
<213> ORGANISM: Unknown
<220> FEATURE:
<223> OTHER INFORMATION: Arcobacter species

<400> SEQUENCE: 1
agagtttgat tatggctcag agtgaacgct ggcggcgtgc ttaacacatg caagtcgaac 60
gagaacggga ttagcttgct aatctgtcag ctaagtggcg cacgggtgag taatatatag 120
gtaacgtgcc ttcaagaggg ggataacaga tggaaacgtc tgctaaaacc ccatatgcct 180
ttaatgcgaa agtatgcaag ggaaatattt atagcttgaa gatcggcctg tacagtatca 240
gatagttggt gaggtaatag ctcaccaagt caatgacgct taactggttt gagaggatga 300
tcagtcacac tggaactgag acacggtcca gactcctacg ggaggcagca gtggggaata 360
ttgcacaatg gggaaaccc tgatgcagca acgccgcgtg gaggatgaca catttcggtg 420
cgtaaactcc ttttatataa gaagataatg acggtattat atgaataagc accggctaac 480
tccgtgccag cagccgcggt aatacggagg gtgcaagcgt tactcggaat cactgggcgt 540
aaagagcgtg taggcggata gataagtcag aagtgaaatc caatagctta actattgaac 600
tgcttttgaa actgtctatc tagagtatgg gagaggtaga tggaatttct ggtgtagggg 660
taaaatccgt agagatcaga aggaataccg attgcgaagg cgatctactg gaacataact 720
gacgctgaga cgcgaaagcg tggggagcaa acaggattag ataccctggt agtccacgcc 780
ctaaacgatg tacactagtt gttgctatgc tcgacatagc agtaatgcag ttaacacatt 840
aagtgtaccg cctggggagt acggtcgcaa gattaaaact caaaggaata gacggggacc 900
cgcacaagcg gtggagcatg tggtttaatt cgacgatacg cgaagaacct tacctggtct 960
tgacatagta agaaccattt agagatagat gggtgtctgc ttgcagaaac ttatatacag 1020
gtgctgcacg gctgtcgtca gctcgtgtcg tgagatgttg ggttaagtcc cgcaacgagc 1080
gcaaccctcg tcattagttg ctaacacttc gggtgagaac tctaatgaga ctgcctacgc 1140
aagtaggagg aaggtgagga cgacgtcaag tcatcatggc ccttacgacc agggctacac 1200
acgtgctaca atggggtata caaagagcag cgatacagtg atgtggagca aatctaaaaa 1260
atacctccca gttcggattg tagtctgcaa ctcgactaca tgaagttgga atcgctagta 1320
atcgtagatc agcaatgcta cggtgaatac gttcccgggt cttgtactca ccgcccgtca 1380
caccatggga gttgatttca ctcgaagcgg ggatgctaag atagctaccc tccacagtgg 1440
aattagcgac tggggtgaag tcgtaacaag gtaaccg 1477

<210> SEQ ID NO 2
<211> LENGTH: 1437

<212> TYPE: DNA
<213> ORGANISM: Unknown
<220> FEATURE:
<223> OTHER INFORMATION: Arcobacter species
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t

<400> SEQUENCE: 2

```
agagtgaang ctggcggcgt gcttaacaca tgcaagtcga acgagaacgg gattagcttg     60

ctaatctgtc agctaagtgg cgcacgggtg agtaatatat aggtaacgtg ccttcaagag    120

ggggataaca gatggaaacg tctgctaaaa ccccatatgc ctttaatgcg aaagtatgca    180

agggaaatat ttatagcttg aagatcggcc tgtacagtat cagatagttg gtgaggtaat    240

agctcaccaa gtcaatgacg cttaactggt ttgagaggat gatcagtcac actggaactg    300

agacacggtc cagactccta cgggaggcag cagtggggaa tattgcacaa tgggggaaac    360

cctgatgcag caacgccgcg tggaggatga cacatttcgg tgcgtaaact cctnttatat    420

aagaagataa tgacggtatt atatgaataa gcaccggcta actccgtgcc agcagccgcg    480

gtaatacgga gggtgcaagc gttactcgga atcactgggc gtaaagagcg tgtaggcgga    540

tagataagtc agaagtgaaa tccaatagct taactattga actgcttttg aaactgtcta    600

tctagagtat gggagaggta gatggaattt ctggtgtagg ggtaaaatcc gtagagatca    660

gaaggaatac cgattgcgaa ggcgatctac tggaacataa ctgacgctga gacgcgaaag    720

cgtggggagc aaacaggatt agataccctg gtagtccacg ccctaaacga tgtacactag    780

ttgttgctat gctcgacata gcagtaatgc agttaacaca ttaagtgtac cgcctgggga    840

gtacggtcgc aaggttaaaa ctcaaaggaa tagacgggga cccgcacaag cggtggagta    900

tgtggtttaa ttcgacgata cgcgaagaac cttacctggt cttgacatag taagaaccat    960

ttagagatag atgggtgtct gcttgcagaa acttatatac aggtgctgca cggctgtcgt   1020

cagctcgtgt cgtgagatgt tgggttaagt cccgcaacga gcgcaaccct cgtcattagt   1080

tgctaacact tcgggtgaga actctaatga gactgcctac gcaagtagga ggaaggtgag   1140

gacgacgtca agtcatcatg gcccttacga ccagggctac acacgtgcta caatggggta   1200

tacaaagagc agcgatacag tgatgtggag caaatctaaa aaatacctcc cagttcggat   1260

tgtagtctgc aactcgacta catgaagttg gaatcgctag taatcgtaga tcagcaatgc   1320

tacggtgaat acgttcccgg gtcttgtaca caccgcccgt cacaccatgg gagttgattt   1380

cactcgaagc ggggatgcta agatagctac cctccacagt ggaattagcg actgggg      1437
```

<210> SEQ ID NO 3
<211> LENGTH: 1473
<212> TYPE: DNA
<213> ORGANISM: Unknown
<220> FEATURE:
<223> OTHER INFORMATION: Arcobacter species

<400> SEQUENCE: 3

```
agagtttgat cctggctcag agtaacgctg gcggcgtgct taacacatgc aagtcgaacg     60

agaacgggat tagcttgcta atctgtcagc taagtggcgc acgggtgagt aatatatagg    120

taacgtgcct tcaagagggg gataacagat ggaaacgtct gctaaaaccc catatgcctt    180
```

```
taatgcgaaa gtatgcaagg gaaatattta tagcttgaag atcggcctgt acagtatcag    240
atagttggtg aggtaatagc tcaccaagtc aatgacgctt aactggtttg agaggatgat    300
cagtcacact ggaactgaga cacggtccag actcctacgg gaggcagcag tggggaatat    360
tgcacaatgg gggaaaccct gatgcagcaa cgccgcgtgg aggatgacac atttcggtgc    420
gtaaactcct tttatataag aagataatga cggtattata tgaataagca ccggctaact    480
ccgtgccagc agccgcggta atacggaggg tgcaagcgtt actcggaatc actgggcgta    540
aagagcgtgt aggcggatag ataagtcaga agtgaaatcc aatagcttaa ctattgaact    600
gcttttgaaa ctgtctatct agagtatggg agaggtagat ggaatttctg gtgtaggggt    660
aaaatccgta gagatcagaa ggaataccga ttgcgaaggc gatctactgg aacataactg    720
acgctgagac gcgaaagcgt ggggagcaaa caggattaga taccctggta gtccacgccc    780
taaacgatgt acactagttg ttgctatgct cgacatagca gtaatgcagt taacacatta    840
agtgtaccgc ctggggagta cggtcgcaag attaaaactc aaaggaatag acggggaccc    900
gcacaagcgg tggagcatgt ggtttaattc gacgatacgc gaagaacctt acctggtctt    960
gacatagtaa gaaccattta gagatagatg ggtgtctgct tgcagaaact tatatacagg   1020
tgctgcacgg ctgtcgtcag ctcgtgtcgt gagatgttgg gttaagtccc gcaacgagcg   1080
caaccctcgt cattagttgc taacacttcg ggtgagaact ctaatgagac tgcctacgca   1140
agtaggagga aggtgaggac gacgtcaagt catcatggcc cttacgacca gggctacaca   1200
cgtgctacaa tggggtatac aaagagcagc gatacagtga tgtggagcaa atctaaaaaa   1260
tacctcccag ttcggattgt agtctgcaac tcgactacat gaagttggaa tcgctagtaa   1320
tcgtagatca gcaatgctac ggtgaatacg ttcccgggtc ttgtactcac cgcccgtcac   1380
accatgggag ttgatttcac tcgaagcggg gatgctaaga tagctaccct ccacagtgga   1440
attagcgact ggggtgaagt cgtaacaagg taa                                 1473
```

<210> SEQ ID NO 4
<211> LENGTH: 1426
<212> TYPE: DNA
<213> ORGANISM: Arcobacter marinus

<400> SEQUENCE: 4

```
ctggctcaga gtgaacgctg gcggcgtgct taacacatgc aagtcgaacg agaacgggat     60
tagcttgcta atctgtcagc taagtggcgc acgggtgagt aatatatagg taacgtgcct    120
tcaagagggg gataacagat ggaaacgtct gctaagaccc catatgcctt taatacaaaa    180
gtatgaaagg gaaatattta tagcttgaag atcggcctgt acagtatcag atagttggtg    240
aggtaatggc tcaccaagtc aatgacgctt aactggtttg agaggatgat cagtcacact    300
ggaactgaga cacggtccag actcctacgg gaggcagcag tggggaatat tgcacaatgg    360
gggaaaccct gatgcagcaa cgccgcgtgg aggatgacac atttcggtgc gtaaactcct    420
tttatataag aagataatga cggtattata tgaataagca ccggctaact ccgtgccagc    480
agccgcggta atacggaggg tgcaagcgtt actcggaatc actgggcgta aagagcgtgt    540
aggcggatag ataagtcaga agtgaaatcc aatagcttaa ctattgaact gcttttgaaa    600
ctgtctatct agagtatggg agaggtagat ggaatttctg gtgtaggggt aaaatccgta    660
gagatcagaa ggaataccga ttgcgaaggc gatctactgg aacataactg acgctgagac    720
gcgaaagcgt ggggagcaaa caggattaga taccctggta gtccacgccc taaacgatgt    780
acactagttg ttgctatgct cgacatagca gtaatgcagt taacacatta agtgtaccgc    840
```

```
ctggggagta cggtcgcaag attaaaactc aaaggaatag acggggaccc gcacaagcgg    900

tggagcatgt ggtttaattc gacgatacgc gaagaacctt acctggtctt gacatagtaa    960

gaaccattta gagatagatg ggtgtctgct tgcagaaact tatatacagg tgctgcacgg   1020

ctgtcgtcag ctcgtgtcgt gagatgttgg gttaagtccc gcaacgagcg caaccctcgt   1080

cattagttgc taacacttcg ggtgagaact ctaatgagac tgcctacgca agtaggagga   1140

aggtgaggac gacgtcaagt catcatggcc cttacgacca gggctacaca cgtgctacaa   1200

tggggtatac aaagagcagc gatacagtga tgtggagcaa atctaaaaaa tacctcccag   1260

ttcggattgt agtctgcaac tcgactacat gaagttggaa tcgctagtaa tcgtagatca   1320

gcaatgctac ggtgaatacg ttcccgggtc ttgtactcac cgcccgtcac accatgggag   1380

ttgatttcac tcgaagcggg gatgctaaga tagctaccct cctcag                  1426
```

<210> SEQ ID NO 5
<211> LENGTH: 1474
<212> TYPE: DNA
<213> ORGANISM: Unknown
<220> FEATURE:
<223> OTHER INFORMATION: Bacterium enrichment culture clone EB27.1

<400> SEQUENCE: 5

```
gtttgatcct ggctcagaag tgaacgctgg cggcgtgctt aacacatgca agtcgaacga     60

gaacgggatt agcttgctaa tctgtcagct aagtggcgca cgggtgagta atatataggt    120

aacgtgcctt caagaggggg ataacagatg gaaacgtctg ctaaaacccc atatgccttt    180

aatgcgaaag tatgcaaggg aaatatttat agcttgaaga tcggcctgta cagtatcaga    240

tagttggtga ggtaatagct caccaagtca atgacgctta actggtttga gaggatgatc    300

agtcacactg gaactgagac acggtccaga ctcctacggg aggcagcagt ggggaatatt    360

gcacaatggg ggaaaccctg atgcagcaac gccgcgtgga ggatgacaca tttcggtgcg    420

taaactcctt ttataagaag ataatgacgg tattatatga ataagcaccg gctaactccg    480

tgccagcagc cgcggtaata cggagggtgc aagcgttact cggagtcact gggcgtaaag    540

agcgtgtagg cggatagata agtcagaagt gaaatccaat agcttaacta ctgaactgct    600

tttgaaactg tctatctaga gtatgggaga ggtagatgga atttctggtg taggggtaaa    660

atccgtagag atcagaagga ataccgattg cgaaggcgat ctactggaac attactgacg    720

ctgagacgcg aaagcgtggg gagcaaacag gattagatac cctggtagtc cacgccctaa    780

acgatgtgca ctagttgttg cgatgctaga cattgcagta atgcagtaaa cacattaagt    840

gcaccgcctg ggagtacggg tcgcaagatt aaaactcaaa ggaaaagacg gggacccgca    900

caagcggtgg agcatgtggt ttaattcgac gatacgcgaa gaaccttacc tggtcttgac    960

atagaaagaa ctttccagag atggattggt gcctgcttgc aggagctttc atacaggtgc   1020

tgcacggctg tcgtcagctc gtgtcgtgag atgttgggtt aagtcccgca acgagcgcaa   1080

ccctcgtcgt tagttgctaa cagttcggct gagaactcta acgagactgc ctacgcaagt   1140

aggaggaagg tgaggacgac gtcaagtcat catggccctt acgaccaggg ctacacacgt   1200

gctacaatgg ggtatacaaa gagcagcaat acggtgacgt ggagcgaatc tcaaaaatgc   1260

ctcccagttc ggattgtagt ctgcaactcg actacatgaa gttggaatcg ctagtaatcg   1320

tagatcagct atgctacggt gaatacgttc ccgggtcttg tactcaccgc ccgtcacacc   1380

atgggagttg aattcattcg aagcggggat gctaaaatag ctaccttccc cagtggattt   1440
```

agcgactggg gtgaagtcgt aacaaggtag ccgt 1474

<210> SEQ ID NO 6
<211> LENGTH: 1402
<212> TYPE: DNA
<213> ORGANISM: Arcobacter halophilus

<400> SEQUENCE: 6
taacacatgc aagtcgaacg agaacggatt atagcttgct ataattgtca gctaagtggc 60
gcacgggtga gtaatatata ggtaacgtgc ctctaagaaa gggataacag atggaaacgt 120
ctgctaatac cttatatgcc tttaatacga aagtatgcaa gggaaacgct ttagtgctta 180
gagatcggcc tgtacagtat cagctagttg gtgaggtaag agctcaccaa ggcaatgacg 240
cttaactggt ttgagaggat gatcagtcac actggaactg agacacggtc cagactccta 300
cgggaggcag cagtggggaa tattgcacaa tgggggaaac cctgatgcag caacgccgcg 360
tggaggatga cacatttcgg tgcgtaaact ccttttatat aggaagaaaa tgacggtact 420
atatgaataa gcgccggcta actccgtgcc agcagccgcg gtaatacgga gggcgcaagc 480
gttactcgga atcactgggc gtaaagagcg tgtaggcgga tagataagtt aggagtgaaa 540
tcctatggct caaccataga actgcttcta aaactgtcta tctagagtat gggagaggta 600
gatggaattt ctggtgtagg ggtaaaatcc gtagagatca gaaggaatac cgattgcgaa 660
ggcgatctac tggaacataa ctgacgctga gacgcgaaag cgtggggagc aaacaggatt 720
agataccctg gtagtccacg ccctaaacga tgtacactag ttgttgccat gctcgacatg 780
gcagtaatgc agttaacaca ttaagtgtac cgcctgggga gtacggtcgc aagattaaaa 840
ctcaaaggaa tagacgggga cccgcacaag cggtggagca tgtggtttaa ttcgacgata 900
cgcgaagaac cttacctggt cttgacatag taagaaccat ttagagatag atgggtgtct 960
gcttgcagaa gcttatatac aggtgctgca cggctgtcgt cagctcgtgt cgtgagatgt 1020
tgggttaagt cccgcaacga gcgcaaccct cgtcgttagt tgctaacagt acggctgaga 1080
actctaacga gactgcctgg gcaaccagga ggaaggtgag gacgacgtca agtcatcatg 1140
gcccttacga ccagggctac acacgtgcta caatggggta tacaaagagc agcaatacag 1200
tgatgtggag caaatctaaa aaatacctcc cagttcggat agtagtctgc aactcgacta 1260
cttgaagttg gaatcgctag taatcgtaga tcagcaatgc tacggtgaat acgttcccgg 1320
gtcttgtact caccgcccgt cacaccatgg gagttgattt cactcgaagc ggggatgcta 1380
agatagctac cctccacagt gg 1402

<210> SEQ ID NO 7
<211> LENGTH: 1401
<212> TYPE: DNA
<213> ORGANISM: Arcobacter molluscorum

<400> SEQUENCE: 7
taacacatgc aagtcgaacg agaacggatt atagcttgct ataattgtca gctaagtggc 60
gcacgggtga gtaatatata ggtaatgtgc cttcaagagg gggataacag atggaaacgt 120
ctgctaagac cccatatgcc tttaatacaa aagtatgcaa gggaaatatt aatagcttga 180
agatcggcct gtacagtatc agatagttgg tgaggtaatg gctcaccaag tcaatgacgc 240
ttaactggtt tgagaggatg atcagtcaca ctggaactga gacacggtcc agactcctac 300
gggaggcagc agtggggaat attgcacaat gggggaaacc ctgatgcagc aacgccgcgt 360
ggaggatgac acatttcggt gcgtaaactc cttttatata ggaagataat gacggtacta 420

```
tatgaataag cgccggctaa ctccgtgcca gcagccgcgg taatacggag ggcgcaagcg    480

ttactcggaa tcactgggcg taaagagcgt gtaggcggat aaataagtca ggagtgaaat    540

ccaatagctc aactattgaa ctgcttttga aactgtttat ctagagtatg ggagaggtag    600

atggaatttc tggtgtaggg gtaaaatccg tagagatcag aaggaatacc gattgcgaag    660

gcgatctact ggaacataac tgacgctgag acgcgaaagc gtggggagca aacaggatta    720

gataccctgg tagtccacgc cctaaacgat gtacactagt tgttgctatg ctcgacatag    780

cagtaatgca gttaacacat taagtgtacc gcctggggag tacggtcgca agattaaaac    840

tcaaaggaat agacggggac ccgcacaagc ggtggagcat gtggtttaat tcgacgatac    900

gcgaagaacc ttacctggtc ttgacatagt aagaacattc cagagatggg atggtgtctg    960

cttgcagaaa cttatataca ggtgctgcac ggctgtcgtc agctcgtgtc gtgagatgtt   1020

gggttaagtc ccgcaacgag cgcaaccctc gtcattagtt gctaacactt cgggtgagaa   1080

ctctaatgag actgcctacg caagtaggag gaaggtgagg acgacgtcaa gtcatcatgg   1140

cccttacgac cagggctaca cacgtgctac aatggggtat acaaagagca gcgatacggt   1200

gacgtggagc aaatcttaaa aatatctctc agttcggatt gtagtctgca actcgactac   1260

atgaagttgg aatcgctagt aatcgtagat cagcaatgct acggtgaata cgttcccggg   1320

tcttgtactc accgcccgtc acaccatggg agttgatttc actcgaagca gggatgttaa   1380

gataactacc ttccacagtg g                                              1401
```

<210> SEQ ID NO 8
<211> LENGTH: 1544
<212> TYPE: DNA
<213> ORGANISM: Arcobacter mytili

<400> SEQUENCE: 8

```
taacacatgc aagtcgaacg agaacggatt atagcttgct ataattgtca gctaagtggc     60

gcacgggtga gtaatatata tcatggctca gagtgaacgc tggcggcgtg cttaacacat    120

gcaagtcgaa cgagaacggg atatagcttg ctatatttgt cagctaagtg gcgcacgggt    180

gagtaatgta taggtaacat gccctttaca aggaaataac agttggaaac gactgctaat    240

gtcctatatg cctttaatac taaagtatgc aagggaaaga tttatcggta aaggattggc    300

ctgtattgta tcagttagtt ggtggggtaa tggcctacca agacaatgac gcataactgg    360

tttgagagga tgatcagtca cactggaact gagacacggt ccagactcct acgggaggca    420

gcagtgggga atattgcaca atgggggaa ccctgatgca gcaacgccgc gtggaggatg    480

acacatttcg gtgcgtaaac tccttttata taggaagata atgacggtac tatatgaata    540

agcgccggct aactccgtgc cagcagccgc ggtaatacgg agggcgcaag cgttactcgg    600

aatcactggg cgtaaagagc gtgtaggcgg atcgataagt caggagtgaa atcctatggc    660

tcaaccatag aactgctctt gaaactgtca atctagagta tgggagaggt agatggaatt    720

tctggtgtag gggtaaaatc cgtagagatc agaaggaata ccgattgcga aggcgatcta    780

ctggaacata actgacgctg agacgcgaaa gcgtggggag caaacaggat tagataccct    840

ggtagtccac gccctaaacg atgtacacta gttgttgcca tactagatat ggcagtaatg    900

cagttaacac attaagtgta ccgcctgggg agtacggtcg caagattaaa actcaaagga    960

atagacgggg acccgcacaa gcggtggagc atgtggttta attcgacgat acgcgaagaa   1020

ccttacctgg tcttgacata gtaagaatat tttagagata gaatagtgct agcttgctag   1080
```

```
aacttacata caggtgctgc acggctgtcg tcagctcgtg tcgtgagatg ttgggttaag   1140

tcccgcaacg agcgcaaccc tcgtcgttag ttgctaacag ttcggctgag aactctaacg   1200

agactgccta cgcaagtagg aggaaggtga ggacgacgtc aagtcatcat ggcccttacg   1260

accagggcta cacacgtgct acaatggggt atacaaagag cagcaatacg gtgacgtgga   1320

gcaaatctca aaaatacctc ccagttcgga ttgtagtctg caactcgact acatgaagtt   1380

ggaatcgcta gtaatcgtag atcagctacg ctacggtgaa tacgttcccg ggtcttgtac   1440

tcaccgcccg tcacaccatg ggagttgatt tcactcgaag cagggatgct aagatagcta   1500

ccttccacag tggaatcagc gactggggtg aagtcgtaac aggg                    1544


<210> SEQ ID NO 9
<211> LENGTH: 1461
<212> TYPE: DNA
<213> ORGANISM: Arcobacter nitrofigilis
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t

<400> SEQUENCE: 9

atggagagtt tgatcctggc tcagagtgaa cgctggcggc gtgcttaaca catgcaagtc     60

gaacgagaac gggttaaagc ttgctttaac tgtcagctaa gtggcgcacg ggtgagtnat    120

atataggtaa catgccctag agagggggat aacagatgga aacgtctgct aacacccnat    180

atgcctttaa gacyaaagtc tgcaagggaa acatttatgg ctctaggatt ggcctgtacg    240

gtatcagcta gttggtgagg taatggctca ccaaggcaat gacacctaac tggtttgaga    300

ggatgatcag tcacactgga actgagacac ggtccagact cctacgggag gcagcagtgg    360

ggaatattgc acaatggacg aaagtctgat gcagcaacgc cgcgtggagg atgacacatt    420

tcggtgcgta aactcctttt atataggaag ataatgacgg tactatatga ataagcaccg    480

gctaactccg tgccagcagc cgcggtaata cggagggtgc aagcgttact cggaattact    540

gggcgtaaag agcgtgtagg cgggtaaata agttggaagt gaaatcctat ggctcaacca    600

tagaactgct tccaaaactg ttaacctaga atgtgggaga ggtagatgga atttctggtg    660

taggggtaaa atccgtagat atcagaagga ataccgattg cgaaggcgat ctactggaac    720

atnattgacg ctgagacgcg aaagcgtggg gagcaaacag gattngatnc cctggtagtc    780

cacgccctna acgatgtaca ctagttgttg tgaggctaga ccttgcagta atgcagttaa    840

cacattaagt gtaccgcctg gggagtacgg tcgcaagatt aaaactcaaa ggaatagacg    900

gggacccgca caagcggtgg agcatgtggt ttaattcgaa gatacacgaa gaaccttacc    960
```

```
tggtcttgac atagtaagaa ctttttagag ataaattggt gtctgcttgc agaaacttac   1020

atacaggtgc tgcacggctg tcgtcagctc gtgtcgtgag atgttgggtt aagtcccgca   1080

acgagcgcaa ccctcgtcgt tagttgctaa cagttcggct gagaactcta acgagactgc   1140

ctacgcaagt aggaggaagg tgaggacgac gtcaagtcat catggccctt acgaccaggg   1200

ctacacacgt gctacaatgg ggtatacaaa gagcagcgat acggtgacgt ggagcgaatc   1260

tcaaaaatgc ctcccagttc ggattgtagt ctgcaactcg actacatgaa gttggaatcg   1320

ctagtaatcg tagatcagct atgctacggt gaatacgttc ccgggtcttg tactcaccgc   1380

ccgtcacacc atgggagtts aattcattcg aagcggggat gctaaaatag ctaccttcca   1440

cagtggattt agygactggg g                                              1461
```

<210> SEQ ID NO 10
<211> LENGTH: 1403
<212> TYPE: DNA
<213> ORGANISM: Arcobacter defluvii

<400> SEQUENCE: 10

```
taacacatgc aagtcgaacg agaacggatt atagcttgct ataattgtca gctaagtggc     60

gcacgggtga gtaatgtata gataacctgc cctctagaaa ggaataacag atggaaacgt    120

ctgctaatgc cctatatgcc tttaatacat aagtatgcaa gggaaacgct ttagtgctag    180

aggatgggtc tgtatggtat cagcttgttg gtgaggtaat ggctcaccaa ggcaatgacg    240

cctaactggt ttgagaggat gatcagtcac actggaactg agacacggtc cagactccta    300

cgggaggcag cagtggggaa tattgcacaa tggacgaaag tctgatgcag caacgccgcg    360

tggaggatga cacatttcgg tgcgtaaact ccttttatat aggaagataa tgacggtact    420

atatgaataa gcaccggcta actccgtgcc agcagccgcg gtaatacgga gggtgcaagc    480

gttactcgga atcactgggc gtaaagagcg tgtaggcggg tatataagtc agaagtgaaa    540

tccaatagct taactwttga actgcttttg aaactgtata cctaraaatgt gggagaggta    600

gatggaattt ctggtgtagg ggtaaaatcc gtagagatca gaaggaatac cgattgcgaa    660

ggcgatctac tggaacatta ttgacgctga gacgcgaaag cgtggggagc aaacaggatt    720

agataccctg gtagtccacg ccctaaacga tgtacactag ttgttgtgag gctcgacctt    780

gcagtaatgc agttaacaca ttaagtgtmc cgcctgggga gtacggtcgc aagattaaaa    840

ctcaaaggaa tagacgggga cccgcacaag cggtggagca tgtggtttaa ttcgacgata    900

cacgaagaac cttacctgga cttgacatag taagaacttt ctagagatag attggtgtct    960

gcttgcagaa acttatatac aggtgctgca cggctgtcgt cagctcgtgt cgtgagatgt   1020

tgggttaagt cccgcaacga gcgcaaccct cgtcattagt tgctaacagt tcggctgaga   1080

actctaatga gactgcctac gcaagtagga ggaaggtgag gacgacgtca agtcatcatg   1140

gcccttacgt ccagggctac acacgtgcta caatggggta tacaaagagc agcaatacag   1200

tgatgtggag caaatctcaa aaatatctcc cagttcggat tgtagtctgc aactcgacta   1260

catgaagttg gaatcggcta gtaatcgtag atcagctatg ctacggtgaa tacgttcccg   1320

ggtcttgtac tcaccgcccg tcacaccatg ggagttgaac tcattcgaag cggggatgct   1380

aaagtagcta ccttccacag tgg                                           1403
```

<210> SEQ ID NO 11
<211> LENGTH: 1464
<212> TYPE: DNA

<213> ORGANISM: Unknown
<220> FEATURE:
<223> OTHER INFORMATION: Arcobacter species

<400> SEQUENCE: 11

```
tgatccctgg ctcagagtga acgctggcgg cgtgcttaac acatgcaagt cgaacgagaa     60
cggattatag cttgctataa ttgtcagcta agtggcgcac gggtgagtaa tatataggta    120
atgtgcccta gagaagagga taacagttgg aaacgactgc taagactcta tatgccttta    180
agacagaagt ctgcaaggga aatatttata gctctaggat cagcctgtac agtatcagct    240
agttggtgag gtaatggctc accaaggcaa tgacacttaa ctggtttgag aggatgatca    300
gtccacactg gaactgagac acggtcccag actcctacgg gaggcagcag tggggaatat    360
tgcacaatgg acgaaagtct gatgcagcaa cgccgcgtgg aggatgacac attttcggtg    420
cgtaaactcc ttttatatgg gaagataatg acggtaccat atgaataagc accggctaac    480
tccgtgccag cagccgcggt aatacggagg gtgcaagcgt tactcggaat cactgggcgt    540
aaagagcgtg taggcggata tataagtcag aagtgaaatc caatagctta actattgaac    600
tgcttttgaa actgtatatc tagaatgtgg gagaggtaga tggaatttct ggtgtagggg    660
taaaatccgt agagatcaga aggaataccg attgcgaagg cgatctactg gaacattatt    720
gacgctgaga cgcgaaagcg tggggagcaa acaggattag ataccctggt agtccacgcc    780
ctaaacgatg cacactagtt gttgtgaggc tagaccttgc agtaatgcag ttaacacatt    840
aagtgtgccg cctggggagt acggtcgcaa gattaaaact caaaggaata gacggggacc    900
cgcacaagcg gtggagcatg tggtttaatt cgacgataca cgaagaacct tacctggact    960
tgacatagta agaactttct agagatagat tggtgtctgc ttgcagaaac ttatatacag   1020
gtgctgcacg gctgtcgtca gctcgtgtcg tgagatgttg ggttaagtcc cgcaacgagc   1080
gcaaccctcg tcattagttt gctaacagtt cggctgagaa ctctaatgag actgcctacg   1140
taagtaggag gaaggtgagg acgacgtcaa gtcatcatgg cccttacgtc cagggctaca   1200
cacgtgctac aatggggtat acaaagagcc gcaatacagt gatgtggagc aaatctcaaa   1260
aatatctccc agttcggatt gtagtctgca actcgactac atgaagttgg aatcgctagt   1320
aatcgtagat cagctatgct acggtgaata cgttcccggg tcttgtactc accgcccgtc   1380
acaccatggg agttgaactc attcgaagcg gggatgctaa aatagctacc ttccacagtg   1440
gatttagcga ctggggtgaa gtcg                                          1464
```

<210> SEQ ID NO 12
<211> LENGTH: 1455
<212> TYPE: DNA
<213> ORGANISM: Unknown
<220> FEATURE:
<223> OTHER INFORMATION: Arcobacter species

<400> SEQUENCE: 12

```
gctggcggcg tgcttaacac atgcaagtcg aacgagaacg gattaaagct tgctttaatt     60
gtcagctaag tggcgcacgg gtgagtaata tataggtaac gtgccttcaa gaaggggata    120
acaattggaa acgattgcta ataccctata tgcctttagg acttaagtct gcaagggaaa    180
tatttatagc ttgaagatcg gcctgtacag tatcagttag ttggtgaggt aatggctcac    240
caagacaatg acgcttaact ggtttgagag gatgatcagt cacactggaa ctgagacacg    300
gtccagactc ctacgggagg cagcagtggg gaatattgca caatggacga aagtctgatg    360
cagcaacgcc gcgtggagga tgacacattt cggtgcgtaa actcctttta tataggaaga    420
```

```
taatgacggt actatatgaa taagcaccgg ctaactccgt gccagcagcc gcggtaatac    480
ggagggtgca agcgttactc ggaatcactg ggcgtaaaga gaatgtaggc ggatagataa    540
gtttgaagtg aaatccaatg gctcaaccat tgaactgctt tgaaaactgt ckatctagaa    600
tatgggagag gtagatggaa tttctggtgt aggggtaaaa tccgtagaga tcagaaggaa    660
taccgattgc gaaggcgatc tactggaaca ttattgacgc tgagattcga aagcgtgggg    720
agcaaacagg attagatacc ctggtagtcc acgccctaaa cgatgcacac tagttgttgt    780
gaggctagac cttgcagtaa tgcagttaac acattaagtg tgccgcctgg ggagtacggt    840
cgcaagatta aaactcaaag gaatagacgg ggacccgcac aagcggtgga gcatgtggtt    900
taattcgacg atacgcgaag aaccttacct ggacttgaca tagatagaat ataacagaga    960
tgtaatagtg ctagcttgct agaactatca tacaggtgct gcacggctgt cgtcagctcg   1020
tgtcgtgaga tgttgggtta agtcccgcaa cgagcgcaac cctcgtcatt agttgctaac   1080
agttcggctg agaactctaa tgagactgcc tgggtaacca ggaggaaggt gaggacgacg   1140
tcaagtcatc atggccctta cgtccagggc tacacacgtg ctacaatggg gtatacaaag   1200
agcagcaata cmgygakgtg gagcaaatct caaaaatatc tcccagttcg gatagcagtc   1260
tgcaactcga ctgcttgaag ttggaatcgc tagtaatcgt agatcagcaa tgctacggtg   1320
aatacgttcc cgggtcttgt actcaccgcc cgtcacacca tgggaattga actcattcga   1380
agcgggaatg ctaaagtagc taccctccac agtggattca gtaactgggg tgaagtcgta   1440
acaaggtaac cgtag                                                    1455
```

<210> SEQ ID NO 13
<211> LENGTH: 1478
<212> TYPE: DNA
<213> ORGANISM: Unknown
<220> FEATURE:
<223> OTHER INFORMATION: Arcobacter species

<400> SEQUENCE: 13

```
agagtttgat cctggctcag agtgaacgct ggcggcgtgc ttaacacatg caagtcgaac     60
gagaacgggt attagcttgc taatactgtc agctaagtgg cgcacgggtg agtaatatat    120
agttaacctg ccctagagaa ggggataacg tttggaaacg gacgctaaca ccctatatgc    180
ctttaataca taagtatgca agggaaacat ttatggctct aggatgggac tgtacggtat    240
cagttagttg gtgaggtaat ggctcaccaa gacaatgaca cctaactggt ttgagaggat    300
gatcagtcac actggaactg agacacggtc cagactccta cgggaggcag cagtggggaa    360
tattgcacaa tggacgaaag tctgatgcag caacgccgcg tggaggatga cacatttcgg    420
tgcgtaaact ccttttatat aggaagataa tgacggtact atatgaataa gcaccggcta    480
actccgtacc agcagccgcg gtaatacgga gggtgcaagc gttactcgga atcactgggc    540
gtaaagagcg tgtaggcgga ttaataagtt ggaagtgaaa tcctatggct caaccataga    600
actgctttca aaactgttta tctagaatat gggagaggta gatggaattt ctggtgtagg    660
ggtaaaatcc gtagagatca gaaggaatac cgattgcgaa ggcgatctac tggaacatta    720
ttgacgctga gacgcgaaag cgtggggagc aaacaggatt agataccctg gtagtccacg    780
ccctaaacga tgcacactag ttgttgcgag gctagacctt gcagtaatgc agttaacaca    840
ttaagtgtgc cgcctgggga gtacggtcgc aagattaaaa ctcaaaggaa tagacgggga    900
cccgcacaag cggtggagca tgtggtttaa ttcgacgata cgcgaagaac cttacctgga    960
```

```
cttgacatag taagaacgtt ctagagatag aatggtgtct gcttgcagaa acttatatac   1020

aggtgctgca cggctgtcgt cagctcgtgt cgtgagatgt tgggttaagt cccgcaacga   1080

gcgcaaccct cgtgtttagt tgataacagt tcggctgata actctaaaca gactgcctgg   1140

gtaaccagga ggaaggtgag gacgacgtca agtcatcatg gcccttatgt ccagggctac   1200

acacgtgcta caatggggta tacaaagagc agcgatacgg tgacgtggag caaatctcaa   1260

aaatatctcc cagttcggat agtagtctgc aactcgacta cttgaagttg gaatcgctag   1320

taatcgtaga tcagcaatgc tacggtgaat acgttcccgg gtcttgtact caccgcccgt   1380

cacaccatgg gagttgaact cattcgaagc ggggatgcta aagtagctac cctccacagt   1440

ggatttagcg actggggtga agtcgtaaca aggtaacc                           1478
```

<210> SEQ ID NO 14
<211> LENGTH: 1507
<212> TYPE: DNA
<213> ORGANISM: Unknown
<220> FEATURE:
<223> OTHER INFORMATION: Arcobacter species

<400> SEQUENCE: 14

```
agagtttgat tatggctcag agtgaacgct ggcggcgtgc ttaacacatg caagtcgaac     60

gagaacgggt tatagcttgc tataattgtc agctaagtgg cgcacgggtg agtaatatat    120

aggtaacgtg ccctagagag gggataaca gttggaaacg actgctaaca ccccatatgc     180

ctttaataca aatgtatgca agggaaatat ttatagctct aggatcggcc tgtacggtat    240

cagcttgttg gtgaggtaat ggctcaccaa ggcaatgaca cctaactggt ttgagaggat    300

gatcagtcac actggaactg agacacggtc cagactccta cgggaggcag cagtggggaa    360

tattgcacaa tggacgaaag tctgatgcag caacgccgcg tggaggatga cacatttcgg    420

tgcgtaaact ccttttatat aggaagataa tgacggtact atatgaataa gcaccggcta    480

actccgtgcc agcagccgcg gtaatacgga gggtgcaagc gttactcgga atcactgggc    540

gtaaagagca tgtaggcggg taattaagtc agaagtgaaa tccaatagct caactattga    600

actgcttttg aaactggtta cctagaatat gggagaggta gatggaattt ctggtgtagg    660

ggtaaaatcc gtagagatca gaaggaatac cgattgcgaa ggcgatctac tggaacatta    720

ttgacgctga gatgcgaaag cgtggggagc aaacaggatt agataccctg gtagtccacg    780

ccctaaacga tgcacactag ttgttgctat gctagacata gcagtaatgc agttaacaca    840

ttaagtgtgc cgcctgggga gtacggtcgc aagattaaaa ctcaaaggaa tagacgggga    900

cccgcacaag cggtggagca tgtggtttaa ttcgacgata cgcgaagaac cttacctgga    960

cttgacatag taagaacctt ttagagatag aagggtgtct gcttgcagaa acttatatac   1020

aggtgctgca cggctgtcgt cagctcgtgt cgtgagatgt tgggttaagt cccgcaacga   1080

gcgcaaccct cgtcgttagt tgctaacagt tcggctgaga actctaacga gactgcctgg   1140

gtaaccagga ggaaggtgag gacgacgtca agtcatcatg gcccttacgt ccagggctac   1200

acacgtgcta caatggggta tacaaagagc agcgatacgg tgacgtggag caaatcttaa   1260

aaatatctcc cagttcggat tgtagtctgc aactcgacta catgaagttg gaatcgctag   1320

taatcgtaga tcagcaatgc tacggtgaat acgttcccgg gtcttgtact caccgcccgt   1380

cacaccatgg gagttgattt cattcgaagc ggggatgcta aagtagctac cctccacagt   1440

ggaattagcg actggggtga agtcgtaaca aggtaaccgt aggagaacct gcggttggat   1500

cacctcc                                                             1507
```

<210> SEQ ID NO 15
<211> LENGTH: 1505
<212> TYPE: DNA
<213> ORGANISM: Arcobacter nitrofigilis

<400> SEQUENCE: 15

```
agagtttgat cctggctcag agtgaacgct ggcggcgtgc ttaacacatg caagtcgaac     60

gagaacgggt taaagcttgc tttaactgtc agctaagtgg cgcacgggtg agtaatatat    120

aggtaacatg ccctagagag gggataaca gatggaaacg tctgctaaca ccccatatgc    180

ctttaagacc taagtctgca agggaaacat ttatggctct aggattggcc tgtacggtat    240

cagctagttg gtgaggtaat ggctcaccaa ggcaatgaca cctaactggt ttgagaggat    300

gatcagtcac actggaactg agacacggtc cagactccta cgggaggcag cagtggggaa    360

tattgcacaa tggacgaaag tctgatgcag caacgccgcg tggaggatga cacatttcgg    420

tgcgtaaact ccttttatat aggaagataa tgacggtact atatgaataa gcaccggcta    480

actccgtgcc agcagccgcg gtaatacgga gggtgcaagc gttactcgga attactgggc    540

gtaaagagcg tgtaggcggg taaataagtt ggaagtgaaa tcctatggct caaccataga    600

actgcttcca aaactgttaa cctagaatgt gggagaggta gatggaattt ctggtgtagg    660

ggtaaaatcc gtagatatca gaaggaatac cgattgcgaa ggcgatctac tggaacataa    720

ttgacgctga gacgcgaaag cgtgggggagc aaacaggatt agataccctg gtagtccacg    780

ccctaaacga tgtacactag ttgttgtgag gctagacctt gcagtaatgc agttaacaca    840

ttaagtgtac cgcctgggga gtacggtcgc aagattaaaa ctcaaaggaa tagacgggga    900

cccgcacaag cggtggagca tgtggtttaa ttcgacgata cgcgaagaac cttacctggt    960

cttgacatag taagaacttt ttagagataa attggtgtct gcttgcagaa acttacatac   1020

aggtgctgca cggctgtcgt cagctcgtgt cgtgagatgt tgggttaagt cccgcaacga   1080

gcgcaaccct cgtcgttagt tgctaacagt tcggctgaga actctaacga gactgcctac   1140

gcaagtagga ggaaggtgag gacgacgtca agtcatcatg gcccttacga ccagggctac   1200

acacgtgcta caatggggta tacaaagagc agcgatacgg tgacgtggag cgaatctcaa   1260

aaatgcctcc cagttcggat tgtagtctgc aactcgacta catgaagttg gaatcgctag   1320

taatcgtaga tcagctatgc tacggtgaat acgttcccgg gtcttgtact caccgcccgt   1380

cacaccatgg gagttgaatt cattcgaagc ggggatgcta aaatagctac cttccacagt   1440

ggatttagcg actggggtga agtcgtaaca aggtaaccgt aggagaacct gcggttggat   1500

cacct                                                               1505
```

<210> SEQ ID NO 16
<211> LENGTH: 1467
<212> TYPE: DNA
<213> ORGANISM: Arcobacter nitrofigilis

<400> SEQUENCE: 16

```
acatggctca gagtgaacgc tggcggcgtg cttaacacat gcaagtcgaa cgagaacggg     60

ttaaagcttg ctttaactgt cagctaagtg gcgcacgggt gagtaatata taggtaacat    120

gccctagaga gggggataac agatggaaac gtctgctaac accccatatg cctttaagac    180

gtaagtctgc aagggaaaca tttatggctc taggattggc ctgtacggta tcagttagtt    240

ggtgaggtaa tggctcacca agacaatgac acctaactgg tttgagagga tgatcagtca    300
```

```
cactggaact gagacacggt ccagactcct acgggaggca gcagtgggga atattgcaca    360

atggacgaaa gtctgatgca gcaacgccgc gtggaggatg acacatttcg gtgcgtaaac    420

tccttttata taggaagata atgacggtac tatatgaata agcaccggct aactccgtgc    480

cagcagccgc ggtaatacgg agggtgcaag cgttactcgg aattactggg cgtaaagagc    540

gtgtaggcgg gtaaataagt tggaagtgaa atcctatggc tcaaccatag aactgcttcc    600

aaaactgtta acctagaatg tgggagaggt agatggaatt tctggtgtag ggtaaaatc     660

cgtagatatc agaaggaata ccgattgcga aggcgatcta ctggaacaca attgacgctg    720

agacgcgaaa gcgtggggag caaacaggat tagataccct ggtagtccac gccctaaacg    780

atgtacacta gttgttgtga ggctagacct tgcagtaatg cagttaacac attaagtgta    840

ccgcctgggg agtacggtcg caagattaaa actcaaagga atagacgggg acccgcacaa    900

gcggtggagc atgtggttta attcgacgat acgcgaagaa ccttacctgg tcttgacata    960

gaaagaactt tccagagatg gattggtgcc tgcttgcagg agctttcata caggtgctgc   1020

acggctgtcg tcagctcgtg tcgtgagatg ttgggttaag tcccgcaacg agcgcaaccc   1080

tcgtcgttag ttgctaacag ttcggctgag aactctaacg agactgccta cgcaagtagg   1140

aggaaggtga ggacgacgtc aagtcatcat ggcccttacg accagggcta cacacgtgct   1200

acaatggggt atacaaagag cagcaatacg gtgacgtgga gcgaatctca aaaatgcctc   1260

ccagttcgga ttgtagtctg caactcgact acatgaagtt ggaatcgcta gtaatcgtag   1320

atcagctatg ctacggtgaa tacgttcccg ggtcttgtac tcaccgcccg tcacaccatg   1380

ggagttgaat tcattcgaag cggggatgct aaaatagcta ccttccacag tggatttagc   1440

gactggggtg aagtcgtaac aggggta                                       1467
```

<210> SEQ ID NO 17
<211> LENGTH: 1441
<212> TYPE: DNA
<213> ORGANISM: Arcobacter cryaerophilus

<400> SEQUENCE: 17

```
agagtgaacg ctggcggcgt gcttaacaca tgcaagtcga acgagaacgg gctatagctt     60

gctatagttg tcagctaagt ggcgcacggg tgagtaatgt ataggtaata tgcctcttac    120

taagggataa caattggaaa cgattgctaa taccttatac tccttattaa cctaagttaa    180

taagggaaag atttattggt aagagattag cctgtattgt atcagttagt tggtggggta    240

atggcctacc aagactatga cacataactg gtttgagagg atgatcagtc acactggaac    300

tgagacacgg tccagactcc tacgggaggc agcagtgggg aatattgcac aatggacgaa    360

agtctgatgc agcaacgccg cgtggaggat gacacatttc ggtgcgtaaa ctccttttat    420

atgagaagat aatgacggta ttatatgaat aagcaccggc taactccgtg ccagcagccg    480

cggtaatacg gggtgcaag cgttactcgg aatcactggg cgtaaagagc atgtaggcgg     540

attaataagt ttgaagtgaa atcctatagc ttaactatag aactgctttg aaaactgtta    600

atctagaatg tgggagaggt agatggaatt tctggtgtag ggtaaaatc cgtagagatc     660

agaaggaata ccgattgcga aggcgatcta ctggaacatt attgacgctg agatgcgaaa    720

gcgtggggag caaacaggat tagataccct ggtagtccac gccctaaacg atgtacacta    780

gttgttgtga gacttgatct tgcagtaatg cagttaacac attaagtgta ccgcctgggg    840

agtacggtcg caagattaaa actcaaagga atagacgggg acccgcacaa gcggtggagc    900

atgtggttta attcgacgat acacgaagaa ccttacctgg acttgacata gtaagaactt    960
```

```
tctagagata gattggtgtc tgcttgcaga aacttatata caggtgctgc acggctgtcg   1020
tcagctcgtg tcgtgagatg ttgggttaag tcccgcaacg agcgcaaccc tcgtgtttag   1080
ttgctaacag ttcggctgag aactctaaac agactgccta cgcaagtagg aggaaggtga   1140
ggacgacgtc aagtcatcat ggcccttacg tccagggcta cacacgtgct acaatgggat   1200
atacaaagag cggcaatacg gtgacgtgga gcaaatctta taaaatatct cccagttcgg   1260
attgtagtct gcaactcgac tacatgaagt tggaatcgct agtaatcgta gatcagctat   1320
gctacggtga atacgttccc gggtcttgta ctcaccgccc gtcacaccat gggagtcgaa   1380
ctcattcgaa gcggggatgc taaaatagct accttccaca gtggatttgg cgactggggt   1440
g                                                                   1441
```

<210> SEQ ID NO 18
<211> LENGTH: 1460
<212> TYPE: DNA
<213> ORGANISM: Arcobacter cibarius

<400> SEQUENCE: 18

```
gcggcgtgct taacacatgc aagtcgaacg agaacgggtt atagcttgct ataattgtca     60
gctaagtggc gcacgggtga gtaatgtata ggtaatatgc ctcttactaa gggataacaa    120
atggaaacgt ttgctaatac cttatactcc ttactaacta aagttagtaa gggaaagatt    180
tattggtaag agattagcct gtattgtatc agttagttgg tggggtaatg gcctaccaag    240
acaatgacgc ataactggtt tgagaggatg atcagtcaca ctggaactga gacacggtcc    300
agactcctac gggaggcagc agtggggaat attgcacaat ggacgaaagt ctgatgcagc    360
aacgccgcgt ggaggatgac acatttcggt gcgtaaactc cttttatata agaagataat    420
gacggtatta tatgaataag caccggctaa ctccgtgcca gcagccgcgg taatacgggg    480
ggtgcaagcg ttactcggaa tcactgggcg taaagagcat gtaggcggat taataagttt    540
gaagtgaaat cctatagctt aactatagaa ctgctttgaa aactgttagt ctagaatgtg    600
ggagaggtag atggaatttc tggtgtaggg gtaaaatccg tagagatcag aaggaatacc    660
gattgcgaag gcgatctact ggaacattat tgacgctgag atgcgaaagc gtggggagca    720
aacaggatta gataccctgg tagtccacgc cctaaacgat gtacactagt tgttgtgaga    780
cttgatcttg cagtaatgca gttaacacat taagtgtacc gcctggggag tacggtcgca    840
agattaaaac tcaaaggaat agacggggac ccgcacaagc ggtggagcat gtggtttaat    900
tcgacgatac acgaagaacc ttacctggac ttgacatagt aagaactttc tagagataga    960
ttggtgtctg cttgcagaaa cttatataca ggtgctgcac ggctgtcgtc agctcgtgtc   1020
gtgagatgtt gggttaagtc ccgcaacgag cgcaaccctc gtccttagtt gctaacagtt   1080
cggctgagaa ctctaaggag actgcctacg caagtaggag gaaggtgagg acgacgtcaa   1140
gtcatcatgg cccttacgtc cagggctaca cacgtgctac aatgggatat acaatgagcc   1200
gcaatacggt gacgtggagc aaatcttata aaatatctcc cagttcggat tgtagtctgc   1260
aactcgacta catgaagttg gaatcgctag taatcgtaga tcagctatgc tacgagtgaa   1320
tacgttcccg ggtcttgtac tcaccgcccg tcacaccatg ggagttgaac tcattcgaag   1380
cggggatgct aaagtagcta ccttccacag tggattcagc gactggggtg aagtcgtaac   1440
aaggtaaccg taggagaacc                                               1460
```

<210> SEQ ID NO 19

```
<211> LENGTH: 1483
<212> TYPE: DNA
<213> ORGANISM: Arcobacter thereius
<220> FEATURE:
<221> NAME/KEY: misc_feature
<222> LOCATION: (1478)..(1478)
<223> OTHER INFORMATION: n is a, c, g, or t

<400> SEQUENCE: 19

tagagtttga tcatggctca gagtgaacgc tggcggcgtg cttaacacat gcaagtcgaa     60

cgagaacggg ctatagcttg ctatagttgt cagctaagtg gcgcacgggt gagtaatgta    120

taggtaatat gccttttact aagggataac agttggaaac gactgctaat accttatatt    180

ccttttcaac ataagttgat aagggaaaga tttattggta agagattagc ctgtattgta    240

tcagttagtt ggtggggtaa tggctcacca agacaatgac gcataactgg tttgagagga    300

tgatcagtca cactggaact gagacacggt ccagactcct acgggaggca gcagtgggga    360

atattgcaca atggacggaa gtctgatgca gcaacgccgc gtggaggatg acacatttcg    420

gtgcgtaaac tccttttata taagaagata atgacggtat tatatgaata agcaccggct    480

aactccgtgc cagcagccgc ggtaatacgg ggggtgcaag cgttactcgg aatcactggg    540

cgtaaagagc atgtaggcgg attgataagt ttgaagtgaa atcctatagc ttaactatag    600

aactgctttg aaaactgtta atctagaatg tgggagaggt agatggaatt tctggtgtag    660

gggtaaaatc cgtagagatc agaaggaata ccgattgcga aggcgatcta ctggaacact    720

attgacgctg agatgcgaaa gcgtggggag caaacaggat tagataccct ggtagtccac    780

gccctaaacg atgtacacta gttgttgtga gacttgatct tgcagtaatg cagttaacac    840

attaagtgta ccgcctgggg agtacggtcg caagattaaa actcaaagga atagacgggg    900

acccgcacaa gcggtggagc atgtggttta attcgacgat acgcgaagaa ccttacctgg    960

acttgacata gtaagaactt tcaagagatt gattggtgtc tgcttgcaga aacttatata   1020

caggtgctgc acggctgtcg tcagctcgtg tcgtgagatg ttgggttaag tcccgcaacg   1080

agcgcaaccc tcgtgtttag ttgctaacag ttcggctgag aactctaaac agactgccta   1140

cgcaagtagg aggaaggtga ggacgacgtc aagtcatcat ggcccttacg tccagggcta   1200

cacacgtgct acaatgggat atacagtgag ctgcgataca gtgatgtgga gcaaatctta   1260

taaaatatct cccagttcgg attgtagtct gcaactcgac tacatgaagt tggaatcgct   1320

agtaatcgta gatcagctat gctacggtga atacgttccc gggtcttgta ctcaccgccc   1380

gtcacaccat gggagtcgaa ctcattcgaa gcggggatgc taaagtagct accttccaca   1440

gtggatttgg cgactggggt gaagtcgtaa caaggtancc gta                      1483


<210> SEQ ID NO 20
<211> LENGTH: 1462
<212> TYPE: DNA
<213> ORGANISM: Arcobacter skirrowi
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
```

<222> LOCATION: (818)..(818)
<223> OTHER INFORMATION: n is a, c, g, or t
<220> FEATURE:
<221> NAME/KEY: misc_feature
<222> LOCATION: (918)..(925)
<223> OTHER INFORMATION: n is a, c, g, or t
<220> FEATURE:
<221> NAME/KEY: misc_feature
<222> LOCATION: (940)..(943)
<223> OTHER INFORMATION: n is a, c, g, or t

<400> SEQUENCE: 20

```
atggagagtt tgatcctggc tcagagtgaa cgctggcggc gtgcttaaca catgcaagtc     60

gaacgagaac gggctatagc ttgctatagt tgtcagctaa gtggcgcacg ggtgagtaat    120

gtataggtaa tatgcctctt actaagggat aacaaatgga aacgtttgct nataccttat    180

actcctntta aacaaaagtt taaaagggaa agatttattg gtaagagatt agcctgtatt    240

gtatcagtta gttggtgggg taatggctta ccaagactat gacacataac tggtttgaga    300

ggatgatcag tcacactgga actgagacac ggtccagact cctrcgggag gcagcagtgg    360

ggaatattgc acaatggacg aaagtctgat gcagcaacgc cgcgtggagg atgacacatt    420

tcggtgcgta aactcctttt atataagaag ataatgacgg tattatatga ataagcaccg    480

gctaactccg tgccagcagc cgcggtaata cggggggtgc aagcgttact cggaatcact    540

gggcgtaaag agcatgtagg cggattaata agtttgaagt gaaatcctat agcttaacta    600

tagaactgct ttgaaaactg ttgatctaga atgtgggaga ggtagatgga atttctggtg    660

taggggtaaa atccgtagag atcagaagga ataccgattg cgaaggcgat ttactggaac    720

acaattgacg ctgagatgcg aaagcgtggg gagcaaacag gattagatac cctggtagtc    780

cacgccctna acgatgtaca ctagttgttg tgagactnga tcttgcagta atgcagttaa    840

cacattaagt gtaccgcctg gggagtacgg tcgcaagatt aaaactcaaa ggaatagacg    900

gggacccgca caagcggnnn nnnnngtggt ttaattcgan nnnacacgaa gaaccttacc    960

tkgacttgac atagtaagaa ctttctagag atagattggt gtctgcttgc agaaacttat   1020

atacaggtgc tgcacggctg tcgtcagctc gtgtcgtgag atgttgggtt aagtcccgca   1080

acgagcgcaa ccctcgtgtt tagttgctaa cagttcggct gagaactcta aacagactgc   1140

ctacgcaagt aggaggaagg tgaggacgac gtcaagtcat catggccctt acgtccaggg   1200

ctacacacgt gctacaatgg gatatacaaa gagcggcaat acggtgacgt ggagcaaatc   1260

ttataaaata tctcccagtt cggattgtag tctgcaactc gactacatga agttggaatc   1320

gctagtaatc gtagatcagc tatgctacgg tgaatacgtt cccgggtctt gtactcaccg   1380

cccgtcacac catgggagtc gaactcattc gaagcgggga tgctaaagta gctaccttcc   1440

acagtggatt tggcgactgg gg                                             1462
```

<210> SEQ ID NO 21
<211> LENGTH: 1462
<212> TYPE: DNA
<213> ORGANISM: Arcobacter butzleri
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (789)..(789)

```
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (918)..(925)
<223> OTHER INFORMATION: n is a, c, g, or t
<220> FEATURE:
<221> NAME/KEY: misc_feature
<222> LOCATION: (940)..(943)
<223> OTHER INFORMATION: n is a, c, g, or t

<400> SEQUENCE: 21

atggagagtt tgatcctggc tcagagtgaa cgctggcggc gtgcttaaca catgcaagtc     60

gaacgagaac gggctatagc ttgctatagt tgtcagctaa gtggcgcacg ggtgagtaat    120

gtataggtaa tatgcctctt actaagggat aacaaatgga aacgtttgct nataccttat    180

actcctntta aacaaaagtt taaaagggaa agatttattg gtaagagatt agcctgtatt    240

gtatcagtta gttggtgggg taatggctta ccaagactat gacacataac tggtttgaga    300

ggatgatcag tcacactgga actgagacac ggtccagact cctrcgggag gcagcagtgg    360

ggaatattgc acaatggacg aaagtctgat gcagcaacgc cgcgtggagg atgacacatt    420

tcggtgcgta aactcctttt atataagaag ataatgacgg tattatatga ataagcaccg    480

gctaactccg tgccagcagc cgcggtaata cggggggtgc aagcgttact cggaatcact    540

gggcgtaaag agcatgtagg cggattaata agtttgaagt gaaatcctat agcttaacta    600

tagaactgct ttgaaaactg ttgatctaga atgtgggaga ggtagatgga atttctggtg    660

taggggtaaa atccgtagag atcagaagga ataccgattg cgaaggcgat ttactggaac    720

acaattgacg ctgagatgcg aaagcgtggg gagcaaacag gattagatac cctggtagtc    780

cacgccctna acgatgtaca ctagttgttg tgagactnga tcttgcagta atgcagttaa    840

cacattaagt gtaccgcctg gggagtacgg tcgcaagatt aaaactcaaa ggaatagacg    900

gggacccgca caagcggnnn nnnnngtggt ttaattcgan nnnacacgaa gaaccttacc    960

tkgacttgac atagtaagaa ctttctagag atagattggt gtctgcttgc agaaacttat   1020

atacaggtgc tgcacggctg tcgtcagctc gtgtcgtgag atgttgggtt aagtcccgca   1080

acgagcgcaa ccctcgtgtt tagttgctaa cagttcggct gagaactcta aacagactgc   1140

ctacgcaagt aggaggaagg tgaggacgac gtcaagtcat catggccctt acgtccaggg   1200

ctacacacgt gctacaatgg gatatacaaa gagcggcaat acggtgacgt ggagcaaatc   1260

ttataaaata tctcccagtt cggattgtag tctgcaactc gactacatga agttggaatc   1320

gctagtaatc gtagatcagc tatgctacgg tgaatacgtt cccgggtctt gtactcaccg   1380

cccgtcacac catgggagtc gaactcattc gaagcgggga tgctaaagta gctaccttcc   1440

acagtggatt tggcgactgg gg                                            1462


<210> SEQ ID NO 22
<211> LENGTH: 1515
<212> TYPE: DNA
<213> ORGANISM: Arcobacter butzleri

<400> SEQUENCE: 22

atggagagtt tgatcctggc tcagagtgaa cgctggcggc gtgcttaaca catgcaagtc     60

gaacgagaac ggattatagc ttgctataat tgtcagctaa gtggcgcacg ggtgagtaat    120

gtataggtaa tatgcctctt actaagggat aacaattgga aacgattgct aataccttat    180
```

```
attccttttt atcaaaagat aaaaagggaa agatttattg gtaagagatt agcctgtatt    240

gtatcagtta gttggtgggg taatggccta ccaagacgat gacgcataac tggtttgaga    300

ggatgatcag tcacactgga actgagacac ggtccagact cctacgggag gcagcagtgg    360

ggaatattgc acaatggacg aaagtctgat gcagcaacgc cgcgtggagg atgacacatt    420

tcggtgcgta aactcctttt atataagaag ataatgacgg tattatatga ataagcaccg    480

gctaactccg tgccagcagc cgcggtaata cggagggtgc aagcgttact cggaatcact    540

gggcgtaaag agcgtgtagg cggattgata agtttgaagt gaaatcctat agcttaacta    600

tagaactgct ttgaaaactg ttaatctaga atgtgggaga ggtagatgga atttctggtg    660

taggggtaaa atccgtagag atcagaagga ataccgattg cgaaggcgat ctactggaac    720

aatattgacg ctgagacgcg aaagcgtggg gagcaaacag gattagatac cctggtagtc    780

cacgccctaa acgatgtaca ctagttgttg tgaggctcga ccttgcagta atgcagttaa    840

cacattaagt gtaccgcctg gggagtacgg tcgcaagatt aaaactcaaa ggaatagacg    900

gggacccgca caagcggtgg agcatgtggt ttaattcgac gatacacgaa gaaccttacc    960

tggacttgac atagtaagaa tgatttagag atagattagt gtctgcttgc agaaacttgc   1020

atacaggtgc tgcacggctg tcgtcagctc gtgtcgtgag atgttgggtt aagtcccgca   1080

acgagcgcaa ccctcgtcct tagttgctaa cagttcggct gagaactcta aggagactgc   1140

ctacgcaagt aggaggaagg tgaggatgac gtcaagtcat catggccctt acgtccaggg   1200

ctacacacgt gctacaatgg ggtatacaaa gagcagcaat acggtgacgt ggagcaaatc   1260

tcaaaaatgc ctcccagttc ggattgtagt ctgcaactcg actacatgaa gttggaatcg   1320

ctagtaatcg tagatcagct atgctacggt gaatacgttc ccgggtcttg tactcaccgc   1380

ccgtcacacc atgggagttg aactcattcg aagcggggat gctaaagtag ctaccttcca   1440

cagtggattc agcgactggg gtgaagtcgt aacaaggtaa ccgtaggaga acctgcggtt   1500

ggatcacctc ctttc                                                    1515
```

```
<210> SEQ ID NO 23
<211> LENGTH: 1453
<212> TYPE: DNA
<213> ORGANISM: Unknown
<220> FEATURE:
<223> OTHER INFORMATION: Arcobacter species

<400> SEQUENCE: 23

cctggctcag agtgaacgct ggcggcgtgc ttaacacatg caagtcgaac gagaaacggt     60

ctagcttgct agatgcagtc taagtggcgc acgggtgagt aatatatagg taatatgcct    120

cttactaagg gataacagat ggaaacgtct gctaatacct tatatgcctt taggactaaa    180

gtccgcaagg gaaagattta tcggtaagag attagcctgt acagtatcag ttagttggtg    240

aggtaatggc tcaccaagac tatgacactt aactggtttg agaggatgat cagtcacact    300

ggaactgaga cacggtccag actcctacgg gaggcagcag tggggaatat tgcacaatgg    360

acggaagtct gatgcagcaa cgccgcgtgg aggatgacac atttcggtgc gtaaactcct    420

tttatatgag aagataatga cggtatcata tgaataagca ccggctaact ccgtgccagc    480

agccgcggta atacggaggg tgcaagcgtt actcggaatc actgggcgta aagagcgtgt    540

aggcgggttg ataagtttga agtgaaatcc tatagcttaa ctatagaact gctttgaaaa    600

ctgttaacct agaatatggg agaggtagat ggaatttctg gtgtaggggt aaaatccgta    660
```

```
gagatcagaa ggaataccga ttgcgaaggc gatctactgg aacattattg acgctgagac    720
gcgaaagcgt gggtagcaaa caggattaga taccctggta gtccacgccc taaacgatgt    780
acactagttg ttgtgaggct cgaccttgca gtaatgcagt taacacatta agtgtaccgc    840
ctggggagta cggtcgcaag attaaaactc aaaggaatag acggggaccc gcacaagcgg    900
tggagcatgt ggtttaattc gacgatacac gaagaacctt acctggactt gacatagtaa    960
gaactttcta gagatagatt ggtgtctgct tgcagaaact tatatacagg tgctgcacgg   1020
ctgtcgtcag ctcgtgtcgt gagatgttgg gttaagtccc gcaacgagcg caaccctcgt   1080
cattagttgc taacagttcg gctgagaact ctaatgagac tgcctacgta agtaggagga   1140
aggtgaggac gacgtcaagt catcatggcc cttacgtcca gggctacaca cgtgctacaa   1200
tggggtatac aaagagcagc aatacggtga cgtggagcaa atctcaaaaa tatctcccag   1260
ttcggattgt agtctgcaac tcgactacat gaagttggaa tcgctagtaa tcgtagatca   1320
gctatgctac ggtgaatacg ttcccgggtc ttgtactcac cgcccgtcac accatgggag   1380
ttgaactcat tcgaagcggg gatgctaaag tagctacctt ccacagtgga tttagcgact   1440
ggggtgaagt cgt                                                      1453
```

<210> SEQ ID NO 24
<211> LENGTH: 1478
<212> TYPE: DNA
<213> ORGANISM: Unknown
<220> FEATURE:
<223> OTHER INFORMATION: Arcobacter species

<400> SEQUENCE: 24

```
agagtttgat catggctcag agtgaacgct ggcggcgtgc ttaacacatg caagtcgaac     60
gagaaacgta tttagtttac taaatagcag tctaagtggc gcacgggtga gtaatgtata    120
ggtaacatgc ctcttactaa gggataacag atggaaacgt ctgctaatac cttatatgcc    180
tttaatacgg aagtatgcaa gggaaagatt tattggtaag agattggcct gtatggtatc    240
agttagttgg tgaggtaatg gctcaccaag acaatgacac ctaactggtt tgagaggatg    300
atcagtcaca ctggaactga gacacggtcc agactcctac gggaggcagc agtggggaat    360
attgcacaat ggacgaaagt ctgatgcagc aacgccgcgt ggaggatgac acatttcggt    420
gcgtaaactc cttttatagg tcaagataat gacggtagcc tatgaataag cgccggctaa    480
ctccgtgcca gcagccgcgg taatacggag ggcgcaagcg ttactcggaa tcactgggcg    540
taaagagcgt gtaggcggac taataagtca gaagtgaaat ccaatagctt aactattgaa    600
ctgcttttga aactgtttgt ctagagtgtg ggagaggtag atggaatttc tggtgtaggg    660
gtaaaatccg tagatatcag aaggaatacc gattgcgaag gcgatctact ggaacataac    720
tgacgctgag acgcgaaagc gtggggagca aacaggatta gataccctgg tagtccacgc    780
cctaaacgat gtacactagt tgttgccttg ctagacaagg cagtaatgca cctaacggat    840
taagtgtacc gcctggggag tacggtcgca agattaaaac tcaaaggaat agacggggac    900
ccgcacaagc ggtggagcat gtggtttaat tcgacgatac gcgaagaacc ttacctggtc    960
ttgacatagt aagaactttc cagagatgga ttggtgctag cttgctagaa cttacataca   1020
ggtgctgcac ggctgtcgtc agctcgtgtc gtgagatgtt gggttaagtc ccgcaacgag   1080
cgcaaccctc gtgtttagtt gctaacagtt cggctgagaa ctctaaacag actgcctacg   1140
caagtaggag gaaggtgagg acgacgtcaa gtcatcatgg cccttacgac cagggctaca   1200
cacgtgctac aatggggtat acaaagagca gcgatacggt gacgtggagc aaatctataa   1260
```

aatgcctctc agttcggatt gtagtctgca actcgactac atgaagttgg aatcgctagt 1320
aatcgtggat cagcaatgcc acggtgaata cgttcccggg tcttgtactc accgcccgtc 1380
acaccatggg agttgaattc attcgaagcg ggatgctaa agtagctacc ttccacagtg 1440
gatttagcga ctggggtgaa gtcgtaacaa ggtaaccg 1478

<210> SEQ ID NO 25
<211> LENGTH: 1478
<212> TYPE: DNA
<213> ORGANISM: Unknown
<220> FEATURE:
<223> OTHER INFORMATION: Arcobacter species

<400> SEQUENCE: 25
agagtttgat tatggctcag agtgaacgct ggcggcgtgc ttaacacatg caagtcgaac 60
gagaaacgta tttagtttac taaatagcag tctaagtggc gcacgggtga gtaatgtata 120
ggtaacatgc ctcttactaa gggataacag atggaaacgt ctgctaatac cttatatgcc 180
tttaatacgg aagtatgcaa gggaaagatt tattggtaag agattggcct gtatggtatc 240
agttagttgg tgaggtaatg gctcaccaag acaatgacac ctaactggtt tgagaggatg 300
atcagtcaca ctggaactga gacacggtcc agactcctac gggaggcagc agtggggaat 360
attgcacaat ggacgaaagt ctgatgcagc aacgccgcgt ggaggatgac acatttcggt 420
gcgtaaactc cttttatagg tcaagataat gacggtagcc tatgaataag cgccggctaa 480
ctccgtgcca gcagccgcgg taatacggag ggcgcaagcg ttactcggaa tcactgggcg 540
taaagagcgt gtaggcggac taataagtca gaagtgaaat ccaatagctt aactattgaa 600
ctgcttttga aactgtttgt ctagagtgtg ggagaggtag atggaatttc tggtgtaggg 660
gtaaaatccg tagatatcag aaggaatacc gattgcgaag gcgatctact ggaacataac 720
tgacgctgag acgcgaaagc gtggggagca aacaggatta gataccctgg tagtccacgc 780
cctaaacgat gtacactagt tgttgccttg ctagacaagg cagtaatgca cctaacggat 840
taagtgtacc gcctggggag tacggtcgca agattaaaac tcaaaggaat agacggggac 900
ccgcacaagc ggtggagcat gtggtttaat tcgacgatac gcgaagaacc ttacctggtc 960
ttgacatagt aagaactttc cagagatgga ttggtgctag cttgctagaa cttacataca 1020
ggtgctgcac ggctgtcgtc agctcgtgtc gtgagatgtt gggttaagtc ccgcaacgag 1080
cgcaaccctc gtgtttagtt gctaacagtt cggctgagaa ctctaaacag actgcctacg 1140
caagtaggag gaaggtgagg acgacgtcaa gtcatcatgg cccttacgac cagggctaca 1200
cacgtgctac aatggggtat acaaagagca gcgatacggt gacgtggagc aaatctataa 1260
aatgcctctc agttcggatt gtagtctgca actcgactac atgaagttgg aatcgctagt 1320
aatcgtggat cagcaatgcc acggtgaata cgttcccggg tcttgtactc accgcccgtc 1380
acaccatggg agttgaattc attcgaagcg ggatgctaa agtagctacc ttccacagtg 1440
gatttagcga ctggggtgaa gtcgtaacaa ggtaaccg 1478

<210> SEQ ID NO 26
<211> LENGTH: 1431
<212> TYPE: DNA
<213> ORGANISM: Arcobacter sulfidicus

<400> SEQUENCE: 26
gtgaacgctg gcggcgtgct taacacatgc aagtcgaacg agaacggatt aaagcttgct 60

```
ttaattgtca gctaagtggc gcacgggtga gtaatgtata ggtaatgtgc ctaagagaag    120

gggataacag atggaaacgc ctgctaagac cctatatgcc tttagaacaa aagttygcaa    180

gggaaatatt tatagctctt cgatcggcct atattgtatc agtttgttgg tggggtaatg    240

gcctaccaag actatgacgc ataactggtt tgagaggatg atcagtcaca ctggaactga    300

gacacggtcc agactcctac gggaggcagc agtggggaat attgcacaat gggggaaacc    360

ctgatgcagc aacgccgcgt ggaggatgac acatttcggt gcgtaaactc cttttatata    420

agaagaaaat gacggtatta tatgaataag caccggctaa ctccgtgcca gcagccgcgg    480

taatacgggg ggtgcaagcg ttactcggaa tcactgggcg taaagcgcat gtaggcggat    540

agataagttg gaagtgaaat cctatggctt aaccatagaa ctgcttccaa aactgtctat    600

ctagaatatg ggagaggtag atggaatttc tggtgtaggg gtaaaatccg tagagatcag    660

aaggaatacc gattgcgaag gcgatctact ggaacattat tgacgctgag atgcgaaagc    720

gtggggagca aacaggatta gataccctgg tagtccacgc cctaaacgat gtacactagt    780

tgttgcgatg ctagacattg cagtaatgca gttaacacat taagtgtacc gcctggggag    840

tacggtcgca agattaaaac tcaaaggaat agacggggac ccgcacaagc ggtggagcat    900

gtggtttaat tcgacgatac gcgaagaacc ttacctggcc ttgacatacc aagaacttat    960

cagagatgat ttggtgctag cttgctagaa cttggataca ggtgctgcac ggctgtcgtc   1020

agctcgtgtc gtgagatgtt gggttaagtc ccgcaacgag cgcaacccac gtgtttagtt   1080

actaacagtt cggctgagga ctctaaacag actgccttcg caaggaggag gaaggtgtgg   1140

acgacgtcaa gtcatcatgg cccttacggc cagggctaca cacgtgctac aatggggtat   1200

acaaagagcc gcaataccgc gaggtggagc aaatctcata aaatatctcc cagttcggat   1260

agtactctgc aactcgagtg cttgaagttg gaatcgctag taatcgtaaa tcagcaatgt   1320

tacggtgaat acgttcccgg gtcttgtact caccgcccgt cacaccatgg gagttgattt   1380

cattcgaagc ggggatgcta agatagctac cttccacagt ggaattagcg a            1431

<210> SEQ ID NO 27
<211> LENGTH: 1483
<212> TYPE: DNA
<213> ORGANISM: Unknown
<220> FEATURE:
<223> OTHER INFORMATION: Uncultured bacterium clone BP-B88

<400> SEQUENCE: 27

tagagtttga tcctggctca gagtgaacgc tggcggcgtg cttaacacat gcaagtcgaa     60

cgagaaacgg atttagcttg ctaaattgca gtctaagtgg cgcacgggtg agtaatgtat    120

aggtaacatg ccttttagta ggggataaca gatggaaacg tctgctaata ccctatattc    180

cttattagcg taagtgtgta agggaaagat ttattgctaa aagattggcc tatattgtat    240

cagctagttg gtagtgtaat ggactaccaa ggctatgacg cataactggt ttgagaggat    300

gatcagtcac actggaactg agacacggtc cagactccta cgggaggcag cagtggggaa    360

tattgcacaa tgggggaaac cctgatgcag caacgccgcg tggaggatga cacatttcgg    420

tgcgtaaact ccttttataa gagaagataa tgacggtatc ttatgaataa gcaccggcta    480

actccgtgcc agcagccgcg gtaatacgga gggtgcaagc gttactcgga atcactgggc    540

gtaaagagcg tgtaggcgga tttgtaagtt gggagtgaaa gcctatggct caaccataga    600

actgcttcca aaactgcatg tctagagtgt gggagaggta gatggaattt ctggtgtagg    660

ggtaaaatcc gtagagatca gaaggaatac cgattgcgaa ggcgatctac tggaacataa    720
```

```
ctgacgctga gacgcgaaag cgtggggagt aaacaggatt agataccctg gtagtccacg    780

ccctaaacga tgtacactag ttgttgtgag gttcgacctt gcagtaatgc agttaacaca    840

gtaagtgtac cgcctgggga gtacggtcgc aagattaaaa ctcaaaggaa tagacgggga    900

cccgcacaag cggtggagca tgtggtttaa ttcgaagata cgcgaagaac cttacctgga    960

cttgacattg aaagaatcct gtagagatac gggagtgcta gcttgctaga gcttgaaaac   1020

aggtgctgca cggctgtcgt cagctcgtgt cgtgagatgt tgggttaagt cccgcaacga   1080

gcgcaaccca cgtcgttagt tgctaacagt taggctgaga actctaacga gactgccttc   1140

gtaaggagga ggaaggtgtg gacgacgtca agtcatcatg gcccttacgt ccagggctac   1200

acacgtgcta caatggggta tacaaagagc agcaatacgg tgacgtggag caaatctcat   1260

aaaatgcctc ccagttcgga ttgtagtctg caactcgact acatgaagtt ggaatcgcta   1320

gtaatcgtag atcagcattg ctacggtgaa tacgttcccg ggtcttgtac tcaccgcccg   1380

tcacaccatg ggagttgatt tcgccttaag tcaaaatgct aaaatagcta ttgcccacgg   1440

cggaatcagc gactggggtg aagtcgtaac aaggtaaccg taa                     1483
```

```
<210> SEQ ID NO 28
<211> LENGTH: 1279
<212> TYPE: DNA
<213> ORGANISM: Unknown
<220> FEATURE:
<223> OTHER INFORMATION: Oilfield bacterium FWKOB
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t

<400> SEQUENCE: 28
```

```
aacacatgcn agtcgaacga gaaacggatt tagcttgcta aattgcagtc taagtggcgc     60

acgggtgagt aatgtatagg taacatgcct tctactaggg gataacagtt ggaaacgact    120

gctaataccc tatattcctt attagcacaa gtgtgtaagg gaaagattca ttggtagaag    180

attggcctat attgtatcag ctagttggta gtgtaatgga ctaccaaggc tatgacgcat    240

aactggtttg agaggatgat cagtcacact ggaactgaga cacggtccag actcctacgg    300

gaggcagcag tggggaatat tncacaatgg gcgaaagcct gatgcagcaa cgccgcgtgg    360

aggatgacac atttcggtgc gtaaactcct tttatatggg aagataatga cggtaccata    420

tgaataagca ccggctaact ccgtgccagc agccgcggta atacggaggg tgcaagcgtt    480

actcggaatt actgggcgta aagagcgtgt aggcgggtta ataagttgga agtgaaatcc    540

tatggcttaa ccatagaact gcttccaaaa ctgttagcct agagtgtggg agaggtagat    600

ggaatttctg gtgtaggggt aaaatccgta gatatcagaa ggaataccga ttgcgaaggc    660

gatctactgg aacataactg acgctgagac gcgaaagcgt ggggagcaaa caggattaga    720

taccctggta gtccacgccc taaacgatgc acactagttg ttgtgaggct cgaccttgca    780

gtaatgcagt taacacagta agtgtgccgc ctggggagta cggtcgcaag attaaaactc    840

aaaggaatag acggggaccc gcacaagcgg tggagcatgt ggtttaattc gaagatacgc    900

gaagaacctt acctggcctt gacattgata gaatctggta gagatactgg agtgctagct    960

tgctagaact tgaaaacagg tgctgcacgg ctgtcgtcag ctcgtgtcgt gagatgttgg   1020
```

```
gttaagtccc gcaacgagcg caaccctcgt cgttagttgc taacagttag gctgagaact   1080

ctaacgagac tgccttcgta aggaggagga aggtgaggac gacgtcaagt catcatggcc   1140

cttacggcca gggctacaca cgtgctacaa tggggtgtac agaaagctgc aatatcgcga   1200

gatggagcaa atctcaaaaa cacctcccag ttcggattgt tctctgcaac tcgagaacat   1260

gaagttggaa tcgctagta                                                1279


<210> SEQ ID NO 29
<211> LENGTH: 1464
<212> TYPE: DNA
<213> ORGANISM: Sulfurospirillum multivorans

<400> SEQUENCE: 29

agtgaacgct ggcggcgtgc ttaacacatg caagtcgaac ggataaaata agcttgctta     60

ttttgttagt ggcgcacggg tgagtaatat atagctaacc tgccctttag tgggggacaa    120

cagttggaaa cgactgctaa taccccatac tccttcttgt cttaagataa gttgggaaag    180

atttatcgct aaaggatggg gctttattgt atcagctagt tggtggggta atggcctacc    240

aaggctatga cgcatacctg gtctgagagg atgatcaggc acactggaac tgagacacgg    300

tccagactcc tacgggaggc agcagtgggg aatattgcac aatggaggaa actctgatgc    360

agcaacgccg cgtggaggat gacgcatttc ggtgtgtaaa ctccttttat aggggaagat    420

aatgacggta ccctatgaat aagcaccggc taactccgtg ccagcagccg cggtaatacg    480

gagggtgcaa gcgttactcg gaatcactgg gcgtaaagga tgcgtaggct ggaaatcaag    540

tcgagagtga aatccaacgg ctcaaccgtt gaactgctct cgaaactggt tacctagaat    600

atgggagagg tagatggaat tagtggtgta ggggtaaaat ccgtagatat cactaggaat    660

accgattgcg aaggcgatct actggaacat tattgacgct gaggcatgaa agcgtgggga    720

gcaaacagga ttagataccc tggtagtcca cgccctaaac gatgcacact agttgttgcg    780

atgctagtca ttgcagtaat gcacttaaca gattaagtgt gccgcctggg gagtacggtc    840

gcaagattaa aactcaaagg aatagacggg gacccgcaca agcggtggag catgtggttt    900

aattcgaaga tacacgaaga accttacctg gccttgatat cctaagaatc ctgtagagat    960

acgggagtgc tagtttacta gaacttagag acaggtgctg cacggctgtc gtcagctcgt   1020

gtcgtgagat gttgggttaa gtcccgcaac gagcgcaacc ctcgtgatta gttgctaaca   1080

gttcggctga gcactctaat cagactgcct tcgtaaggag gaggaaggtg aggacgacgt   1140

caagtcatca tggcccttat ggccagggct acacacgtgc tacaatggct aggacaaaga   1200

gacgcgatac tgcgaagtgg agcaaatctt aaaacctagt ctcagttcgg attgaagtct   1260

gcaactcgac ttcatgaagc tggaatcgct agtaatcgta gatcagatat gctacggtga   1320

atacgttccc gggtcttgta ctcaccgccc gtcacaccat gggagttgaa ttcacccgaa   1380

gccggaatac taaactagtt accgaccacg gygggttcag cgactggggt gaagtcgtaa   1440

caaggtaacc gtaggagaac ctgc                                          1464


<210> SEQ ID NO 30
<211> LENGTH: 1470
<212> TYPE: DNA
<213> ORGANISM: Unknown
<220> FEATURE:
<223> OTHER INFORMATION: bacterium clone AS077_B63

<400> SEQUENCE: 30

agagtttgat cctggctcag agtgaacgct ggcggcgtgc ttaacacatg caagtcgaac     60
```

```
gatgaagctc tagcttgcta gagtggatta gtggcgcacg ggtgaggaat atatagctaa    120

tgtacccctt agagggggat aacagttgga aacgactgct aataccccat actccttctt    180

gtcataagag aagttgggaa agttttttcg ctaagggatc gggctatacg gtatcagctt    240

gttggtgagg taatggctca ccaaggctat gacgcctaac tggtctgaga ggatgatcag    300

tcacactgga actgagacac ggtccagact cctacgggag gcagcagtgg ggaatattgc    360

acaatggggg aagccctgat gcagcaacgc cgcgtggagg atgacacatt tcggtgcgta    420

aactcctttt atatgggaag ataatgacgg taccatatga ataagcaccg gctaactccg    480

tgccagcagc cgcggtaata cggagggtgc aagcgttact cggactcact gggcgtaaag    540

cgcgcgcagg cggtccctta agttggatgt gaaatcctat ggctcaacca tagaactgca    600

tccaaaactg aggggctaga gtctgggagg ggaagatgga attagtggtg taggggtaaa    660

atccgtagag atcactagga ataccaaaag cgaaggcgat cttctggaac agtactgacg    720

ctgaggcgcg aaagcgtggg gagcaaacag gattagatac cctggtagtc cacgccctaa    780

actatgaatg ttagtcgtcg gggagcttgt cttctcggtg atgcagctaa cgcattaaac    840

attccgcctg gggagtacgg tcgcaagatt aaaactcaaa ggaatagacg ggacccgca     900

caagtggtgg agcatgtggt ttaattcgaa gatacgcaaa gaaccttacc tggccttgac    960

attgatagaa tctgctagag atagtggagt gcccttcggg gagcttgaaa acaggtgctg   1020

cacggctgtc gtcagctcgt gtcgtgagat gttgggttaa gtcccgcaac gagcgcaacc   1080

ctcgtcacta gttactaacg gttcggccga ggactctagt gagactgcct tcgtaaggag   1140

gaggaaggtg aggacgacgt caagtcatca tggcccttac ggccagggcg acacacgtgc   1200

tacaatggga tgtacaatga gacgcaatac cgcgaggtgg agcaaatcta taaagcatct   1260

ctcagttcgg attgtagtct gcaactcgac tacatgaagc tggaatcacc agtaatcgta   1320

gatcagccat gctacggtga atacgttccc gggtcttgta ctcaccgccc gtcacaccat   1380

gggagttgat ttcacccgaa gcggggaagc taaattggct accctccacg gtgggatcag   1440

cgactggggt gaagtcgtaa caaggtaacc                                    1470
```

<210> SEQ ID NO 31
<211> LENGTH: 1277
<212> TYPE: DNA
<213> ORGANISM: Unknown
<220> FEATURE:
<223> OTHER INFORMATION: Thiomicrospira species
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (945)..(946)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (1211)..(1211)
<223> OTHER INFORMATION: n is a, c, g, or t
<220> FEATURE:
<221> NAME/KEY: misc_feature
<222> LOCATION: (1271)..(1271)

<223> OTHER INFORMATION: n is a, c, g, or t

<400> SEQUENCE: 31

```
aacacatgcc agtcgaacgg taacgcaaag tgcttgcact ttggcgacga gtggcgcacg      60
ggtgagtaat atatagttaa tgtaccttca agaccgggat agccattgga aacgntgatt     120
aataccggat acaccttcat accataagat atgaagggaa atgtttttc gcttgaagat      180
cagactatat cccatcagtt tgttggtgag gtaagagctc accaagacta tgacgggtag     240
cgggtttgag aggatgatcc gccacactgg tactgagaca cggaccagac tcctacggga     300
ggcagcagtg aggaatattg cacaatggag gaaactctga tgcagcaacg ccgcgtggag     360
gatgacgcat ttcggtgtgt aaactccttt tatatgtcaa gaaaatgacg gtagcatatg     420
aataagcacc ggctaactcc gtgccagcag ccgcggtaat acggagggtg caagcgttac     480
tcggaatcac tgggcgtaag ggacgcgtag gcgggatatc aagtcaggtg tgaaatccta     540
cagcttaact gtagaactgc acttgaaact ggtaacctag agtatgggag ggggagatgg     600
aattagtggt gtaggggtaa aatccgtaga tatcactagg aatacctaaa gcgaaggcga     660
tctcctggaa cataactgac gctaaggcgt gaaagcgtgg ggagcaaaca ggattagata     720
ccctggtagt ccacgcccta aacgatgaac actagtcgtc gtgatgcttg tcattgcggt     780
gatgcactta acagattaag tgttccgcct ggggagtacg gtcgcaagat taaaactcaa     840
aggaatagac ggggacccgc acaagtggtg gagcatgtgg tttaattcga agatacgcga     900
agaaccttac ctggccttga cattganaga acactgtaga gatanngtng tgcccttcgg     960
ggagcttgaa aacaggtgct gcacggctgt cgtcagctcg tgtcgtgaga tgttgggtta    1020
agtcccgcaa cgagcgcaac cctcgtcctt agttgccagc aggttaagct gggcactcta    1080
aggagactgc cttcgcaagg aggaggaagg tgaggacgac gtcaagtcat catggccctt    1140
acggccaggg ctacacacgt gctacaatgg ggcgtacaga gtgttgcaat accgcgaggt    1200
ggagccaatc ncttaaagcg tctctcagtt cggattggag tctgcaactc gactccatga    1260
agctggaatc nctagta                                                   1277
```

<210> SEQ ID NO 32
<211> LENGTH: 1341
<212> TYPE: DNA
<213> ORGANISM: Escherichia coli

<400> SEQUENCE: 32

```
agtcgaacgg taacaggaag aagcttgctt ctttgctgac gagtggcgga cgggtgagta      60
atgtctggga aactgcctga tggaggggga taactactgg aaacggtagc taataccgca     120
taacgtcgca agaccaaaga gggggacctt cgggcctctt gccatcggat gtgcccagat     180
gggattagct agtaggtggg gtaacggctc acctaggcga cgatccctag ctggtctgag     240
aggatgacca gccacactgg aactgagaca cggtccagac tcctacggga ggcagcagtg     300
gggaatattg cacaatgggc gcaagcctga tgcagccatg ccgcgtgtat gaagaaggcc     360
ttcgggttgt aaagtacttt cagcggggag gaagggagta aagttaatac ctttgctcat     420
tgacgttacc cgcagaagaa gcaccggcta actccgtgcc agcagccgcg gtaatacgga     480
gggtgcaagc gttaatcgga attactgggc gtaaagcgca cgcaggcggt ttgttaagtc     540
agatgtgaaa tccccgggct caacctggga actgcatctg atactggcaa gcttgagtct     600
cgtagagggg ggtagaattc caggtgtagc ggtgaaatgc gtagagatct ggaggaatac     660
cggtggcgaa ggcggccccc tggacgaaga ctgacgctca ggtgcgaaag cgtggggagc     720
```

```
aaacaggatt agataccctg gtagtccacg ccgtaaacga tgtcgacttg gaggttgtgc    780

ccttgaggcg tggcttccgg agctaacgcg ttaagtcgac cgcctgggga gtacggccgc    840

aaggttaaaa ctcaaatgaa ttgacggggg cccgcacaag cggtggagca tgtggtttaa    900

ttcgatgcaa cgcgaagaac cttacctggt cttgacatcc acggaagttt tcagagatga    960

gaatgtgcct tcgggaaccg tgagacaggt gctgcatggc tgtcgtcagc tcgtgttgtg   1020

aaatgttggg ttaagtcccg caacgagcgc aacccttatc ctttgttgcc agcggtccgg   1080

ccgggaactc aaaggagact gccagtgata aactggagga aggtggggat gacgtcaagt   1140

catcatggcc cttacgacca gggctacaca cgtgctacaa tggcgcatac aaagagaagc   1200

gacctcgcga gagcaagcgg acctcataaa gtgcgtcgta gtccggattg gagtctgcaa   1260

ctcgactcca tgaagtcgga atcgctagta atcgtggatc agaatgccac ggtgaatacg   1320

ttcccgggcc ttgtacacac c                                             1341
```

<210> SEQ ID NO 33
<211> LENGTH: 1372
<212> TYPE: DNA
<213> ORGANISM: Unknown
<220> FEATURE:
<223> OTHER INFORMATION: Arcobacter species

<400> SEQUENCE: 33

```
acgggattag cttgctaatc tgtcagctaa gtggcgcacg ggtgagtaat atataggtaa     60

cgtgccttca agagggggat aacagatgga aacgtctgct aaaaccccat atgcctttaa    120

tgcgaaagta tgcaagggaa atatttatag cttgaagatc ggcctgtaca gtatcagata    180

gttggtgagg taatagctca ccaagtcaat gacgcttaac tggtttgaga ggatgatcag    240

tcacactgga actgagacac ggtccagact cctacgggag gcagcagtgg ggaatattgc    300

acaatggggg aaaccctgat gcagcaacgc cgcgtggagg atgacacatt tcggtgcgta    360

aactcctttt atataagaag ataatgacgg tattatatga ataagcaccg gctaactccg    420

tgccagcagc cgcggtaata cggagggtgc aagcgttact cggaatcact gggcgtaaag    480

agcgtgtagg cggatagata agtcagaagt gaaatccaat agcttaacta ttgaactgct    540

tttgaaactg tctatctaga gtatgggaga ggtagatgga atttctggtg taggggtaaa    600

atccgtagag atcagaagga ataccgattg cgaaggcgat ctactggaac ataactgacg    660

ctgagacgcg aaagcgtggg gagcaaacag gattagatac cctggtagtc cacgccctaa    720

acgatgtaca ctagttgttg ctatgctcga catagcagta atgcagttaa cacattaagt    780

gtaccgcctg gggagtacgg tcgcaagatt aaaactcaaa ggaatagacg gggacccgca    840

caagcggtgg agcatgtggt ttaattcgac gatacgcgaa gaaccttacc tggtcttgac    900

atagtaagaa ccatttagag atagatgggt gtctgcttgc agaaacttat atacaggtgc    960

tgcacggctg tcgtcagctc gtgtcgtgag atgttgggtt aagtcccgca acgagcgcaa   1020

ccctcgtcat tagttgctaa cacttcgggt gagaactcta atgagactgc ctacgcaagt   1080

aggaggaagg tgaggacgac gtcaagtcat catggccctt acgaccaggg ctacacacgt   1140

gctacaatgg ggtatacaaa gagcagcgat acagtgatgt ggagcaaatc taaaaaatac   1200

ctcccagttc ggattgtagt ctgcaactcg actacatgaa gttggaatcg ctagtaatcg   1260

tagatcagca atgctacggt gaatacgttc ccgggtcttg tactcaccgc ccgtcacacc   1320

atgggagttg atttcactcg aagcggggat gctaagatag ctaccctcca ca           1372
```

<210> SEQ ID NO 34
<211> LENGTH: 1389
<212> TYPE: DNA
<213> ORGANISM: Unknown
<220> FEATURE:
<223> OTHER INFORMATION: Arcobacter species

<400> SEQUENCE: 34

```
atgcaagtcg aacgagaacg ggattagctt gctaatctgt cagctaagtg gcgcacgggt     60

gagtaatata taggtaacgt gccttcaaga gggggataac agatggaaac gtctgctaaa    120

accccatatg cctttaatgc gaaagtatgc aagggaaata tttatagctt gaagatcggc    180

ctgtacagta tcagatagtt ggtgaggtaa tagctcacca agtcaatgac gcttaactgg    240

tttgagagga tgatcagtca cactggaact gagacacggt ccagactcct acgggaggca    300

gcagtgggga atattgcaca atgggggaaa ccctgatgca gcaacgccgc gtggaggatg    360

acacatttcg gtgcgtaaac tccttttata taagaagata atgacggtat tatatgaata    420

agcaccggct aactccgtgc cagcagccgc ggtaatacgg agggtgcaag cgttactcgg    480

aatcactggg cgtaaagagc gtgtaggcgg atagataagt cagaagtgaa atccaatagc    540

ttaactattg aactgctttt gaaactgtct atctagagta tgggagaggt agatggaatt    600

tctggtgtag gggtaaaatc cgtagagatc agaaggaata ccgattgcga aggcgatcta    660

ctggaacata actgacgctg agacgcgaaa gcgtggggag caaacaggat tagataccct    720

ggtagtccac gccctaaacg atgtacacta gttgttgcca tgctcgacat ggcagtaatg    780

cagttaacac attaagtgta ccgcctgggg agtacggtcg caagattaaa actcaaagga    840

atagacgggg acccgcacaa gcggtggagc atgtggttta attcgacgat acgcgaagaa    900

ccttacctgg tcttgacata gtaagaacca tttagagata gatgggtgtc tgcttgcaga    960

aacttatata caggtgctgc acggctgtcg tcagctcgtg tcgtgagatg ttgggttaag   1020

tcccgcaacg agcgcaaccc tcgtcattag ttgctaacac ttcgggtgag aactctaatg   1080

agactgccta cgcaagtagg aggaaggtga ggacgacgtc aagtcatcat ggcccttacg   1140

accagggcta cacacgtgct acaatggggt atacaaagag cagcgataca gtgatgtgga   1200

gcaaatctaa aaaatacctc ccagttcgga ttgtagtctg caactcgact acatgaagtt   1260

ggaatcgcta gtaatcgtag atcagcaatg ctacggtgaa tacgttcccg ggtcttgtac   1320

tcaccgcccg tcacaccatg ggagttgatt tcactcgaag cggggatgct aagatagcta   1380

ccctccaca                                                           1389
```

<210> SEQ ID NO 35
<211> LENGTH: 937
<212> TYPE: DNA
<213> ORGANISM: Unknown
<220> FEATURE:
<223> OTHER INFORMATION: Arcobacter species

<400> SEQUENCE: 35

```
ccgcggtaat acggagggtg caagcgttac tcggaatcac tgggcgtaaa gagcgtgtag     60

gcggatagat aagtcagaag tgaaatccaa tagcttaact attgaactgc ttttgaaact    120

gtctatctag agtatgggag aggtagatgg aatttctggt gtaggggtaa aatccgtaga    180

gatcagaagg aataccgatt gcgaaggcga tctactggaa cataactgac gctgagacgc    240

gaaagcgtgg ggagcaaaca ggattagata ccctggtagt ccacgcccta aacgatgtac    300

actagttgtt gctatgctcg acatagcagt aatgcagtta acacattaag tgtaccgcct    360
```

```
ggggagtacg gtcgcaagat taaaactcaa aggaatagac ggggacccgc acaagcggtg    420
gagcatgtgg tttaattcga cgatacgcga agaaccttac ctggtcttga catagtaaga    480
accatttaga gatagatggg tgtctgcttg cagaaactta tatacaggtg ctgcacggct    540
gtcgtcagct cgtgtcgtga gatgttgggt taagtcccgc aacgagcgca accctcgtca    600
ttagttgcta acacttcggg tgagaactct aatgagactg cctacgcaag taggaggaag    660
gtgaggacga cgtcaagtca tcatggccct tacgaccagg gctacacacg tgctacaatg    720
gggtatacaa agagcagcga tacagtgatg tggagcaaat ctaaaaaata cctcccagtt    780
cggattgtag tctgcaactc gactacatga agttggaatc gctagtaatc gtagatcagc    840
aatgctacgg tgaatacgtt cccgggtctt gtactcaccg cccgtcacac catgggagtt    900
gatttcactc gaagcgggga tgctaagata gctaccc                             937
```

<210> SEQ ID NO 36
<211> LENGTH: 1381
<212> TYPE: DNA
<213> ORGANISM: Unknown
<220> FEATURE:
<223> OTHER INFORMATION: Arcobacter species

<400> SEQUENCE: 36

```
agtcgaacga gaacgggatt agcttgctaa tctgtcagct aagtggcgca cgggtgagta     60
atatataggt aacgtgcctt caagaggggg ataacagatg gaaacgtctg ctaaaacccc    120
atatgccttt aatacgaaag tatgcaaggg aaatatttat agcttgaaga tcggcctgta    180
cagtatcaga tagttggtga ggtaatagct caccaagtca atgacgctta actggtttga    240
gaggatgatc agtcacactg gaactgagac acggtccaga ctcctacggg aggcagcagt    300
ggggaatatt gcacaatggg ggaaaccctg atgcagcaac gccgcgtgga ggatgacaca    360
tttcggtgcg taaactcctt ttatataaga agataatgac ggtattatat gaataagcac    420
cggctaactc cgtgccagca gccgcggtaa tacggagggt gcaagcgtta ctcggaatca    480
ctgggcgtaa agagcgtgta ggcggataga taagtcagaa gtgaaatcca atakcttaac    540
tattgaactg cctttgaaac tgtctatcta gagtatggga gaggtagatg gaatttctgg    600
tgtaggggta aaatccgtag agatcagaag gaataccgat tgcgaaggcg atctactgga    660
acataactga cgctgagacg cgaaagcgtg grgagcaaac aggattagat accctggtag    720
tccacgccct aaacgatgta cactagttgt tgccatgctc gacatggcag taatgcagtt    780
aacacattaa gtgtaccgcc tggggagtac ggtcgcaaga ttaaaactca aaggaataga    840
cggggacccg cacaagcggt ggagcatgtg gtttaattcg acgatacgcg aagaacctta    900
cctggtcttg acatagtaag aaccatttag agatagatgg gtgtctgctt gcagaaactt    960
atatacaggt gctgcacggc tgtcgtcagc tcgtgtcgtg agatgttggg ttaagtcccg   1020
caacgagcgc aaccctcgtc attagttgct aacacttcgg gtgagaactc taatgagact   1080
gcctacgcaa gtaggaggaa ggtgaggacg acgtcaagtc atcatggccc ttacgaccag   1140
ggctacacac gtgctacaat ggggtataca aagagcagcg atacagtgat gtggagcaaa   1200
tctaaaaaat acctcccagt tcggattgta gtctgcaact cgactacatg aagttggaat   1260
cgctagtaat cgtagatcag caatgctacg gtgaatacgt tcccgggtct tgtactcacc   1320
gcccgtcaca ccatgggagt tgatttcact cgaagcgggg atgctaagat agctaccctc   1380
c                                                                   1381
```

<210> SEQ ID NO 37
<211> LENGTH: 1477
<212> TYPE: DNA
<213> ORGANISM: Unknown
<220> FEATURE:
<223> OTHER INFORMATION: Arcobacter species

<400> SEQUENCE: 37

```
agagtttgat catggctcag agtgaacgct ggcggcgtgc ttaacacatg caagtcgaac     60

gagaacggga ttagcttgct aatctgtcag ctaagtggcg cacgggtgag taatatatag    120

gtaacgtgcc ttcaagaggg ggataacaga tggaaacgtc tgctaagacc ccatatgcct    180

ttaatacaaa agtatgaaag ggaaatattt atagcttgaa gatcggcctg tacagtatca    240

gatagttggt gaggtaatgg ctcaccaagt caatgacgct taactggttt gagaggatga    300

tcagtcacac tggaactgag acacggtcca gactcctacg ggaggcagca gtggggaata    360

ttgcacaatg gggaaaccc tgatgcagca acgccgcgtg gaggatgaca catttcggtg    420

cgtaaactcc ttttatataa gaagataatg acggtattat atgaataagc accggctaac    480

tccgtgccag cagccgcggt aatacggagg gtgcaagcgt tactcggaat cactgggcgt    540

aaagagcgtg taggcggata gataagtcag aagtgaaatc caatagctta actattgaac    600

tgcttttgaa actgtctatc tagagtatgg gagaggtaga tggaatttct ggtgtagggg    660

taaaatccgt agagatcaga aggaataccg attgcgaagg cgatctactg gaacataact    720

gacgctgaga cgcgaaagcg tggggagcaa acaggattag ataccctggt agtccacgcc    780

ctaaacgatg tacactagtt gttgccatgc tcgacatggc agtaatgcag ttaacacatt    840

aagtgtaccg cctggggagt acggtcgcaa gattaaaact caaaggaata gacggggacc    900

cgcacaagcg gtggagcatg tggtttaatt cgacgatacg cgaagaacct tacctggtct    960

tgacatagta agaaccattt agagatagat gggtgtctgc ttgcagaaac ttatatacag   1020

gtgctgcacg gctgtcgtca gctcgtgtcg tgagatgttg ggttaagtcc cgcaacgagc   1080

gcaaccctcg tcattagttg ctaacacttc gggtgagaac tctaatgaga ctgcctacgc   1140

aagtaggagg aaggtgagga cgacgtcaag tcatcatggc ccttacgacc agggctacac   1200

acgtgctaca atggggtata caaagagcag cgatacagtg atgtggagca aatctaaaaa   1260

atacctccca gttcggattg tagtctgcaa ctcgactaca tgaagttgga atcgctagta   1320

atcgtagatc agcaatgcta cggtgaatac gttcccgggt cttgtactca ccgcccgtca   1380

caccatggga gttgatttca ctcgaagcgg ggatgctaag atagctaccc tccacagtgg   1440

aattagcgac tggggtgaag tcgtaacaag gtaaccg                            1477
```

<210> SEQ ID NO 38
<211> LENGTH: 1384
<212> TYPE: DNA
<213> ORGANISM: Unknown
<220> FEATURE:
<223> OTHER INFORMATION: Arcobacter species

<400> SEQUENCE: 38

```
agtcgaacga gaacgggatt agcttgctaa tctgtcagct gagtggcgca cgggtgagta     60

atatataggt aacgtgcctt caagaggggg ataacagatg gaaacgtctg ctaaaacccc    120

atatgccttt aatacgaaag tatgcaaggg aaatatttat agcttgaaga tcggcctgta    180

cagtatcaga tagttggtga ggtaatagct caccaagtca atgacgctta actggtttga    240

gaggatgatc agtcacactg gaactgagac acggtccaga ctcctacggg aggcagcagt    300
```

```
ggggaatatt gcacaatggg ggaaaccctg atgcagcaac gccgcgtgga ggatgacaca    360

tttcggtgcg taaactcctt ttatataaga agataatgac ggtattatat gaataagcac    420

cggctaactc cgtgccagca gccgcggtaa tacggagggt gcaagcgtta ctcggaatca    480

ctgggcgtaa agagcgtgta ggcggataga taagtcagaa gtgaaatcca atagcttaac    540

tattgaactg cttttgaaac tgtctatcta gagtatggga gaggtagatg gaatttctgg    600

tgtaggggta aaatccgtag agatcagaag gaataccgat tgcgaaggcg atctactgga    660

acataactga cgctgagacg cgaaagcgtg gggagcaaac aggattagat accctggtag    720

tccacgccct aaacgatgta cactagttgt tgccatgctc gacatggcag taatgcagtt    780

aacacattaa gtgtaccgcc tggggagtac ggtcgcaaga ttaaaactca aaggaataga    840

cggggacccg cacaagcggt ggagcatgtg gtttaattcg acgatacgcg aagaacctta    900

cctggtcttg acatagtaag aaccatttag agatagatgg gtgtctgctt gcagaaactt    960

atatacaggt gctgcacggc tgtcgtcagc tcgtgtcgtg agatgttggg ttaagtcccg   1020

caacgagcgc aaccctcgtc attagttgct aacacttcgg gtgagaactc taatgagact   1080

gcctacgcaa gtaggaggaa ggtgaggacg acgtcaagtc atcatggccc ttacgaccag   1140

ggctacacac gtgctacaat ggggtataca aagagcagcg atacagtgat gtggagcaaa   1200

tctaaaaaat acctcccagt tcggattgta gtctgcaact cgactacatg aagttggaat   1260

cgctagtaat cgtagatcag caatgctacg gtgaatacgt tcccgggtct tgtactcacc   1320

gcccgtcaca ccatgggagt tgatttcact cgaagcgggg atgctaagat agctaccctc   1380

caca                                                                1384
```

<210> SEQ ID NO 39
<211> LENGTH: 1477
<212> TYPE: DNA
<213> ORGANISM: Unknown
<220> FEATURE:
<223> OTHER INFORMATION: Arcobacter species

<400> SEQUENCE: 39

```
agagtttgat cctggctcag agtgaacgct ggcggcgtgc ttaacacatg caagtcgaac     60

gagaacggga ttagcttgct aatctgtcag ctaagtggcg cacgggtgag taatatatag    120

gtaacgtgcc ttcaagaggg ggataacaga tggaaacgtc tgctaaaacc ccatatgcct    180

ttaatacgaa agtatgcaag ggaaatattt atagcttgaa gatcggcctg tacagtatca    240

gatagttggt gaggtaatag ctcaccaagt caatgacgct taactggttt gagaggatga    300

tcagtcacac tggaactgag acacggtcca gactcctacg ggaggcagca gtggggaata    360

ttgcacaatg gggggaaacc tgatgcagca acgccgcgtg gaggatgaca catttcggtg    420

cgtaaactcc ttttatataa gaagataatg acggtattat atgaataagc accggctaac    480

tccgtgccag cagccgcggt aatacggagg gtgcaagcgt tactcggaat cactgggcgt    540

aaagagcgtg taggcggata gataagtcag aagtgaaatc caatagctta actattgaac    600

tgcttttgaa actgtctatc tagagtatgg gagaggtaga tggaatttct ggtgtagggg    660

taaaatccgt agagatcaga aggaataccg attgcgaagg cgatctactg gaacataact    720

gacgctgaga cgcgaaagcg tggggagcaa acaggattag ataccctggt agtccacgcc    780

ctaaacgatg tacactagtt gttgctatgc tcgacatagc agtaatgcag ttaacacatt    840

aagtgtaccg cctggggagt acggtcgcaa gattaaaact caaaggaata gacggggacc    900
```

```
cgcacaagcg gtggagcatg tggtttaatt cgacgatacg cgaagaacct tacctggtct    960

tgacatagta agaaccattt agagatagat gggtgtctgc ttgcagaaac ttatatacag   1020

gtgctgcacg gctgtcgtca gctcgtgtcg tgagatgttg ggttaagtcc cgcaacgagc   1080

gcaaccctcg tcattagttg ctaacacttc gggtgagaac tctaatgaga ctgcctacgc   1140

aagtaggagg aaggtgagga cgacgtcaag tcatcatggc ccttacgacc agggctacac   1200

acgtgctaca atggggtata caaagagcag cgatacagtg atgtggagca aatctaaaaa   1260

atacctccca gttcggattg tagtctgcaa ctcgactaca tgaagttgga atcgctagta   1320

atcgtagatc agcaatgcta cggtgaatac gttcccgggt cttgtactca ccgcccgtca   1380

caccatggga gttgatttca ctcgaagcgg ggatgctaag atagctaccc tccacagtgg   1440

aattagcgac tggggtgaag tcgtaacaag gtaaccg                            1477
```

```
<210> SEQ ID NO 40
<211> LENGTH: 1481
<212> TYPE: DNA
<213> ORGANISM: Unknown
<220> FEATURE:
<223> OTHER INFORMATION: Arcobacter species
<220> FEATURE:
<221> NAME/KEY: variation
<222> LOCATION: (72)..(72)
<223> OTHER INFORMATION: Base A72 exists in >1 reference sequence; may
      be absent in others
<220> FEATURE:
<221> NAME/KEY: variation
<222> LOCATION: (83)..(83)
<223> OTHER INFORMATION: Base T83 exists in >1 reference sequence; may
      be absent in others
<220> FEATURE:
<221> NAME/KEY: variation
<222> LOCATION: (208)..(208)
<223> OTHER INFORMATION: Base C208 was found in only 1 reference
      sequence and was absent in others
<220> FEATURE:
<221> NAME/KEY: variation
<222> LOCATION: (1318)..(1318)
<223> OTHER INFORMATION: Base G1318 was found in only 1 reference
      sequences and was absent in others

<400> SEQUENCE: 40

agtcgagcgg ymtggctcag agtgaacgct ggcggcgtgc ttaacacatg caagtcgaac     60

gagaacggrw tatagcttgc tatatctgtc agctaagtgg cgcacgggtg agtaatrtat    120

aggtaacrtg ccyyyaagag ggggataaca gwtggaaacg wctgctaadr ycyyatatgc    180

ctttaatrcd aaagtatgma agggaaacky ttwakwgctt rrrgatyggc ctgtaywgta    240

tcagmtagtt ggtgrggtaa kagcyyacca agdcaatgac gcwtaactgg tttgagagga    300

tgatcagtca cactggaact gagacacggt ccagactcct acgggaggca gcagtgggga    360

atattgcaca atgggggraa ccctgatgca gcaacgccgc gtggaggatg acacatttcg    420

gtgcgtaaac tccttttata targaagawa atgacggtay tatatgaata agcrccggct    480

aactccgtgc cagcagccgc ggtaatacgg agggygcaag cgttactcgg aatcactggg    540

cgtaaagagc gtgtaggcgg atmrataagt yagragtgaa atccwatrgc tyaacyatwg    600

aactgcttyt raaactgtyw atctagagta tgggagaggt agatggaatt tctggtgtag    660

gggtaaaatc cgtagagatc agaaggaata ccgattgcga aggcgatcta ctggaacata    720

actgacgctg agacgcgaaa gcgtggggag caaacaggat tagataccct ggtagtccac    780

gccctaaacg atgtacacta gttgttgcya trctcgacat dgcagtaatg cagttaacac    840

attaagtgta ccgcctgggg agtacggtcg caagrttaaa actcaaagga atagacgggg    900
```

```
acccgcacaa gcggtggagy atgtggttta attcgacgat acgcgaagaa ccttacctgg    960

tcttgacata gwaagaayhm tyyagagata gatgggtgyy wgcttgcwrr arcttwyata   1020

caggtgctgc acggctgtcg tcagctcgtg tcgtgagatg ttgggttaag tcccgcaacg   1080

agcgcaaccc tcgtcrttag ttgctaasac twcggstgag aactctaayg agactgcctr   1140

sgcaasyagg aggaaggtga ggacgacgtc aagtcatcat ggcccttacg accagggcta   1200

cacacgtgct acaatggggt atacaaagag cagcratacr gygaygtgga gcraatctha   1260

aaaatryctc ycagttcgga ttgtagtctg caactcgact acrtgaagtt ggaatcggct   1320

agtaatcgta gatcagcway gctacggtga atacgttccc gggtcttgta cwcaccgccc   1380

gtcacaccat gggagttgaw ttcacycgaa gcrgggatgy taarrtarct accytcchca   1440

gtggawtyag cgactggggt gaagtcgtaa carggtaacc g                       1481
```

```
<210> SEQ ID NO 41
<211> LENGTH: 1480
<212> TYPE: DNA
<213> ORGANISM: Unknown
<220> FEATURE:
<223> OTHER INFORMATION: Arcobacter species
<220> FEATURE:
<221> NAME/KEY: variation
<222> LOCATION: (208)..(208)
<223> OTHER INFORMATION: Base W208 was found in only 1 reference
      sequence; may be absent in most others.
<220> FEATURE:
<221> NAME/KEY: misc_feature
<222> LOCATION: (979)..(979)
<223> OTHER INFORMATION: n is a, c, g, or t

<400> SEQUENCE: 41
```

```
agtcgagcgg ymtggctcag agtgaacgct ggcggcgtgc ttaacacatg caagtcgaac     60

gagaacggrt tawagcttgc twwwwytgtc agctaagtgg cgcacgggtg agtaatrtat    120

aggtaacmtg ccctmdagar rrgrataaca gwtggaaacg wctgctaadr ycyyatatgc    180

ctttaakach yawgtytgca agggaaawca tttatggctc taggatkggy ctgtayrgta    240

tcagmtmgtt ggtgaggtaa tggctcacca agrcaatgac rcytaactgg tttgagagga    300

tgatcagtca cactggaact gagacacggt ccagactcct acgggaggca gcagtgggga    360

atattgcaca atggacgaaa gtctgatgca gcaacgccgc gtggaggatg acacatttcg    420

gtgcgtaaac tccttttata taggaagata atgacggtay yatatgaata agcaccggct    480

aactccgtgc cagcagccgc ggtaatacgg agggtgcaag cgttactcgg aatcactggg    540

cgtaaagagc rtgtaggcgg gtawwtaagt ydgaagtgaa atccwatrgc tyaacyatwg    600

aactgcttcc aaaactgkta acctagaatr tgggagaggt agatggaatt tctggtgtag    660

gggtaaaatc cgtagakatc agaaggaata ccgattgcga aggcgatcta ctggaacayw    720

attgacgctg agaygcgaaa gcgtggggag caaacaggat tagataccct ggtagtccac    780

gccctaaacg atgyacacta gttgttgtga ggctagacct tgcagtaatg cagttaacac    840

attaagtgtr ccgcctgggg agtacggtcg caagattaaa actcaaagga atagacgggg    900

acccgcacaa gcggtggagc atgtggttta attcgacgat acrcgaagaa ccttacctgg    960

wcttgacata gwaagaacnt whyagagata gatgggtgyy wgcttgcwrr arctwwyata   1020

caggtgctgc acggctgtcg tcagctcgtg tcgtgagatg ttgggttaag tcccgcaacg   1080

agcgcaaccc tcgtsdttag ttgctaagac ttcggctgag aactctaahg agactgcctr   1140

sgcaasyagg aggaaggtga ggacgacgtc aagtcatcat ggcccttacg wccagggcta   1200
```

```
cacacgtgct acaatggggt atacaaagag cagcratacr gygaygtgga gcraatctya   1260

aaaatryctc ccagttcgga ttgwagtctg caactcgact rcytgaagtt ggaatcgcta   1320

gtaatcgtag atcagcwawg ctacggtgaa tacgttcccg ggtcttgtac tcaccgcccg   1380

tcacaccatg ggagttgawy tcactcgaag crgrgatgct aaartagcta ccytccacag   1440

tggawtyagc gactggggtg aagtcgtaac arggtaaccg                         1480
```

```
<210> SEQ ID NO 42
<211> LENGTH: 1481
<212> TYPE: DNA
<213> ORGANISM: Unknown
<220> FEATURE:
<223> OTHER INFORMATION: Arcobacter species
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: variation
<222> LOCATION: (1260)..(1260)
<223> OTHER INFORMATION: Base T1260 was found in 1 reference sequence
      and may be absent in others
<220> FEATURE:
<221> NAME/KEY: variation
<222> LOCATION: (1346)..(1346)
<223> OTHER INFORMATION: Base A1346 was found in 1 reference sequence;
      may be absent in others.

<400> SEQUENCE: 42
```

```
agtcgagcgg ymtggctcag agtgaacgct ggcggcgtgc ttaacacatg caagtcgaac     60

gagaacggat tatagcttgc tatarttgtc agctaagtgg cgcacgggtg agtaatrtat    120

aggtaacttg cctcttacta agggataaca rwtggaaacg wytgctaaca ccccataytc    180

cwyyyyawch waagwtrrwa agggaaagat ttattggtaa gagattagcc tgtattgtat    240

cagttagttg gtggggtaat ggcctaccaa gacdatgacg cataactggt ttgagaggat    300

gatcagtcac actggaactg agacacggtc cagactccta cgggaggcag cagtggggaa    360

tattgcacaa tggacgaaag tctgatgcag caacgccgcg tggaggatga cacatttcgg    420

tgcgtaaact ccttttatat aagaagataa tgacggtatt atatgaataa gcaccggcta    480

actccgtgcc agcagccgcg gtaatacggr gggtgcaagc gttactcgga atcactgggc    540

gtaaagagcr tgtaggcgga ttrataagtt tgaagtgaaa tcctatagct taactataga    600

actgctttga aaactgttaa cctagaatgt gggagaggta gatggaattt ctggtgtagg    660

ggtaaaatcc gtagagatca gaaggaatac cgattgcgaa ggcgatctac tggaacahta    720

ttgacgctga gaygcgaaag cgtggggagc aaacaggatt agataccctg gtagtccacg    780

ccctaaacga tgtacactag ttgttgtgag rctygayctt gcagtaatgc agttaacaca    840

ttaagtgtac cgcctgggga gtacggtcgc aagattaaaa ctcaaaggaa tagacgggga    900

cccgcacaag cggtggagca tgtggtttaa ttcgacgata cacgaagaac cttacctgga    960

cttgacatag taagaaykwt ywagagatag atgggtgtct gcttgcagaa acttryatac   1020

aggtgctgca cggctgtcgt cagctcgtgt cgtgagatgt tgggttaagt cccgcaacga   1080

gcgcaaccct cgtcbttagt tgctaagact tcggctgaga actctaarga gactgcctrs   1140

gcaagtagga ggaaggtgag gaygacgtca agtcatcatg gcccttacgt ccagggctac   1200

acacgtgcta caatgggrta tacarwgagc ngcratacgg tgacgtggag caaatctyat   1260

aaaatryctc ccagttcgga ttgtagtctg caactcgact acatgaagtt ggaatcgcta   1320
```

```
gtaatcgtag atcagctatg ctacgagtga atacgttccc gggtcttgta ctcaccgccc   1380

gtcacaccat gggagttgaa ctcactcgaa gcggggatgc taaartagct accttccaca   1440

gtggattyag cgactggggt gaagtcgtaa caaggtaacc g                      1481


<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43

cggttacctt gttacgactt                                                20


<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44

agagtttgat ymtggctcag                                                20


<210> SEQ ID NO 45
<211> LENGTH: 16
<212> TYPE: DNA
<213> ORGANISM: Artificial Sequence
<220> FEATURE:
<223> OTHER INFORMATION: Primer

<400> SEQUENCE: 45

aacagctatg accatg                                                    16


<210> SEQ ID NO 46
<211> LENGTH: 17
<212> TYPE: DNA
<213> ORGANISM: Artificial Sequence
<220> FEATURE:
<223> OTHER INFORMATION: Primer

<400> SEQUENCE: 46

gtaaaacgac ggccagt                                                   17


<210> SEQ ID NO 47
<211> LENGTH: 34
<212> TYPE: DNA
<213> ORGANISM: Shewanella oneidensis

<400> SEQUENCE: 47

gcatacgccc tacgggggaa agagggggac tttc                                34


<210> SEQ ID NO 48
<211> LENGTH: 34
<212> TYPE: DNA
<213> ORGANISM: artificial sequence
<220> FEATURE:
<223> OTHER INFORMATION: Shewanella 16S rDNA degenerate signature
      sequence with variable positions in region 2
<220> FEATURE:
<221> NAME/KEY: misc_feature
<222> LOCATION: (22)..(24)
<223> OTHER INFORMATION: n=a or g
<220> FEATURE:
<221> NAME/KEY: misc_feature
<222> LOCATION: (29)..(29)
```

<223> OTHER INFORMATION: n=a or c
<220> FEATURE:
<221> NAME/KEY: misc_feature
<222> LOCATION: (30)..(30)
<223> OTHER INFORMATION: n=a,,c, g, or t
<220> FEATURE:
<221> NAME/KEY: misc_feature
<222> LOCATION: (30)..(30)
<223> OTHER INFORMATION: n=a, c, g, or t
<220> FEATURE:
<221> NAME/KEY: misc_feature
<222> LOCATION: (31)..(32)
<223> OTHER INFORMATION: n=t or c
<220> FEATURE:
<221> NAME/KEY: misc_feature
<222> LOCATION: (34)..(34)
<223> OTHER INFORMATION: n=a or c

<400> SEQUENCE: 48
gcatacgccc tacgggggaa annngggggnn nntn 34

<210> SEQ ID NO 49
<211> LENGTH: 41
<212> TYPE: DNA
<213> ORGANISM: Shewanella oneidensis

<400> SEQUENCE: 49
tcggagtttg gtgtcttgaa cactgggctc tcaagctaac g 41

<210> SEQ ID NO 50
<211> LENGTH: 41
<212> TYPE: DNA
<213> ORGANISM: artificial sequence
<220> FEATURE:
<223> OTHER INFORMATION: Shewanella 16S rDNA degenerate signature sequence with variable positions in region 5
<220> FEATURE:
<221> NAME/KEY: misc_feature
<222> LOCATION: (6)..(6)
<223> OTHER INFORMATION: n=a or g
<220> FEATURE:
<221> NAME/KEY: misc_feature
<222> LOCATION: (13)..(13)
<223> OTHER INFORMATION: n=a , c or g
<220> FEATURE:
<221> NAME/KEY: misc_feature
<222> LOCATION: (14)..(14)
<223> OTHER INFORMATION: n=a , c or t
<220> FEATURE:
<221> NAME/KEY: misc_feature
<222> LOCATION: (18)..(19)
<223> OTHER INFORMATION: n=a or g
<220> FEATURE:
<221> NAME/KEY: misc_feature
<222> LOCATION: (27)..(27)
<223> OTHER INFORMATION: n=g or t
<220> FEATURE:
<221> NAME/KEY: misc_feature
<222> LOCATION: (28)..(28)
<223> OTHER INFORMATION: n=t or c
<220> FEATURE:
<221> NAME/KEY: misc_feature
<222> LOCATION: (30)..(31)
<223> OTHER INFORMATION: n=t or c
<220> FEATURE:
<221> NAME/KEY: misc_feature
<222> LOCATION: (32)..(32)
<223> OTHER INFORMATION: n=a or c

<400> SEQUENCE: 50
tcggantttg gtnncttnna cactggnntn nnaagctaac g 41

<210> SEQ ID NO 51

<211> LENGTH: 96
<212> TYPE: DNA
<213> ORGANISM: Shewanella oneidensis

<400> SEQUENCE: 51
acaatggcga gtacagaggg ttgcaaagcc gcgaggtgga gctaatctca caaagctcgt 60
cgtagtccgg attggagtct gcaactcgac tccatg 96

<210> SEQ ID NO 52
<211> LENGTH: 96
<212> TYPE: DNA
<213> ORGANISM: artificial sequence
<220> FEATURE:
<223> OTHER INFORMATION: Shewanella 16S rDNA degenerate signature
sequence with variable positions in region 8
<220> FEATURE:
<221> NAME/KEY: misc_feature
<222> LOCATION: (8)..(8)
<223> OTHER INFORMATION: n=c, g, or t
<220> FEATURE:
<221> NAME/KEY: misc_feature
<222> LOCATION: (9)..(9)
<223> OTHER INFORMATION: n=a, c, or g
<220> FEATURE:
<221> NAME/KEY: misc_feature
<222> LOCATION: (10)..(11)
<223> OTHER INFORMATION: n=a, g, or t
<220> FEATURE:
<221> NAME/KEY: misc_feature
<222> LOCATION: (25)..(25)
<223> OTHER INFORMATION: n=a or g
<220> FEATURE:
<221> NAME/KEY: misc_feature
<222> LOCATION: (33)..(33)
<223> OTHER INFORMATION: n=a or g
<220> FEATURE:
<221> NAME/KEY: misc_feature
<222> LOCATION: (38)..(38)
<223> OTHER INFORMATION: n=g or c
<220> FEATURE:
<221> NAME/KEY: misc_feature
<222> LOCATION: (39)..(39)
<223> OTHER INFORMATION: n=a, g, or t
<220> FEATURE:
<221> NAME/KEY: misc_feature
<222> LOCATION: (48)..(48)
<223> OTHER INFORMATION: n=t or c
<220> FEATURE:
<221> NAME/KEY: misc_feature
<222> LOCATION: (51)..(51)
<223> OTHER INFORMATION: n=c, g, or t
<220> FEATURE:
<221> NAME/KEY: misc_feature
<222> LOCATION: (56)..(56)
<223> OTHER INFORMATION: n=c, g, or t
<220> FEATURE:
<221> NAME/KEY: misc_feature
<222> LOCATION: (57)..(57)
<223> OTHER INFORMATION: n=a, c, or t
<220> FEATURE:
<221> NAME/KEY: misc_feature
<222> LOCATION: (58)..(58)
<223> OTHER INFORMATION: n=c, g, or t
<220> FEATURE:
<221> NAME/KEY: misc_feature
<222> LOCATION: (73)..(73)
<223> OTHER INFORMATION: n=t or c
<220> FEATURE:
<221> NAME/KEY: misc_feature -continued

```
<222> LOCATION: (94)..(94)
<223> OTHER INFORMATION: n=a or g

<400> SEQUENCE: 52

acaatggnnn ntacagaggg ttgcnaagcc gcnaggtnna gctaatcnca naaagnnngt     60

cgtagtccgg atnggagtct gcaactcgac tccntg                               96
```

METHODS, STRAINS, AND COMPOSITIONS USEFUL FOR MICROBIALLY ENHANCED OIL RECOVERY: *ARCOBACTER* CLADE 1

This application claims the benefit of U.S. Provisional Application 61/408,739, filed Nov. 1, 2010 and is incorporated by reference in its entirety.

FIELD OF THE INVENTION

This disclosure relates to the field of environmental microbiology and modification of crude oil well properties using microorganisms. More specifically, methods for improving oil recovery from an underground reservoir are presented and new microorganisms are identified that can be used for oil recovery.

BACKGROUND OF THE INVENTION

During recovery of oil from oil reservoirs, typically only a minor portion of the original oil in the oil-bearing strata is recovered by primary recovery methods which use only the natural forces present in an oil reservoir. To improve oil recovery, a variety of supplemental recovery techniques such as water flooding, which involves injection of water through well bores into the oil reservoir, have been used. As water moves into the reservoir from an injection well and moves through the reservoir strata, it displaces oil to one or more production wells where the oil is recovered. One problem commonly encountered with water flooding operations is poor sweep efficiency of injection water. Poor sweep efficiency occurs when water preferentially channels through highly permeable zones of the oil reservoir as it travels from the injection well(s) to the production well(s), thus bypassing less permeable oil-bearing strata. Oil in the less permeable zones is thus not recovered. Poor sweep efficiency may also be due to differences in the mobility of the water versus that of the oil.

Microorganisms have been used to enhance oil recovery from subterranean formations using various processes which may improve sweep efficiency and/or oil release. For example, viable microorganisms may be injected into an oil reservoir where they may grow and adhere to the surfaces of pores and channels in the rock or sand matrices in the permeable zones to reduce water channeling, and thereby target injection water flow towards less permeable oil-bearing strata. Processes for promoting growth of indigenous microbes by injecting nutrient solutions into subterranean formations are disclosed in U.S. Pat. No. 4,558,739 and U.S. Pat. No. 5,083,611. Injection of microorganisms isolated from oil recovery sites into subterranean formations along with nutrient solutions has been disclosed, including for *Pseudomonas putida* and *Klebsiella pneumoniae* (U.S. Pat. No. 4,800,959), for a *Bacillus* strain or *Pseudomonas* strain I-2 (ATCC 30304) isolated from tap water (U.S. Pat. No. 4,558,739), and for *Pseudomonas putida, Pseudomonas aeruginosa, Corynebacterium lepus, Mycobacterium rhodochrous*, and *Mycobacterium vaccae* (U.S. Pat. No. 5,163,510). Injection of isolated microorganisms and a surfactant is disclosed in U.S. Pat. No. 5,174,378.

Additional useful microbial strains and methods for enhancing oil recovery are needed to further improve the recovery of oil from oil reservoirs.

SUMMARY OF THE INVENTION

The invention relates to methods for enhancing oil recovery from an oil reservoir, as well as to isolated microorganisms and compositions that may be used to enhance oil recovery.

Accordingly, the invention provides a method for enhancing oil recovery from an oil reservoir comprising:

a) providing a composition comprising:
   i) at least one strain of *Arcobacter* belonging to *Arcobacter* clade 1; and
   ii) a minimal growth medium comprising at least one electron acceptor;
b) providing an oil reservoir;
c) inoculating the oil reservoir with the composition of (a) such that the *Arcobacter* containing composition populates and grows in the oil reservoir; and
d) recovering oil from the oil reservoir;

wherein growth of the *Arcobacter* in the oil reservoir enhances oil recovery.

In one embodiment, the strain of *Arcobacter* belonging to *Arcobacter* clade 1 comprises the 16S rDNA degenerate consensus sequence of SEQ ID NO:40.

In another embodiment, the strain of *Arcobacter* belonging to *Arcobacter* clade 1 comprises a 16S rDNA sequence having at least about 97% sequence identity to a sequence selected from the group consisting of SEQ ID NOs: 1, 2, 3, 4, 5, 6, 7, 8, and 39.

In yet another embodiment, the invention provides an isolated microorganism of a strain selected from the group consisting of 97AE3-3 (ATCC No. PTA-11410) and 97AE3-12 (ATCC No. PTA-11409).

In yet another embodiment, the invention provides an oil recovery enhancing composition comprising:

a) at least one isolated strain of *Arcobacter* comprising a partial 16S rDNA sequence selected from the group consisting of SEQ ID NOs; 1, 33, 34, 35, 36, 37, and 38;
b) one or more electron acceptors; and
c) at least one carbon source.

BRIEF DESCRIPTION OF FIGURES AND SEQUENCES

The invention can be more fully understood from the following detailed description, the Figures, and the accompanying sequence descriptions, which form a part of this application.

FIG. 3A-D shows an alignment of 16S rDNA sequences for *Arcobacter* clade 1 dominant consensus, *Arcobacter* clade 1 degenerate consensus, strain 97AE3-12, *Arcobacter* clade 2 degenerate consensus, and *Arcobacter* clade 3 degenerate consensus.

Figure 4:
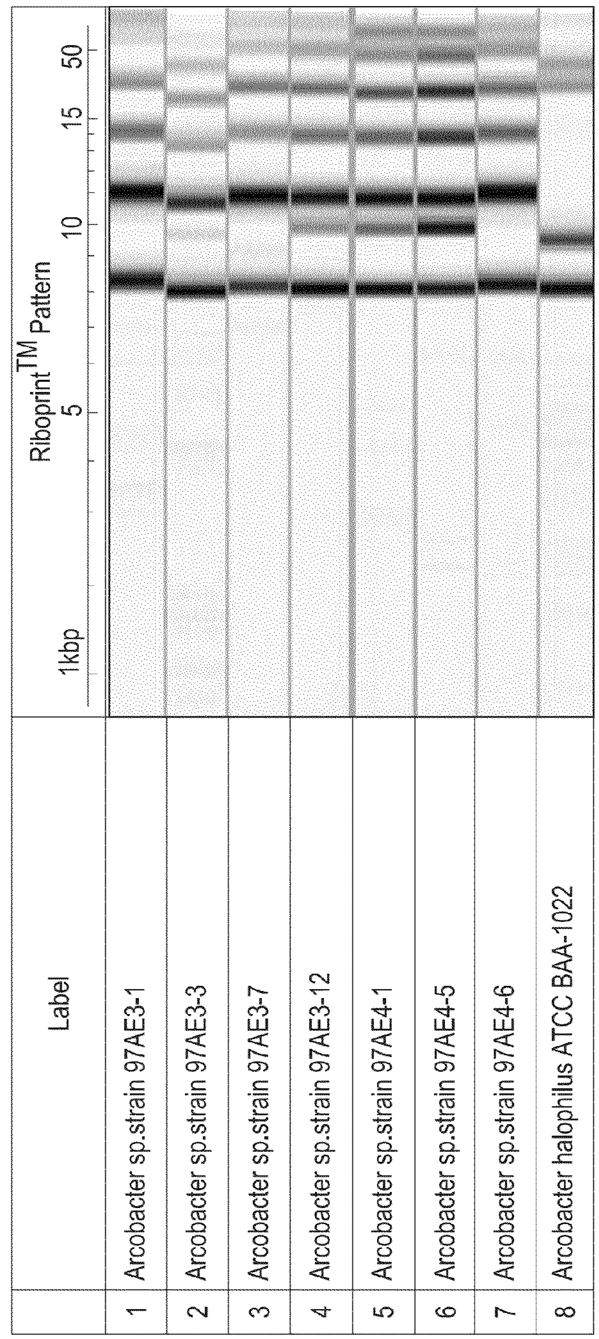

FIG. 4 shows a Riboprinter® analysis of various *Arcobactor* sp strains.

FIG. 5 shows dominate and degenerate signature sequences for *Shewanella* species in rDNA variable regions 2 (A), 5 (B), and 8 (C). The variable positions are underlined. Alternative nucleotides for each variable position designation are given in the legend.

Figure 6:
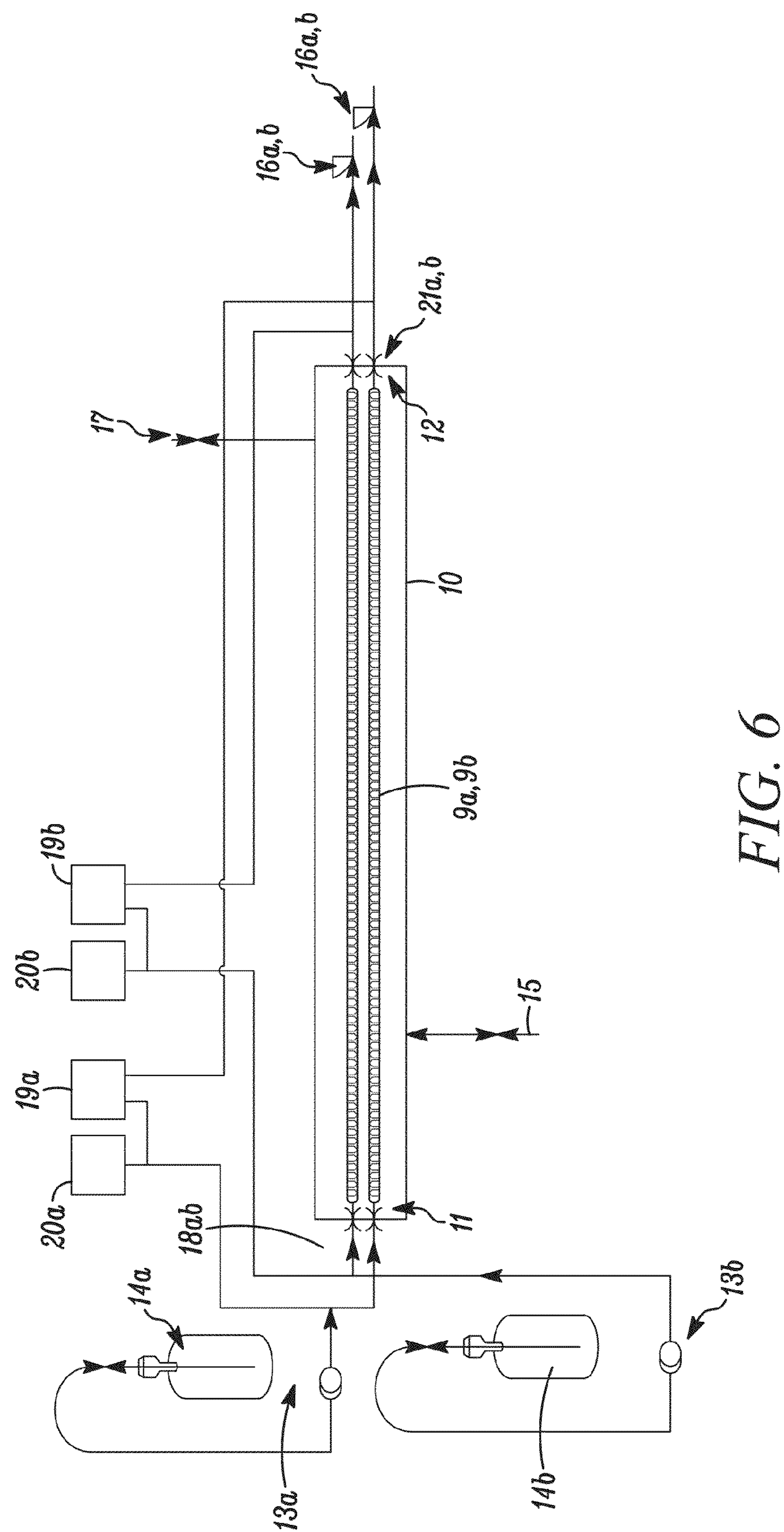
Figure 7:
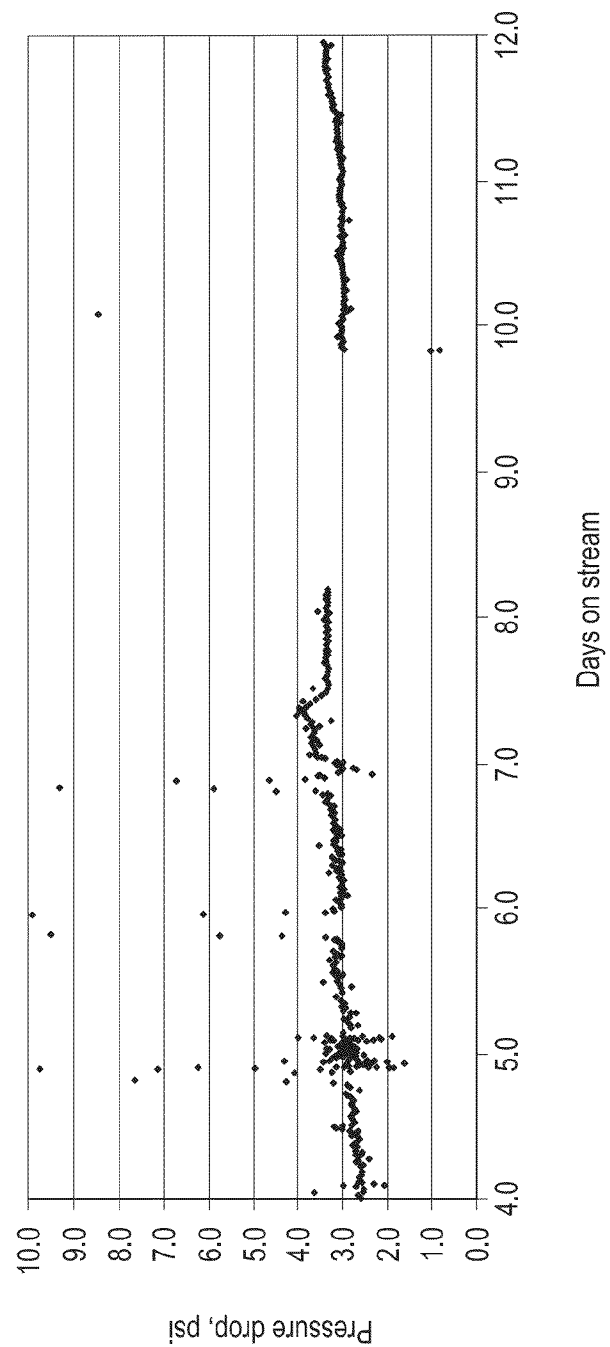

FIG. 6 shows a schematic diagram of the slim tube experimental set up used to measure plugging of permeable sand packs FIG. 7 shows a graph of the pressure drop across a non-inoculated slim tube.

Figure 8:
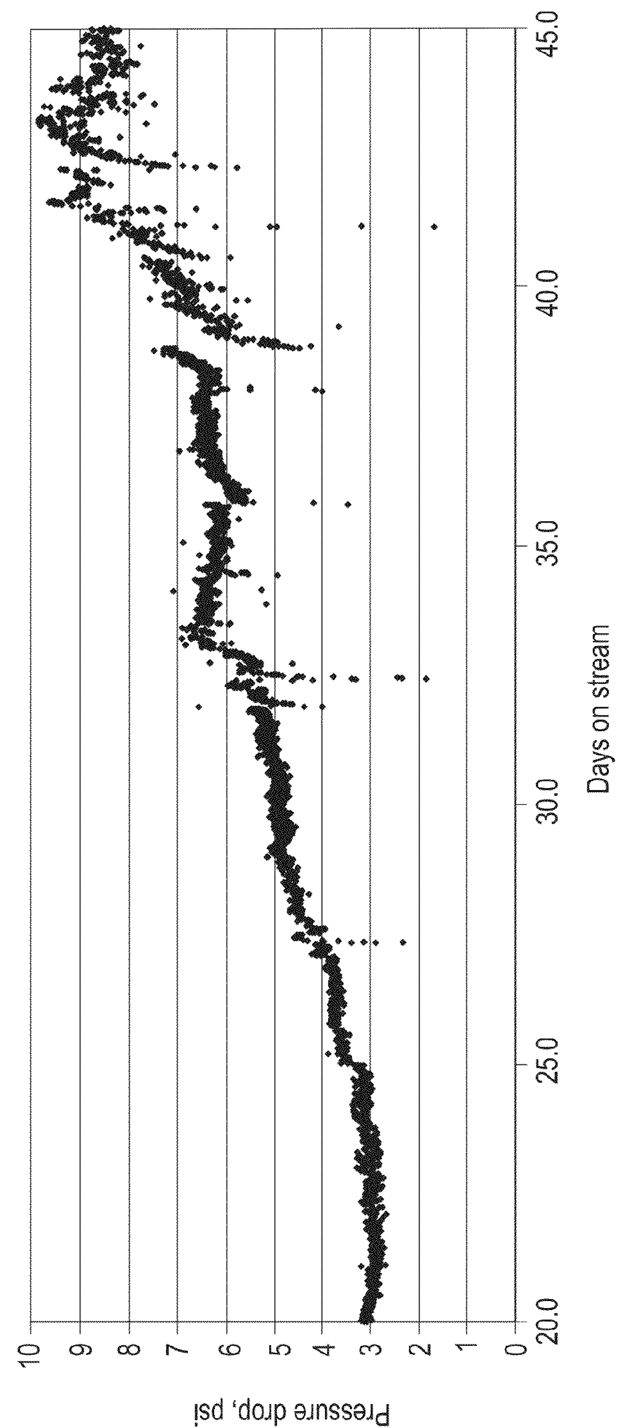

FIG. 8 shows a graph of the pressure drop across a slim tube that was inoculated with *Arcobacter* sp 97AE3-12 (ATCC NO: PTA-11409) and then batch fed periodically.

Figure 9:
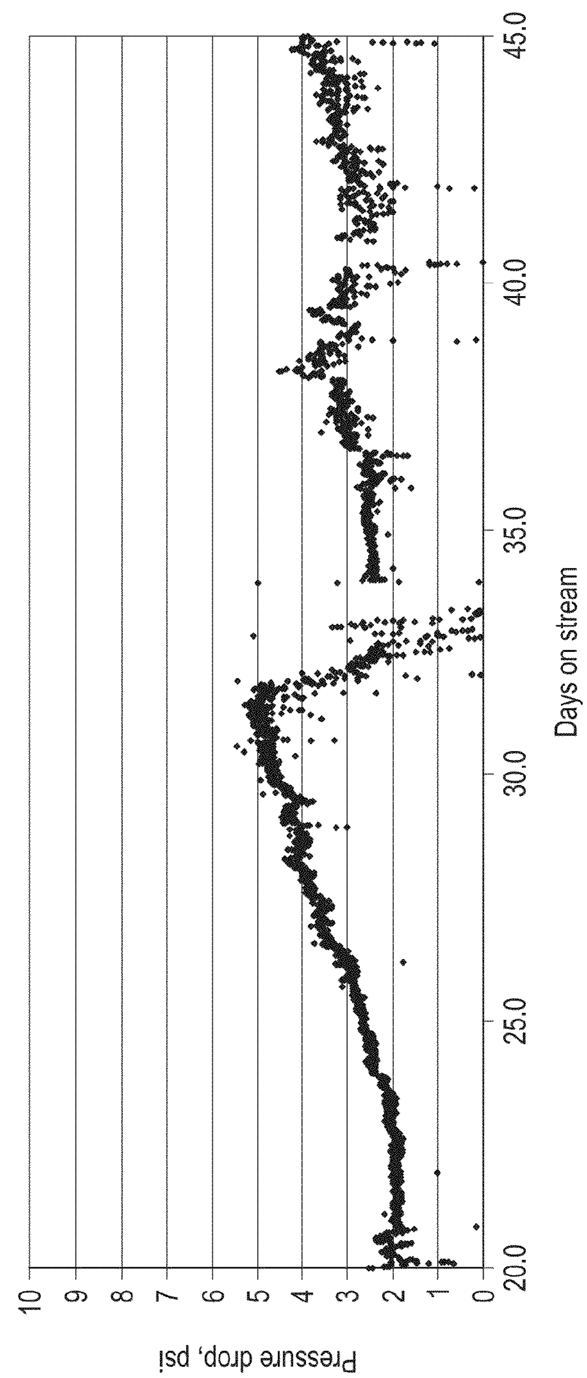

FIG. 9 shows a graph of the pressure drop across a slim tube that was inoculated with *Arcobacter* sp 97AE3-12 (ATCC NO: PTA-11409) and then continuously fed.

The following sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions. The symbols and format used for nucleotide and amino acid sequence data comply with the rules set forth in 37 C.F.R. §1.822.

TABLE 1

16S rDNA seqs of *Arcobacter* strains including coordinates 8 to 1511 in the *E. coli* 16S rDNA sequence.

| Species | Strain | Identification | SEQ ID NO |
|---|---|---|---|
| *Arcobacter* sp | strain 97AE3-12 | Isolate[#] | 1 |
| *Arcobacter* sp. | Solar Lake isolate | isolate | 2 |
| *Arcobacter* sp. | clone YJQ-18 | clone* | 3 |
| *Arcobacter marinus* | CL-S1, JCM 15502; | Type strain | 4 |
| *Arcobacter* sp. | clone EB27.1 | clone | 5 |
| *Arcobacter halophilus* | LA31BT | Type strain | 6 |
| *Arcobacter molluscorum* | F98-3 T | Type strain | 7 |
| *Arcobacter mytili* | F2075T, | Type strain | 8 |
| *Arcobacter nitrofigilis* | CCUC 15893 | Type strain | 9 |
| *Arcobacter defluvii* | SW28-11T | Type strain | 10 |
| *Arcobacter* sp. | R-28314 1 | isolate | 11 |
| *Arcobacter* sp | KT0913 | isolate | 12 |
| *Arcobacter* sp | BSs20195 | isolate | 13 |
| *Arcobacter* sp | clone A3b2 | clone | 14 |
| *Arcobacter nitrofigilis* | DSM 7299T | Type strain | 15 |
| *Arcobacter nitrofigilis* | F2176 | isolate | 16 |
| *Arcobacter cryaerophilus* | CCUG 17082T | Type strain | 17 |
| *Arcobacter cibarius* | LMG 21996T | Type strain | 18 |
| *Arcobacter thereius* | 6695-3 | Type strain | 19 |
| *Arcobacter skirrowi* | CCUG 10374T | Type strain | 20 |
| *Arcobacter butzlerii* | CCUG 10373T | Type strain | 21 |
| *Arcobacter butzlerii* | RM4018 | isolate | 22 |
| *Arcobacter* sp | R-28214 | isolate | 23 |
| *Arcobacter* sp. | clone PL-7C7 | clone | 24 |
| *Arcobacter* sp. | clone PL-8B1 | clone | 25 |
| *Arcobacter sulfidicus* | 162154 | isolate | 26 |
| Uncultured bacterium | clone BP-B88 | clone | 27 |
| Oilfield bacterium | FWKO B | isolate | 28 |
| *Sulfurospirillum multivorans* | Strain K, DSM 12446T | Type strain | 29 |
| Uncultured bacterium | clone AS077_B63 | clone | 30 |
| *Thiomicrospira* sp | Strain CVO | isolate | 31 |

[#]An isolate is a colony isolated from a sample

*A clone contains a PCR amplified fragment generated from bacterial DNA isolated from a sample, which is sequenced to determine the make up of a population SEQ ID NO:32 is a partial *E. coli* 16S rDNA sequence used in alignments of *Arcobacter* 16S rDNA sequences.

SEQ ID NO:33 is a partial 16S rDNA sequence from *Arcobacter* sp. 97AE3-1.

SEQ ID NO:34 is a partial 16S rDNA sequence from *Arcobacter* sp. 97AE3-3.

SEQ ID NO:35 is a partial 16S rDNA sequence from *Arcobacter* sp. 97AE3-7.

SEQ ID NO:36 is a partial 16S rDNA sequence from *Arcobacter* sp. 97AE4-1.

SEQ ID NO:37 is a partial 16S rDNA sequence from *Arcobacter* sp. 97AE4-5.

SEQ ID NO:38 is a partial 16S rDNA sequence from *Arcobacter* sp. 97AE4-6.

SEQ ID NO:39 is a dominant consensus sequence for *Arcobacter* sp. clade 1 16S rDNA.

SEQ ID NO:40 is a degenerate consensus sequence for *Arcobacter* sp. clade 1 16S rDNA.

SEQ ID NO:41 is a degenerate consensus sequence for *Arcobacter* sp. clade 2 16S rDNA.

SEQ ID NO:42 is a degenerate consensus sequence for *Arcobacter* sp. clade 3 16S rDNA.

SEQ ID NOs:43-46 are primers 1492R, 8F, M13 Reverse, and M13 Forward, respectively.

SEQ ID NO:47 is the *Shewanella* dominant signature sequence for the 16S rDNA variable region 2.

SEQ ID NO:48 is the *Shewanella* degenerate signature sequence for the 16S rDNA variable region 2.

SEQ ID NO:49 is the *Shewanella* dominant signature sequence for the 16S rDNA variable region 5.

SEQ ID NO:50 is the *Shewanella* degenerate signature sequence for the 16S rDNA variable region 5.

SEQ ID NO:51 is the *Shewanella* dominant signature sequence for the 16S rDNA variable region 8.

SEQ ID NO:52 is the *Shewanella* degenerate signature sequence for the 16S rDNA variable region 8.

Applicants made the following biological deposits under the terms of the Budapest Treaty on the International Recognition of the Deposit of Microorganisms for the Purposes of Patent Procedure:

TABLE 2

Information on deposited strains

| Depositor Identification Reference | International Depository Designation | Date of Deposit |
|---|---|---|
| *Arcobacter* sp 97AE3-3 | ATCC No. PTA-11410 | Oct. 14, 2010 |
| *Arcobacter* sp 97AE3-12 | ATCC No. PTA-11409 | Oct. 14, 2010 |

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The invention relates to methods for enhancing oil recovery from an oil reservoir by inoculating an oil reservoir with a strain of *Arcobacter* that by molecular phylogenetic analysis of the 16S rDNA sequence belongs to *Arcobacter* clade 1 (defined herein), and a minimal growth medium that supports growth of said *Arcobacter* under denitrifying conditions in the subterranean location. Growth of said *Arcobacter* in the oil reservoir may form biofilms that plug more permeable zones in sand or sandstone layers thereby rerouting water towards less permeable, more oil rich areas. Sweep efficiency is thereby enhanced, leading to increased oil recovery.

In addition, the invention relates to previously unknown microorganisms isolated from water samples obtained from an oil reservoir and compositions containing any of these microorganisms, or other *Arcobacter* of clade 1, which are useful in oil recovery methods. Improving oil recovery using the described methods and microorganisms would increase the output of active oil wells.

The following definitions are provided for the special terms and abbreviations used in this application:

The term "PCR" refers to Polymerase chain reaction.

The term "dNTPs" refers to Deoxyribonucleotide triphosphates.

The term "ASTM" refers to the American Society for Testing and Materials.

The abbreviation "NCBI" refers to the National Center for Biotechnology Information.

The abbreviation "BSL" refers to Biosafety Level.

The abbreviation "RNA" refers to ribonucleic acid.

The abbreviation "DNA" refers to deoxyribonucleic acid.

The abbreviation "ATCC" refers to American Type Culture Collection International Depository, Manassas, Va., USA. "ATCC No." refers to the accession number to cultures on deposit with ATCC.

The abbreviation "CCUG" refers to the Culture Collection of the University of Göteborg, Sweden, which is a collection of microorganisms.

The abbreviation "DSM" or "DSMZ" refers to Deutsche Sammlung von Mikroorganismen and Zellkulturen GmbH which is a German collection of microorganisms and cell cultures (Braunschweig, Germany).

The terms "oil well", "oil reservoir", and "oil-bearing stratum" may be used herein interchangeably and refer to a subterranean or sub sea-bed formation from which oil may be recovered. The formation is generally a body of rocks and soil having sufficient porosity and permeability to store and transmit oil.

The term "well bore" refers to a channel from the surface to an oil-bearing stratum with enough size to allow for the pumping of fluids either from the surface into the oil-bearing stratum (injection well) or from the oil-bearing stratum to the surface (production well).

The terms "denitrifying" and "denitrification" mean reducing nitrate for use in respiratory energy generation.

The term "sweep efficiency" refers to the fraction of an oil-bearing stratum that has seen fluid or water passing through it to move oil to production wells. One problem that can be encountered with waterflooding operations is the relatively poor sweep efficiency of the water, i.e., the water can channel through certain portions of a reservoir as it travels from injection well(s) to production well(s), thereby bypassing other portions of the reservoir. Poor sweep efficiency may be due, for example, to differences in the mobility of the water versus that of the oil, and permeability variations within the reservoir which encourage flow through some portions of the reservoir and not others.

The term "pure culture" means a culture derived from a single cell isolate of a microbial species. The pure cultures specifically referred to herein include those that are publicly available in a depository, and those identified herein.

The term "biofilm" means a film or "biomass layer" of microorganisms. Biofilms are often embedded in extracellular polymers, which adhere to surfaces submerged in, or subjected to, aquatic environments. Biofilms consist of a matrix of a compact mass of microorganisms with structural heterogeneity, which may have genetic diversity, complex community interactions, and an extracellular matrix of polymeric substances.

The term "plugging biofilm" means a biofilm that is able to alter the permeability of a porous material, and thus retard the movement of a fluid through a porous material that is associated with the biofilm.

The term "simple nitrates" and "simple nitrites" refer to nitrate ($NO_3^-$) and nitrite ($NO_2^-$), respectively, as they occur in ionic salts such as potassium nitrate, sodium nitrate, and sodium nitrite.

The term "injection water" refers to fluid injected into oil reservoirs for secondary oil recovery. Injection water may be supplied from any suitable source, and may include, for example, sea water, brine, production water, water recovered from an underground aquifer, including those aquifers in contact with the oil, or surface water from a stream, river, pond or lake. As is known in the art, it may be necessary to remove particulate matter including dust, bits of rock or sand and corrosion by-products such as rust from the water prior to injection into the one or more well bores. Methods to remove such particulate matter include filtration, sedimentation and centrifugation.

The term "production water" means water recovered from production fluids extracted from an oil reservoir. The production fluids contain both water used in secondary oil recovery and crude oil produced from the oil reservoir.

The term "inoculating an oil well" means injecting one or more microorganisms or microbial populations or a consortium into an oil well or oil reservoir such that microorganisms are delivered to the well or reservoir without loss of viability.

The term "phylogenetic typing", "phylogenetic mapping", or "phylogenetic classification" may be used interchangeably herein and refer to a form of classification in which microorganisms are grouped according to their evolutionary genetic lineage. Phylogenetic typing herein is of strains of microorganisms isolated from environmental samples and is based on 16S ribosomal RNA (rRNA) encoding gene (rDNA) sequences.

The term "hypervariable regions" as used herein refers to sequence regions in the 16S rRNA gene where the nucleotide sequence is highly variable. In most microbes the 16S rDNA sequence consists of nine hypervariable regions that demonstrate considerable sequence diversity among different bacterial genera and species and can be used for genus and species identification The term "signature sequences" as used herein refers to specific nucleotides at specific 16S rRNA encoding gene (rDNA) positions (signature positions), which usually occur within the hypervariable regions, that are distinguishing for microorganisms at different levels. At the signature positions, nucleotides that distinguish between species may be one or more specific base substitutions, insertions or deletions. When taken together, the signature sequences of 16S rDNA are useful for describing microbes at the species, strain or isolate level and can be used in the identification of a microbe.

The term "degeneracy or degenerate base position" refers to the case where more than one nucleotide (A, G, C, or T(U)) is possible at a particular position in a DNA or RNA sequence. A position is a "two-fold degenerate" site if only two of four possible nucleotides may be at that position. A position is a "three-fold degenerate" site if three of four possible nucleotides may be at that position. A position is a "four-fold degenerate" site if all four nucleotides may be at that position.

The term "degenerate signature sequence" refers to a signature sequence that may have one or more possible degenerate base positions in the signature sequence.

The term "phylogenetics" refers to the field of biology that deals with identifying and understanding evolutionary relationships between organisms, and in particular molecular phylogenetics uses DNA sequence homologies in this analysis. In particular, similarities or differences in 16S rDNA sequences, including signature sequences, identified using similarity algorithms serves to define phylogenetic relationships.

The term "phylogenetic tree" refers to a branched diagram depicting evolutionary relationships among organisms. The phylogenetic tree herein is based on DNA sequence homologies of 16S rDNAs, including of signature sequences in the 16S rDNA, and shows relationships of the present strains to related strains and species.

The term "phylogenetic clade" or "clade" refers to a branch in a phylogenetic tree. A clade includes all of the related organisms that are located on the branch, based on the chosen branch point.

The term "genomovar" is used to describe a sub-species classification which is used when a group of strains of a species are differentiable by DNA sequence, but are phenotypically indistinguishable. Genomovars are defined and identified by DNA-DNA hybridization and/or by 16S rDNA signature sequences. This terminology has been used to describe *Pseudomonas stutzeri* by Bennasar et al. ((1996) Int. J. of Syst. Bacteriol. 46:200-205).

The term "ribotyping" means fingerprinting of genomic DNA restriction fragments that contain all or part of the genes coding for the 16S and 23S ribosomal RNAs. Ribotyping is performed using the DuPont RiboPrinter® system.

The term "RiboPrint™" refers to the unique genomic fingerprint of a specific microbial isolate or strain, generated using the DuPont RiboPrinter® system.

The term "type strain" refers the reference strain for a particular species whose description is used to define and characterize a particular species.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215, 403-410,1990), DNASTAR (DNASTAR, Inc., Madison, Wis.), and the FASTA program incorporating the Smith-Waterman algorithm (Pearson, W. R., *Comput. Methods Genome Res.*, Proc. Int. Symp, Meeting Date 1992, 111-120, Eds: Suhai, Sandor, Plenum Publishing, New York, N.Y., 1994). Within the context of this application, it will be understood that, where sequence analysis software is used for analysis, the results of the analysis will be based on the "default values" of the program referenced, unless otherwise specified. As used herein "default values" will mean any set of values or parameters which originally load with the software when first initialized.

The term "electron acceptor" refers to a compound that receives or accepts an electron(s) during cellular respiration. Microorganisms obtain energy to grow by transferring electrons from an "electron donor" to an electron acceptor. During this process, the electron acceptor is reduced and the electron donor is oxidized. Examples of electron acceptors include oxygen, nitrate, fumarate, iron (III), manganese (IV), sulfate and carbon dioxide. Sugars, low molecular weight organic acids, carbohydrates, fatty acids, hydrogen and crude oil or its components such as petroleum hydrocarbons or polycyclic aromatic hydrocarbons are examples of compounds that can act as electron donors.

"Darcy" is a unit of permeability. A medium with a permeability of 1 darcy permits a flow of 1 $cm^3/s$ of a fluid with viscosity 1 cP (1 mPa·s) under a pressure gradient of 1 atm/cm acting across an area of 1 $cm^2$. A millidarcy (mD) is equal to 0.001 darcy.

Isolated Microorganisms

Microorganisms capable of growth under anaerobic conditions in the presence of nitrate, fumarate or the ferric ion (Fe (III)) as an electron acceptor and lactate as a carbon source were isolated from production and injection waters of Well #2 that is located in the Wainwright field in the province of Alberta, Canada. Well #2 has a salinity of about 65 parts per thousand (ppt) in both production and injection waters, which is about twice the salinity of seawater.

Isolated microorganisms were characterized by analysis of their 16S ribosomal DNA (rDNA) sequences and by fingerprinting of their genomic DNA restriction fragments that contain all or part of the genes coding for the 16S and 23S ribosomal RNAs (rRNAs; ribotyping). Isolated strains 97AE3-12, 97AE 3-3, 97AE3-1, 97AE 4-6, 97AE 4-5, 97AE 3-7, and 97AE 4-1 were identified as new strains belonging to the genus *Arcobacter*. RiboPrint™ patterns for these strains were distinct from the closely related strain *Arcobacter halophilus* (ATCC BAA-1022), which has over 96% sequence identity with strain 97AE3-12 in the 16S rDNA (SEQ ID NOs:6 and 1, respectively). The RiboPrint™ patterns (FIG. 4) indicate that the newly isolated strains form 3 groupings: 1) 97AE3-12, 97AE4-1, and 97AE4-5; 2) 97AE3-3 and 97AE4-6; and 3) 97AE3-7 and 97AE3-1. The strains 97AE3-12 and 97AE 3-3 were deposited herewith under the Budapest Treaty as ATCC #PTA-11409 and ATCC #PTA-11410, respectively.

Figure 1:
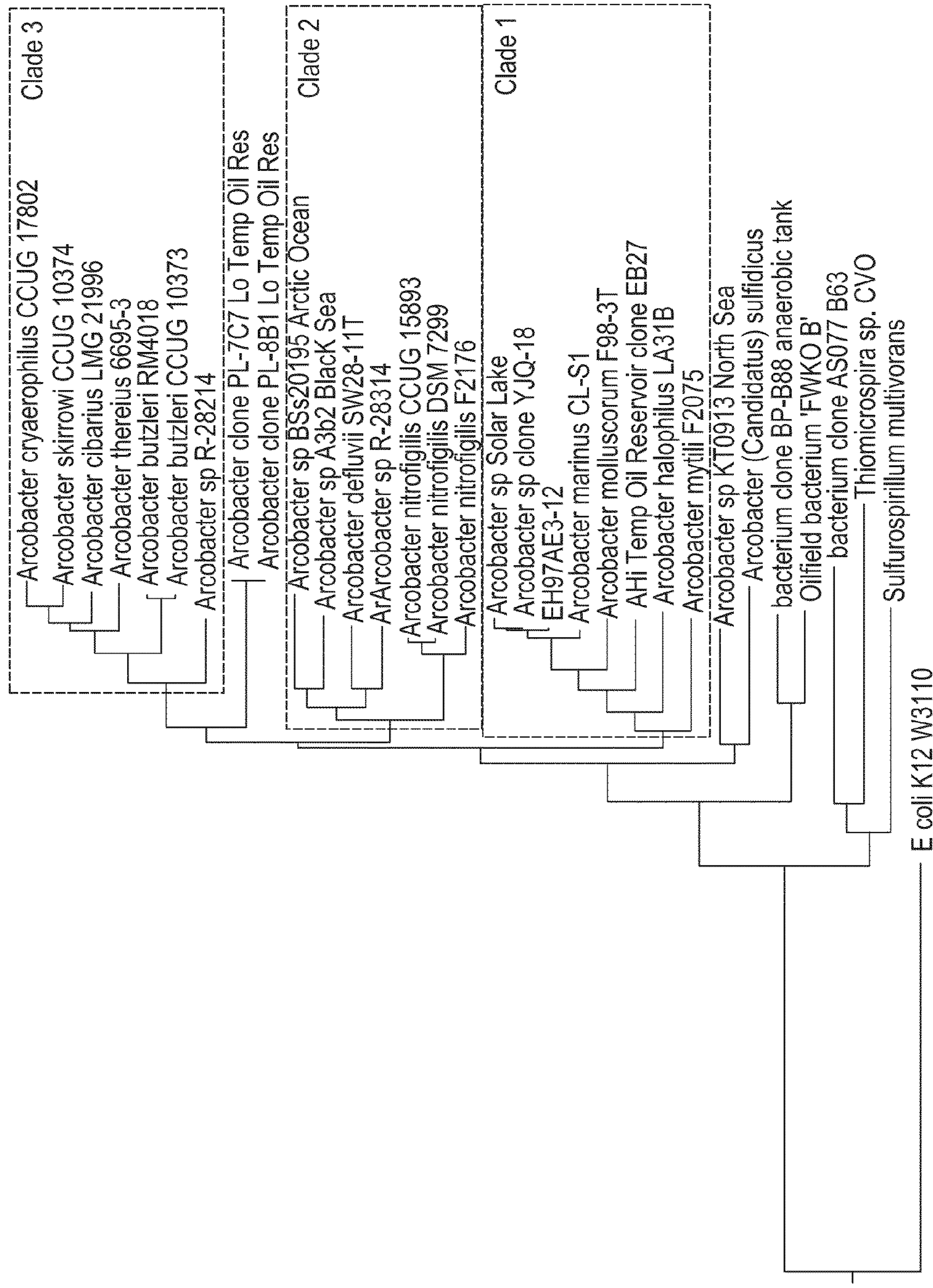
FIG. 1 shows a molecular phylogenetic tree for *Arcobacter* species and related bacteria based on 16S rRNA gene sequences (rDNA), separating the described *Arcobacter* spp. into at least three phylogenetic clades.

Further, the strains were characterized as belonging to *Arcobacter* clade 1 as determined by molecular phylogenetic analysis of 16S rDNA sequences described in Example 2 herein. The phylogenetic tree produced by the analysis is shown in FIG. 1, with the newly isolated strains represented by strain 97AE3-12. The phylogenetic tree shows that three clades, or groupings, are formed of known *Arcobacter* species, which are boxed in the figure. Clade 3 includes pathogenic strains such as *Arcobacter butzleri* and *Arcobacter cryaerophilus*, which are classified as BSL2. Clade 2 includes *Arcobacter nitrofigilis*. Clade 1 includes the known species *Arcobacter marinas, Arcobacter halophilus, Arcobacter molluscorum* and *Arcobacter mytili*. Any strain of *Arcobacter* that belongs to clade 1 may be used in the present method. Clade 1 includes the strains listed above, as well as any strains that belong to the same clade that these strains belong to when analyzed by molecular phylogenetics using 16S rDNA sequences as described herein.

Strains of *Arcobacter* clade 1, which are strains of the present method, may be defined further as strains with rDNA sequences having at least about 97%, 98%, or 99% sequence identity to the 16S rDNA sequences of any of those strains shown in clade 1 in FIG. 1: *Arcobacter* sp Solar lake (SEQ ID NO:2), *Arcobacter* sp YJQ-18 (uncultured clone; SEQ ID NO:3), *Arcobacter marinus* (SEQ ID NO:4), H temp Oil reservoir clone EB27 (SEQ ID NO:5), *Arcobacter halophilus* (SEQ ID NO:6), and *Arcobacter mytili* (SEQ ID NO:8). In addition, strains of the present method include those with rDNA sequences having at least about 97%, 98%, or 99% sequence identity to the 16S rDNA sequence of *Arcobacter molluscorum* F98-3T (SEQ ID NO:7), which also belongs to clade 1. The 16S rDNA sequences of strains from different clades in FIG. 1 have sequence identities of less than 96%.

Figure 2:
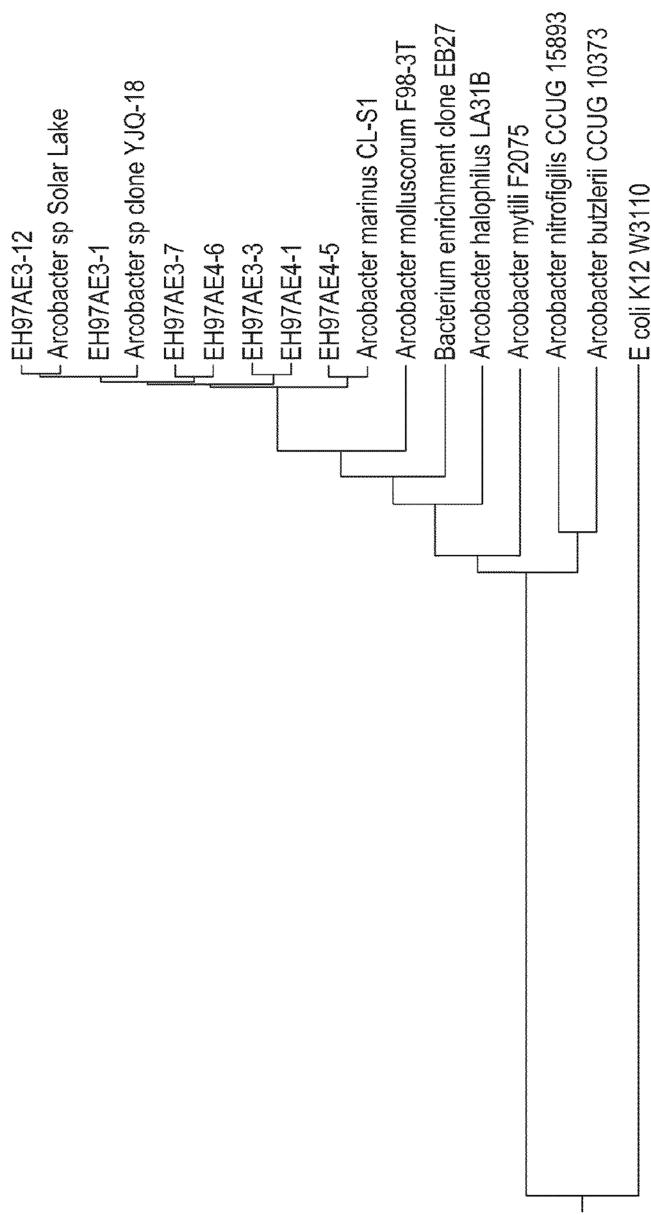
FIG. 2 shows a molecular phylogenetic tree for newly isolated *Arcobacter* species and reference bacteria based on 16S rRNA gene sequences (rDNA).

A molecular phylogenetic tree prepared herein shows the relatedness of the newly isolated strains 97AE3-12, 97AE 3-1, 97AE3-3, 97AE 3-7, 97AE 4-1, 97AE 4-5, and 97AE 4-6 to each other and to other clade 1 strains, as well as to one strain each of clades 2 and 3, in FIG. 2. The strains are closely related to each other in one branch of clade 1. These strains are characterized by their rDNA sequences: SEQ ID NOs:1, 33, 34, 35, 36, 37, and 38, respectively, Thus strains with the partial rDNA sequences of these new isolates (SEQ ID NOs: 1, 33, 34, 35, 36, 37, and 38) are *Arcobacter* clade 1 strains of the present method.

The 16S rDNA sequences of strains in each of clades 1, 2, and 3 were analyzed as groups to identify signature sequences at specified positions that may be used to distinguish the three clades. As described in Example 2 herein, specific positions in the 16S rDNA sequence have nucleotides that are characteristic for each *Arcobacter* clade, which may be fixed or may have some degeneracy, as listed in Table 6. In addition, there may be an insertion or deletion at some positions. The set (all positions together) of signature sequences for each *Arcobacter* clade that are listed in Table 6 differs from each of the other *Arcobacter* clades' set of signature sequences. The *Arcobacter* clade 1 16S rDNA dominant (most prevalent) consensus sequence (which may not be full length) containing the signature sequences, is provided as SEQ ID NO:39. Known or newly isolated microbial strains may be identified as belonging to *Arcobacter* clade 1, and thus are strains of the present method, by having 16S rDNA with at least about 97%, 98%, or 99% sequence identity to SEQ ID NO:39.

The degenerate signature sequences (including insertion/deletion positions) are present in the degenerate consensus 16S rDNA sequence for clade 1 (SEQ ID NO:40), the degenerate consensus 16S rDNA sequence for clade 2 (SEQ ID NO:41), and the degenerate consensus 16S rDNA sequence for clade 3 (SEQ ID NO:42). Known or newly isolated microbial strains may be identified as belonging to *Arcobacter* clade 1, and thus are strains of the present method, by having 16S rDNA that is of SEQ ID NO:40. In addition, known or newly isolated microbial strains may be identified as belonging to *Arcobacter* clade 1, and thus are strains of the present method, by having 16S rDNA that includes the clade 1 degenerate signature sequences listed for specific positions in Table 6.

The *Arcobacter* sp strains 97AE3-12, 97AE 3-3, 97AE3-1, 97AE 4-6, 97AE 4-5, 97AE 3-7, and 97AE 4-1 were found as shown in examples herein to have properties indicating their ability to enhance oil recovery by growing to form plugging biofilms. The strains were able to form plugging biofilms in high salinity conditions (75 ppt). Strain 97AE3-12 grew in the presence of petroleum oil, in both low (15 ppt) and high salinity (64 ppt) denitrifying conditions. Plugging biofilms were produced in low (15 ppt) and high (35 ppt and 68 ppt) salinity media. Plugging biofilms were formed with either batch or continuous nutrient feeding. In addition, silica particle aggregation was demonstrated in high salinity (64 ppt) media.

These properties of the isolated *Arcobacter* clade 1 strains demonstrate their use for forming biofilms to plug highly permeable zones in permeable sand or rock of oil reservoirs. Plugging of hyperpermeable zones may reroute water towards less permeable, more oil rich areas thereby enhancing sweep efficiency leading to increased oil recovery.

Oil Recovery Enhancing Compositions

The newly isolated *Arcobacter* strains 97AE3-12 (ATCC #PTA-11409), 97AE 3-3 (ATCC #PTA-11410), 97AE 4-6, 97AE 4-5, 97AE 3-7, and 97AE 4-1 described above may be included as components in oil recovery enhancing compositions which are an embodiment of the present invention. Thus the present compositions include at least one strain of *Arcobacter* that has a partial rDNA sequence of SEQ ID NO:1, 33, 34, 35, 36, 37, or 38, which are the rDNA sequences of these new strains. Each of the strains may be in separate oil recovery enhancing compositions, or any combination of more than one of the strains may be in the same composition.

In addition to one or more of these new *Arcobacter* clade 1 strains, the present oil recovery enhancing composition includes one or more electron acceptors and at least one carbon source. In one embodiment the electron acceptor is nitrate. Nitrate is reduced to nitrite and/or to nitrogen during growth of the described *Arcobacter* strains. Nitrite may also serve as an electron acceptor in the composition. In various embodiments the electron acceptor is one or more ionic salts of nitrate, one or more ionic salts of nitrite, or any combination of ionic salts of nitrate and nitrite.

The carbon source may be a simple or a complex carbon-containing compound. The carbon source may be complex organic matter such as peptone, corn steep liquor, or yeast extract. In another embodiment the carbon source is a simple compound such as citrate, fumarate, maleate, pyruvate, succinate, acetate, formate or lactate.

Oil recovery enhancing compositions may include additional components which promote growth of and/or biofilm formation by the microbial strains of the composition. These components may include, for example, vitamins, trace metals, salts, nitrogen, phosphorus, magnesium, buffering chemicals, and/or yeast extract In one embodiment the oil recovery enhancing compositions include one or more additional microorganisms which grow in the presence of oil. The microorganisms may use a component of oil as a carbon source, or when using an alternate carbon source their growth is not inhibited by the presence of oil. Particularly useful are other microorganisms that have properties which enhance oil recovery, such as microorganisms that form biofilms or that release oil from surfaces. In one embodiment an additional microorganism in the present composition is a microorganism of a *Shewanella* species. *Shewanella* is a bacterial genus that has been established, in part through phylogenetic classification by rDNA and is fully described in the literature (see for example Fredrickson et al., *Towards Environmental Systems Biology Of Shewanella*, Nature Reviews Microbiology (2008), 6(8), 592-603; Hau at al., *Ecology And Biotechnology. Of The Genus Shewanella*, Annual Review of Microbiology (2007), 61, 237-258).

There is at least about 89% sequence identity of 16S rDNA sequences among *Shewanella* species. *Shewanella* species have 16S rDNA which has the signature sequences of hypervariable regions 2 (SEQ ID NOs:47 and 48 are dominant and degenerate sequences, respectively), (SEQ ID NOs:49 and 50 are dominant and degenerate sequences, respectively) and 8 (SEQ ID NOs: 51 and 52 are dominant and degenerate sequences, respectively) as shown in FIG. 5. The combination of the degenerate signature sequences for each region defines *Shewanella* species, including some position variations as shown in FIG. 5. Thus *Shewanella* sp. useful in the present invention are those that comprise within the 16s rDNA the degenerate signature sequences as set forth in SEQ ID NOs: 48, 50, and 52. In one embodiment *Shewanella* sp. useful in the present invention are those that comprise within the 16s rDNA the dominant signature sequences as set forth in SEQ ID NOs:47, 49, and 51.

The dominant signature sequences in FIG. 5 are those with the variable positions designated as the most frequently found nucleotides in *Shewanella* species. *Shewanella* are gram negative, gamma-proteobacteria, which have the ability to reduce metals and are capable of additionally reducing a wide range of terminal electron acceptors. These microorganisms gain energy to support anaerobic growth by coupling the oxidation of $H_2$ or organic matter to the reduction of a variety of multivalent metals, which leads to the precipitation, transformation, or dissolution of minerals.

The ability of *Shewanella* species to alter the wettability of a hydrocarbon coated surface leading to improved oil recovery is disclosed in commonly owned and co-pending US Patent Application Publication #2011/0030956, which is herein incorporated by reference. In one embodiment an additional microorganism is *Shewanella putrefaciens, Shewanella* sp LH4:18 (ATCC No. PTA-8822; described in commonly owned U.S. Pat. No. 7,776,795), or *Shewanella* sp L3:3 (ATCC No. PTA-10980; described in commonly owned and co-pending US Patent Application Publication No. 2011/0030956).

In one embodiment *Thauera* sp. AL9:8 (ATCC #PTA-9497) is included in the present composition. *Thauera* sp. AL9:8 was isolated from subsurface soil samples and was shown to be capable of growth under denitrifying conditions using oil or oil components as the sole source of carbon. This microorganism also has oil releasing activity (U.S. Pat. No. 7,708,065).

Methods of Enhancing Oil Recovery

The present oil recovery enhancing compositions may be used to inoculate an oil reservoir leading to enhancement in oil recovery. In addition, compositions including at least one strain belonging to *Arcobacter* clade 1, as described above, and a minimal growth medium including at least one electron acceptor may be used to inoculate an oil reservoir to enhance oil recovery. Typically one or more ionic salts of nitrate and/or nitrite are used as the electron acceptor. The microorganisms of *Arcobacter* clade 1 in the composition include viable cells that populate and grow in the oil reservoir.

A minimal growth medium includes at least one carbon source, and may include other components such as vitamins, trace metals, salts, nitrogen, phosphorus, magnesium, calcium, and buffering chemicals. The carbon source may be a simple or a complex carbon-containing compound, for example, 1) oil or an oil component, 2) complex organic matter such as peptone, corn steep liquor, or yeast extract; or 3) simple compounds such as citrate, fumarate, maleate, pyruvate, succinate, acetate, formate or lactate.

Any strain belonging to *Arcobacter* clade 1, as described above, may be used which forms plugging biofilms under anaerobic denitrifying conditions in the presence of petroleum oil. Strains of microorganisms that belong to *Arcobacter* clade 1, as described above, that may be used in the present methods may be identified by their 16S rDNA sequences, which have the signature sequences described above and listed in Table 6. In addition, strains belonging to *Arcobacter* clade 1, as described above, useful in the present methods may be identified by one skilled in the art using biofilm formation, silica aggregation, and/or permeability reduction assays such as those described in Examples herein. As examples of strains belonging to *Arcobacter* clade 1, as described above, that are able to form plugging biofilms, these properties of strains 97AE3-12 (ATCC #PTA-11409), 97AE 3-3 (ATCC #PTA-11410), 97AE3-1, 97AE 4-6, 97AE 4-5, 97AE 3-7, and 97AE 4-1 are demonstrated herein. In one embodiment, any of these strains are used in the present methods.

In another embodiment, one or more microorganisms in addition to strains belonging to *Arcobacter* clade 1, as described above, which grow in the presence of oil under denitrifying conditions, are included in a composition used in the present method. Microorganisms of *Shewanella* species, which are described above, are particularly useful.

In certain oil reservoirs having specific properties, specific strains belonging to *Arcobacter* clade 1, as described above, may be best suited for use in the present methods. For example, in oil reservoirs where at least one fluid, such as injection water and/or production water, has a high concentration of salt, strains belonging to *Arcobacter* clade 1, as described above, which grow and form plugging biofilms in high salt media are particularly suitable. Specifically, *Arcobacter* clade 1 strains 97AE3-12 (ATCC #PTA-11409), 97AE 3-3 (ATCC #PTA-11410), 97AE3-1, 97AE 4-6, 97AE 4-5, 97AE 3-7, and 97AE 4-1 are particularly suited to oil reservoirs with at least one fluid having high salt, particularly salt of about 30 ppt or higher. The salt concentration may be at least about 30 ppt, 35 ppt, 40 ppt, 45 ppt, 50 ppt, 55 ppt, 60 ppt, 65 ppt, 70 ppt, or 75 ppt, or higher.

Oil reservoirs may be inoculated with compositions including one or more strain belonging to *Arcobacter* clade 1, as described above, and a minimal growth medium using any introduction method known to one skilled in the art. Typically inoculation is by injecting a composition into an oil reservoir. Injection methods are common and well known in the art and any suitable method may be used (see for example *Nontechnical guide to petroleum geology, exploration, drilling, and production,* $2^{nd}$ edition. N.J. Hyne, PennWell Corp. Tulsa, Okla., USA, Freethey, G. W., Naftz, D. L., Rowland, R. C., & Davis, J. A. (2002); *Deep aquifer remediation tools*: Theory, design, and performance modeling, In: D. L. Naftz, S. J. Morrison, J. A. Davis, & C. C. Fuller (Eds.); and *Handbook of groundwater remediation using permeable reactive barriers* (pp. 133-161), Amsterdam: Academic Press). Injection is typically through one or more injection wells, which are in communication underground with one or more production wells from which oil is recovered:

Enhanced Oil Recovery From An Oil Reservoir

Enhanced oil recovery in this context may include secondary or tertiary oil recovery of hydrocarbons from subsurface formations. Specifically, hydrocarbons are recovered that are not readily recovered from a production well by water flooding or other traditional secondary oil recovery techniques.

Primary oil recovery methods, which use only the natural forces present in an oil reservoir, typically obtain only a minor portion of the original oil in the oil-bearing strata of an oil reservoir. Secondary oil recovery methods such as water flooding may be improved using methods herein which provide microorganisms and growth media for formation of plugging biofilms in areas of subterranean formations where there is a high variation in permeability. Biofilm plugging of the highly permeable regions of a reservoir reroute water used in water flooding towards less permeable, more oil rich areas. Thus enhanced oil recovery is obtained particularly from oil reservoirs where sweep efficiency is low due to, for example, interspersion in the oil-bearing stratum of rock layers that have a substantially higher permeability compared to the rest of the rock layers. The higher permeability layers will channel water and prevent water penetration to the other parts of the oil-bearing stratum. Formation of plugging biofilms by microorganisms will reduce this channeling.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

GENERAL METHODS

The meaning of abbreviations are used in this application are as follows: "hr" means hour(s), "min" means minute(s), "day" means day(s), "mL" or "ml" means milliliters, "mg/mL" means milligram per milliliter, "L" means liters, "μL" means microliters, "mM" means millimolar, "μM" means micromolar, "nM" means nano molar, "μg/L" means microgram per liter, "pmol" means picomol(s), "° C." means degrees Centigrade, "° F." means degrees Fahrenheit, "bp" means base pair, "bps" means base pairs, "mm" means millimeter, "ppm" means part per million, "g/L" means gram per liter, "mL/min" means milliliter per minute, "mL/hr" means milliliter per hour, "cfu/mL" means colony forming units per milliliter, "g" means gram, "mg/L" means milligram per liter, "Kev" means kilo or thousands of electron volts, "psi" means pounds (of force) per square inch, "LB" means Luria broth, "rpm" means revolution per minute, "NIC" means non-inoculated control.

Growth of Microorganisms

Techniques for growth and maintenance of anaerobic cultures are described in "Isolation of Biotechnological Organisms from Nature", (Labeda, D. P. ed. 117-140, McGraw-Hill Publishers, 1990). Nitrate, the ferric iron and fumarate are each individually utilized as the primary electron acceptor under the growth conditions used herein. Under denitrification, anaerobic growth is measured by nitrate depletion from the growth medium over time. The reduction of nitrate to nitrogen has been previously described (Moreno-Vivian, C., et al., J. Bacterial., 181, 6573-6584, 1999). In some cases nitrate reduction processes lead to nitrite accumulation which is subsequently further reduced to nitrogen. Hence, accumulation and sometimes dissipation of nitrite is therefore also considered evidence for active growth and metabolism by microorganisms.

Determination of Viable Cell Titer (Most Probable Number)

In order to determine viable cell titer, samples from cultures or slim tubes were diluted by 1:10 serial dilution in 8 rows per sample of a 96 well plate using standard Miller's Luria Broth or Luria broth with 3.5% NaCl added. Titration was done using an automated Biomek200 robotic pipettor. Growth was determined by visual turbidity and recorded for each of 8 rows. The most probable number algorithm of Cochran (Biometrics (1950) pp 105-116) was used to determine the viable cells/mL and the 95% confidence limits for this number in the original sample.

The serial dilution method plating is used to determine the bacterial titer of such cultures. A series of 1:10 dilutions of such samples is plated and the resulting colonies are counted. The number of colonies on a plate is then multiplied by the dilution factor (the number of times that the 1:10 dilution was done) for that plate to obtain the bacterial count in the original sample.

Ion Chromatography

To quantitate nitrate and nitrite ions in aqueous media, Applicants used an ICS2000 chromatography unit (Dionex, Banockburn, Ill.). Ion exchange was accomplished on an AS15 anion exchange column using a gradient of 2 to 50 mM potassium hydroxide. Standard curves using known amounts of sodium nitrite or sodium nitrate solutions were generated and used for calibrating nitrate and nitrite concentrations.

Measurement of Total Dissolved Salts by Refractometer

The total dissolved salt was measured using a hand-held refractometer (Model RHS 10ATC, Huake Instrument Co., Ltd).

Samples from Oil Reservoir Production and Injection Waters

A petroleum well system was sampled for this study that is called Well #2 in the Wainwright field in the province of Alberta, Canada. This well has a salinity of about twice seawater, which is in the range of 65 ppt. Water samples were obtained from production and injection well heads as mixed oil/water liquids in glass 1.0 L brown bottles, filled to the top, capped and sealed with tape to prevent gas leakage. Gas from inherent anaerobic processes sufficed to maintain anaerobic conditions during shipment. The bottles were shipped in large plastic coolers filled with ice blocks to the testing facilities within 48 hr of sampling.

DNA Preparation for Sequence Analysis

Genomic DNA from bacterial colonies was isolated by diluting bacterial colonies in 50 μL of water or Tris-HCL buffer pH7-8. Diluted colony DNAs were amplified with Phi 29 DNA polymerase prior to sequencing (GenomiPHI Amplification Kit GE Life Sciences, New Brunswick, N.J.). An aliquot (1.0 μL) of a diluted colony was added to 9.0 μL of the Lysis Reagent (from the GenomiPHI Amplification Kit) and heated to 95° C. for 3 min followed by immediate cooling to 4° C. 9.0 μL of Enzyme Buffer and 1.0 μL of Phi 29 enzyme were added to each lysed sample followed by incubation at 30° C. for 18 hr. The polymerase was inactivated by heating to 65° C. for 10 min followed by cooling to 4° C.

DNA Sequence Analyses

DNA sequencing reactions were set up as follows: 8.0 pt of GenomiPHI amplified sample were added to 8.0 μL of BigDye v3.1 Sequencing reagent (Applied Biosystems, Foster City, Calif.) followed by 3.0 μL of 10 μM primers SEQ ID NOs:43, 44, 45, or 46 (prepared by Sigma Genosys, Woodlands, Tex.), 4.0 μL of 5× BigDye Dilution buffer (Applied Biosystems) and 17 μL Molecular Biology Grade water (Mediatech, Inc., Herndon, Va.).

Sequencing reactions were heated for 3.0 min at 96° C. followed by 200 thermocycles of (95° C. for 30 sec; 55° C. for 20 sec; 60° C. for 2 min) and stored at 4° C. Unincorporated dNTPs were removed using Edge Biosystems (Gaithersburg, Md.) clean-up plates. Amplified reactions were pipetted into one well of a pre-spun 96 well clean up plate. The plate was centrifuged for 5.0 min at 5,000×g in a Sorvall RT-7 (Sorvall, Newtown, Conn.) at 25° C. The cleaned up reactions were placed directly onto an Applied Biosystems 3730 DNA sequencer and sequenced with automatic basecalling.

Each of the assembled rDNA sequences was compared to the NCBI rDNA database (about 260,000 rDNA sequences)

using the BLAST. algorithm (Altschul et al., Journal of Molecular Biology, 1990). The highest scoring sequence identity hit was used as an identifier of the most closely related known species for strain identification.

Alternatively, to generate amplified rDNA fragments from individual strains, we chose primer sets from Grabowski et al. (FEMS Microbiology Ecology, 54:427-443 (2005)). The combination of primer SEQ ID NO:43 and primer SEQ ID NO:44 was chosen to specifically amplify bacterial rDNA sequences.

The PCR amplification mix included: 1.0× GoTaq PCR buffer (Promega), 0.25 mM dNTPs, 25 pmol of each primer, in a 50 μL reaction volume. 0.5 μL of GoTaq polymerase (Promega) and 1.0 μL (20 ng) of sample DNA were added. PCR reaction thermocycling protocol was 5.0 min at 95° C. followed by 30 cycles of: 1.5 min at 95° C., 1.5 min at 53° C., 2.5 min at 72° C. and final extension for 8 min at 72° C. in a Perkin Elmer 9600 thermocycler (Waltham, Mass.). The 1400 base pair amplification products were visualized on 1.0% agarose gels. The PCR reaction mix was used directly for cloning into pCR-TOPO4 vector using the TOPO TA cloning system (Invitrogen) as recommended by the manufacturer. DNA was transformed into TOP10 chemically competent cells selecting for ampicillin resistance. Individual colonies) were selected and grown in microtiter plates for sequence analysis. Sequencing of the amplified fragments and strain identification was as described above.

Automated Ribotypinq

Automated ribotyping was used for conclusive identification of selected strains with similar 16S rRNA sequence phylogenetic characteristics (Webster, John A (1988) U.S. Pat. No. 4,717,653; Bruce, J. L. (1996) Food Techno. 50: 77-81; and Sethi, M. R. (1997) Am. Lab. 5: 31-35). Ribotyping was performed as recommended by the manufacturer (DuPont Qualicon Inc., Wilmington, Del.). For these analyses, one fresh colony was picked, resuspended in the sample buffer and added to the processing module for the heat treatment step at 80° C. for 10 min to inhibit endogenous DNA-degrading enzymes. The temperature was then reduced, and two lytic enzymes (lysostaphin and N-acetylmuramidase; provided by the manufacturer) were added to the sample. The sample carrier was then loaded onto the Riboprinter™ system with the other commercial reagents. Restriction enzyme digestion of the sample chromosomal DNA using EcoRI enzyme, gel electrophoresis and blotting steps were completely automated. Briefly, genomic bacterial DNA was digested with the EcoRI restriction enzyme and loaded onto an agarose gel. Restriction fragments were separated by electrophoresis and simultaneously transferred to a nylon membrane. After a denaturation step, the nucleic acids were hybridized with a sulfonated DNA probe harboring the rRNA operon of *E. coli*, which includes genes for the small and large rRNA subunits, the 5S rRNA gene, and the internal transcribed spacers. The hybridized probe was detected by capturing light emission from a chemiluminescent substrate with a charge-coupled device camera. The output consisted of a densitometric fingerprint scan depicting the distribution of the genomic EcoRI restriction fragments containing sequences from the ribosomal operon(s) in the genome, that are electrophoretically separated by their molecular weights.

Screening of Strains for their Ability to Form Biofilms on Sintered Glass Filters An assay to screen for strains that could form biofilms on silica surfaces and prevent water flow through about 10 micron pore spaces (plugging) was developed using sintered glass filters. 25 mm medium coarseness sintered glass filters (stock #15254, Adams and Chittenden Scientific Glass, Berkeley Calif.) were glued into the base of plastic holders designed for membrane filtration. After curing, the filter assemblies were sterilized by autoclaving. Individual filters in holders were placed in sterile Petri plates and media which contained inoculum from overnight cultures of various strains was added on top of the glass filters. Growth medium for this biofilm formation/plugging assay was as indicated in the Examples. The plates were covered and incubated at room temperature under anaerobic conditions for one to two weeks. The filters were removed from the culture medium and the top piece screwed in place. A 1 mL syringe attached to the inlet port of the filter holder was filled with 1.0 mL of water and the time to drain the water in the tube was measured in seconds.

The sintered glass filters were prescreened for flow rate before incubation with culture and the percent change in flow rate post incubation was determined at the end of the experiment.

Screening of Strains for Aggregation of Silica

*Arcobacter* sp. strains were tested for their ability to aggregate grains of crystalline silica. Crystalline silica represents a surrogate for the sand grains common to many subterranean geological formations. A 100 μL aliquot of crystalline silica 220 g/L, (grain size range approximately 2-20 microns; Sil-co-Sil 125 made by U.S. Silica, Berkeley Springs, W. Va.) was added to each sample tube. In addition, 8 mL of medium was added and the tubes were capped to restrict oxygen entry to the medium.

Duplicate, live (inoculated) test treatments received 200 μL of frozen stock of various strains as an inoculum. Also, uninoculated control tubes were set up that contained all components, except the microbial inoculum. Tubes were statically incubated at 30° C. Treatment tubes were mixed vigorously by 10 seconds of vortexing. Turbidity increased dramatically due to resuspension of the crystalline silica, which had settled to the tube bottoms during incubation. The decline in turbidity due to settling of the crystalline silica was monitored over time after mixing by measuring OD600. The settling behavior of the silica particles showed that some strains could form a strong adhesive interaction with adjacent crystalline silica particles, causing them to settle more rapidly. In the oil field, making sand grains adherent to one another increases resistance to liquid flow through sand. This allows control over flow conformance which leads to more efficient oil recovery via water flooding.

Slim Tube Apparatus for Permeability Reduction Assay

An apparatus was designed for measuring bioplugging of permeable sand packs using slim tubes. The overall procedure for operating the slim tube was:

Packing two identical slim tubes with a mixture of sand produced from an oil well plus Sil-co-Sil 125 as described below Flooding each slim tube, under pressure Determining base permeability of packed slim tubes by flowing brine (Brine #1) into the tubes.

Successful bioplugging of these slim tube apparatuses using an *Arcobacter* inoculum suggests its utility in modifying the permeability of porous rock of an oil reservoir. Application of this strain to oil reservoirs could therefore improve oil recovery by altering the flow conformance of reservoirs under water flooding.

A schematic diagram of the slim tube experimental set up is shown in FIG. 6. All numbers below in bold refer to FIG. 6.

A sample of sand that was produced from the Schrader Bluff formation at the Milne Point Unit of the Alaska North Slope was cleaned by washing with a solvent made up of a 50/50 (volume/volume) mixture of methanol and toluene.

The solvent was subsequently drained and then evaporated off the sand to produce clean, dry, flowable sand. This sand was sieved to remove particles less than one micrometer in size. This sand was combined with washed Sil-co-Sil 125 (U.S. Silica, Berkeley Springs, W. Va.) in a 4:1 ratio, and the mixture was packed tightly into separate four foot (121.92 cm) long, about 1 cm inner diameter, flexible slim tubes (9*a*, 9*b*) and compacted by vibration using a laboratory engraver.

Both ends of each slim tube were capped with common compression type fittings to keep the sand mix in it. Flexible ⅛ inch (0.32 cm) tubing capable of sustaining the pressures used in the test was attached to the fittings. The slim tubes were mounted into a pressure vessel, (10) with the tubing passing through the ends of the pressure vessel (11 and 12) using commonly available pressure fittings (⅛ inch (0.32 cm) union bulkhead) (18*a*, 18*b* and 21*a*, 21*b*). Additional fittings and tubing were used to connect the inlet of each slim tube to a pressure pump (13*a*, 13*b*) and feed reservoir (14*a*, 14*b*). Other common compression fittings, including elbows unions and tees, and tubing connected the inlet of each slim tube to a transducer that measured the pressure above atmospheric pressure (absolute pressure gauge) (20*a*, 20*b*). The inlet of the slim tube was also connected using the same types of tubing and fittings to the high pressure side of a commonly available differential pressure transducer (19*a*, 19*b*). Fittings and tubing connected the outlet of each slim tube to the low pressure side of the differential pressure transducer (19*a*, 19*b*) and to a back pressure regulator (16*a*, 16*b*). The signals from the differential pressure and the absolute pressure transducers were ported to a computer and these pressure readings were monitored and periodically recorded. The pressure vessel (10) around the slim tubes was filled with water, which acted as a hydraulic fluid, through a water port (15). This water was slowly pressurized with air through port 17 to a pressure of about 107 pounds per square inch (psi) (0.74 mega Pascal) while Brine #1 (below) from the feed reservoirs (14*a*, 14*b*) flowed through the slim tubes and came out through the back pressure regulator (16*a*, 16*b*). This operation was performed such that the pressure in each slim tube was always 5 to 20 psi (0.034-0.137 mega Pascal) below the pressure in the pressure vessel (10).

Solutions for Slim Tube Experiments:

Brine #1: Injection water used at a well site in Alberta Canada. The total dissolve salt content was about 70 ppt. The pH of this solution was adjusted to about 6.2 to 6.4 using HCl or NaOH. This brine was applied to slim tubes both with and without filter sterilization during the course of slim tube experiments as noted in the examples.

| Recipe 200 mL | |
|---|---|
| Brine #2: (batch nutrient feed) | |
| $NaNO_3$ | 14.2 g |
| NaLactate | 7.2 g |
| $NH_4Cl$ | 720 mg |
| $KH_2PO_4$ | 144 mg |
| Yeast Extract | 3.6 g |
| pH = 6.5 | |
| Diluted 1 part in 36 of Brine #1 | |
| Brine #3: (continuous nutrient feed) | |
| $NaNO_3$ | 14.2 g |
| NaLactate | 7.2 g |
| $NH_4Cl$ | 720 mg |
| $KH_2PO_4$ | 144 mg |
| Yeast Extract | 3.6 g |
| pH = 6.5 | |

-continued

| Recipe 200 mL |
|---|
| Diluted 1 part in 327 of Brine #1. |
| Brine #5: |
| in Tap water,<br>66 ppt NaCl,<br>1000 ppm NaCitrate,<br>3725 ppm $Na_2$Fumarate,<br>100 mg/L $NH_4Cl$,<br>50 mg/L $KH_2$PO4,<br>500 mg/L yeast extract<br>1900 ppm Ca (5260 ppm $CaCl_2$)<br>Adjust the pH to ~6.2 to 6.4 with HCl. |

Measurement of Pressure Drop

The pressure drop in the slim tubes was measured using the differential pressure transducer described above. The pressure drop was measured across each slim tube at various flow rates. This pressure drop was approximately proportional to the flow rate. For each pressure drop measured at each flow rate, the base permeability of the sand pack was calculated.

Pressure drop alone can be compared and used as a measure of the change in permeability between slim tubes since all the tubes had similar dimensions and received the same flow rates of brine during the tests.

The empty volume in the slim tubes, called the pore volume, was 40-50 ml. This pore volume was calculated from the product of the total volume of the slim tube and an estimate of the porosity (about 40%).

Calculation of Base Permeability

The base permeability of each tube was measured using the Brine #1 flowing at full pressure: about 95 psi (0.665 megapascal) in the slim tube (controlled at the outlet end with the back pressure regulator) and about 110 psi (0.758 megapascal) in the pressure vessel (outside of the slim tube). Base permeability was calculated using the Darcy Equation:

$$k = \frac{4.08 * Q * \mu * L}{A_x * \Delta P}$$

ΔP=The pressure drop across a porous pack or rock, [=]psi

Q=Volumetric flow rate through pack, [=]/hr

μ=Viscosity of fluid (single phase) through pack [=] centipoise

L=Length of pack (parallel to flow), [=] cm $A_x$=Cross sectional area (normal to flow) [=] $cm^2$ k=Permeability [=] milliDarcy 4.08=a conversion constant to make the units compatible [=] mD-hr-psi/cp/$cc^2$ Base permeability, along with other properties of each packed slim tube are given in Table 3.

TABLE 3

Properties of sand packed slim tubes

| Tube # | Example Number | Tube ID, cm | Length, L, cm | Mass of sand, g | permeability, Darcy |
|---|---|---|---|---|---|
| 9a | 8, 9 | 0.978 | 121.9 | 166.4 | 0.7 |
| 9b | 10 | 0.978 | 121.9 | 175.6 | 1.2 |

Example 1

Anaerobic Enrichment for Indigenous Microbes from Oil Reservoir Samples

To enrich for species that could reduce any of the electron acceptors nitrate, fumarate or the ferric ion (Fe (III), we inoculated 1 mL of either injection water or production water from Well #2, described in General Methods, into 9 mL of minimal salts media (Table 4) in 20 mL anaerobic serum vials, supplemented with lactate (2000 ppm) as the carbon source, sodium chloride to 4300 ppm and as electron acceptor either 1.6 g/L sodium nitrate, or 3.5 g/L sodium fumarate, or 13,000 ppm NaEDTAFe(III). A fourth enrichment having a rich medium, Marine broth (Difco™ B. D. Diagnostics Sparks Md.), which was supplemented with sodium chloride to 3900 ppm and lactate to 2000 ppt, was used to enrich for microbes that require more than a minimal medium for growth. The electron acceptor in the Marine broth sample was scavenged from the Fe (III), sulfate, nitrate and organic molecules in the formulation that could be used as electron acceptors. Each sample of medium was deoxygenated by sparging the filled vials with a mixture of nitrogen and carbon dioxide followed by autoclaving. All manipulations of bacteria were performed in an anaerobic chamber (Coy Laboratories Products, Inc., Grass Lake, Mich.), and the cultures were incubated at ambient temperature.

TABLE 4

| Minimal salts medium | |
|---|---|
| g/L | Chemical |
| 1.0 | $NH_4Cl$ |
| 0.5 | $KH_2PO_4$ |
| 0.4 | $MgCl_2•6H_2O$ |
| 0.2 | $CaCL_2•2H_2O$ |
| 10 | NaCl |
| 0.69 | NaH2PO4 |
| 2.5 | $NaHCO_3$ |
| 0.073 | $KSO_4$ |
| 1000X g/L | Trace elements |
| 1.5 | $FeCl_2•4H_2O$ |
| 0.002 | $CuCl_2•2H_2O$ |
| 0.1 | $MnCL_2•4H_2O$ |
| 0.19 | $CoCl_2•6H_2O$ |
| 0.07 | $ZnCl_2$ |
| 0.006 | $H_3BO_3$ |
| 0.036 | $Na_2MoO_4•2H_2O$ |
| 0.024 | $NiCl_2•6H_2O$ |
| 0.277 | HCl |
| 1000X g/L | Selenium/tungstate |
| 0.006 | $Na_2SeO_3•5H_2O$ |
| 0.008 | $Na_2WO_4•2H_2O$ |
| 0.5 | NaOH |
| 1000X mg/L | Vitamin mix |
| 100 | vitamin B12 |
| 80 | p-aminobenzoic acid |
| 20 | D(+)-Biotin |
| 200 | nicotinic acid |
| 100 | calcium pantothenate |
| 300 | pyridoxine hydrochloride |
| 200 | thiamine-HCL•$2H_2O$ |
| 50 | Alpha-lipoic acid |

The pH of the medium was adjusted to 7.3.

The enrichments containing nitrate were monitored and sampled regularly for nitrate depletion and nitrite accumulation, or in some cases, nitrite depletion. When nitrate was depleted in the sample (usually by 14 days), lactate and nitrate were added to the original final concentrations. Lactate and the electron acceptor in each of the other enrichments were added to the original final concentrations as well. In the marine broth enrichment sample, lactate was added for further incubation.

All vials were incubated for addition 14 to 20 days at room temperature. Changes which indicated growth on lactate and the electron acceptor combination of each enrichment were observed in the vial samples. Changes included visible turbidity in the medium, and the presence of biofilms on the glass vials or at the gas-aqueous interface, as well as nitrate and nitrite reduction in vials containing nitrate as the electron acceptor. Turbidly was similar in each vial indicting that there was a diverse population of microorganisms in both the injection water and the production water.

After a second incubation of 14-20 days at room temperature, a 100 μL sample from each enrichment was streaked onto Marine broth agar plates (made per recipe, Difco 2216, Becton-Dickenson, Sparks, Md.) and incubated at room temperature for two days. Representative colonies with unique morphologies were isolated, restreaked onto Marine broth agar plates, and grown to purify isolates. Samples of isolated colonies were screened for identification by PCR amplification using direct colony rDNA analysis described in the General Methods using both the reverse PCR primer 1492R (SEQ ID NO:43) and forward PCR primer 8F(SEQ ID NO:44). The DNA sequencing and analysis described in General Methods was used to obtain 16S rDNA sequence for microbial identification. Isolates identified as belonging to *Arcobacter* were primarily obtained from the fumarate and marine broth enrichments of the production water. Seven isolates were named 97AE 3-12, 97AE3-1, 97AE 3-3, 97AE 3-7, 97AE 4-6, 97AE 4-5, and 97AE4-1.

Example 2

Characterization of Isolated Strains with Respect to *Arcobacter* sp.

To determine the 16S rDNA sequence of the seven isolates named 97AE 3-12, 97AE3-1, 97AE 3-3, 97AE 3-7, 97AE 4-6, 97AE 4-5, and 97AE4-1 (Example 1), each of the seven isolates was picked as a pure single colony, DNA was isolated and the 16S rRNA gene was amplified by PCR using the procedures in General Methods. The amplified sequences were cloned into pCR-TOPO4 vector using the TOPO TA cloning system (Invitrogen), as recommended by the manufacturer, and then sequenced multiple times using primers 1492R, 8F, M13 Reverse, and M13 Forward of SEQ ID NOs: 43-46, respectively, to obtain the near full sequence. Each strain 16S rDNA sequence (97AE 3-12: SEQ ID NO:1, 97AE3-1: SEQ ID NO:33, 97AE 3-3: SEQ ID NO:34, 97AE 3-7: SEQ ID NO:35, 97AE 4-6: SEQ ID NO:38, 97AE 4-5: SEQ ID NO:37, and 97AE4-1: SEQ ID NO:36) was queried against the NCBI (National Center for Biotechnology Information) database using the BLAST (Basic Local Alignment Search Tool) algorithm program provided by NCBI (Altschul, et al. (1990) J. Mol. Biol. 215:403-410) to identify the most similar nucleotide sequences. This was executed by comparing the query sequence to similar 16S rDNA sequences in the database and determining a score of relative percent identity. All query sequences, one each for 97AE 3-12, 97AE3-1, 97AE 3-3, 97AE 3-7, 97AE 4-6, 97AE 4-5, and 97AE4-1, returned top hits as *Arcobacter* marinus CL-S1

(SEQ ID NO:4), *Arcobacter* sp. Solar Lake (SEQ ID NO:2), or *Arcobacter* sp. YJQ-18 (SEQ ID NO:3) at greater than or equal to 99% identity.

Based on the initial *Arcobacter* identity, 24 16S rDNA reference sequences in the NCBI database from the *Arcobacter* genus and 5 related sequences were selected. These sequences are listed in Table 1 with SEQ ID NOs: 2-6,8,9, and 11-31. Reference sequences included 10 from *Arcobacter* strains (SEQ ID NOs:4, 6, 8, 9, 15, 17-21) that represent 12 different *Arcobacter* species (Type strains) recognized by the International Committee on Systematics of Prokaryotes (List of Prokaryotic names with Standing in Nomenclature). Also the reference sequences included 6 strains from oil reservoirs (SEQ ID NOs:3, 5, 24, 25, 28 and 31). Other *Arcobacter* isolates and strains were included as reference sequences because they had been referenced in peer reviewed journals as *Arcobacter* sp. but had not yet been critically typed and described as species (SEQ ID NOs:2, 11-14, 16, 22, 23, 26, 27 and 30). In addition the *E. coli* K12 16S rDNA B sequence (positions 8-1511; SEQ ID NO:32) was used to serve as a scaffold for the sequence alignment and to provide the base coordinate system, which is recognized as the base position standard (Brosius, J., et al. (1981) J. of Molecular Biology, 148(2):107-127; Woese, (1987) *Bacterial Evolution*. Microbial Rev. 51: 221-271). The test sequence for alignment was from strain 97AE3-12 (SEQ ID NO:1). This sequence was representative of the other six strains based on sequence stretches (500-700 bp) which showed high sequence identity between all six strains and *Arcobacter marinus* CL-S1 (GenBank: EU512920).

A global alignment was created using near full length 16S rDNA sequences of SEQ ID NOs:1-6,8,9, and 11-32 with the Clustal W alignment algorithm (Chenna, R. H., et al, 2005 and Lark, M. A. et al, 2007). All 24 *Arcobacter* sequences aligned and showed a significant distance in identity to the *E. coli* K12 16S rDNA with sequence identity of 76 to 78%. All sequences demonstrated a 25 bp deletion when compared to the *E. coli* K12 sequence in variable region 3 at base coordinate positions 452 to 476. There also was a 4 bp insertion (WGCT) in variable region 6 at base coordinate position 1028 and a 6 bp deletion in variable region 9 at base coordinates 1451 to 1456. These structural signatures are consistent with the signature for the following phylogenetic classification: *Bacteria/Epsilonproteobacteria/Campylobacterales/Campylobacteraceae/Arcobacter.*

The alignment yielded the closest sequence identities for strain 97AE3-12 to *Arcobacter* sp. sequences shown in Table 5.

TABLE 5

97AE3-12 and known 16S rDNA sequences having closest sequence identities

| Matching sequence description | *Overlap | Identity |
|---|---|---|
| Uncultured *Arcobacter* sp. clone YJQ-18, 16S rRNA gene partial sequence. GenBank: AY569293.1 | 1471/1473 | 99.9% |
| *Arcobacter* sp. Solar Lake, Sinai Peninsula, 16S rRNA gene partial sequence (GenBank: L42994.1) | 1431/1437 | 99.7% |
| *Arcobacter marinus* CL-S1 (JCM 15502$^T$), 16S rRNA gene, partial sequence (GenBank: EU512920.2) | 1419/1426 | 99.5% |
| Bacterium enrichment culture clone EB27.1, 16S rRNA gene, partial sequence. GenBank EU573100 | 1432/1474 | 97.1% |

TABLE 5-continued

97AE3-12 and known 16S rDNA sequences having closest sequence identities

| Matching sequence description | *Overlap | Identity |
|---|---|---|
| *Arcobacter halophilus* LA31B (ATCC BAA-1022T), 16S rRNA gene, partial sequence, GenBank: AF513455.1 | 1352/1402 | 96.4% |
| *Arcobacter mytili* strain F2075 (LMG 24559$^T$), 16S rRNA gene, partial sequence GenBank: EU669904.1 | 1334/1401 | 94.5% |
| *Arcobacter nitrofigilis* (DSM 7299), complete genome, GenBank: CP001999.1 | 1337/1477 | 94.6% |
| *Arcobacter butzleri* RM4018, complete genome. GenBank: AY570593 | 1375/1479 | 93.0% |
| Bacterium enrichment culture clone PL-8B1, 16S rRNA gene, partial sequence. Low temperature oil reservoir GenBank | 1366/1477 | 92.5% |
| *Thiomicrospira* sp. CVO, 16S rRNA gene, partial sequence GenBank: U46506.2 | 1088/1277 | 85.2% |

*Overlap means the length of overlapping sequence that was used to determine the percent identity (includes mismatches, deletions, and insertions between fixed ends). This varies due to variability of available sequence length for different 16S rDNA sequences.

A phylogenetic tree was created by Clustal W alignment with the same rDNA sequences (SEQ ID NOs:1-6,8,9,11-32) using the phylogenetic tree and bootstrapping functions of the MegAlign™ program in the DNAstar LaserGene package (LaserGene™ DNASTAR, Inc Madison, Wis.). The phylogenetic tree shown in FIG. 1 shows all *Arcobacter* reference strains with strain 97AE3-12. The ten recognized *Arcobacter* reference strains form three clades (1, 2, and 3) in the molecular phylogenetic analysis, *A. marinus* and *A. halophilus* are in clade 1, *A. nitrofigillis* is in clade 2, and the known pathogens represented by *A. butzlerii* are all in clade 3. As shown in FIG. 1, strain 97AE3-12 falls within the *Arcobacter* clade 1 which includes *Arcobacter marinas* CL-S1 (JCM 15502$^T$) (Kim, H. M. et al Int. J. Syst. Evol. Microbiol. 60:53 (2010) which is the type reference strain with the highest sequence identity at 99.5%. Other isolated and described strains in clade 1 include *Arcobacter* sp Solar Lake, *Arcobacter halophilus* LA31B (ATCC BAA-1022$^T$) (Teske et al. (1996) Appl. Environ. Microbiol. 62:4210; Donachie et al (2005) Int. J. Syst. Evol. Microbial. 55:1271). Though *A. mytili* F2075 and *A. nitrofigillis* DSM7299 have practically the same percent 16S rDNA sequence identity to 97AE3-12, the signature sequences of the 16S rDNA of these two strains place them in clades 1 and 2, respectively.

Phylogenetic clade 3 is anchored by *Arcobacter butzleri* (the most described and isolated *Arcobacter* species). This clade also contains *Arcobacter skirrowi, Arcobacter thereius, Arcobacter cibarius* and *Arcobacter cryaerophilus*. All of these strains are BSL2 organisms.

In the same manner a molecular phylogenetic tree was generated to show the relatedness among newly isolated strains 97AE 3-12, 97AE3-1, 97AE 3-3, 97AE 3-7, 97AE 4-6, 97AE 4-5, and 97AE4-1, and also their relationship to a subset of the reference strains used above. This tree shown in FIG. 2 indicates the close relationship between the newly isolated strains and the known strains *Arcobacter* sp. Solar Lake and *Arcobacter* sp. YJQ-18 that are shown in FIG. 1 to be in *Arcobacter* clade 1.

Using the same global multiple sequence alignment described above, signature positions in the 16S rDNA sequences were identified which may be used to distinguish *Arcobacter* species in clade 1 from the *Arcobacter* species in clades 2 and 3 by the signature sequences at these positions. These signature positions are listed in Table 6, with position coordinates from the *E. coli* 16S rDNA sequence. The consensus sequence for *Arcobacter* sp. clade 1 at each of the signature positions is listed. At some positions a single nucleotide occurs, while at other positions there is degeneracy where R may be A or G, Y may be C or T, M may be A or C, K may be G or T, S may be C or G, W may be A or T, B may be C, G, or T, D may be A, G, or T, H may be A, C, or T, V may be A, C, or G and N is A, C, G or T.

In Table 6 the *Arcobacter* sp. clade 1 consensus nucleotides at each signature position are compared to the consensus nucleotides for each signature position of *Arcobacter* sp. clade 2 and clade 3. In addition to consensus nucleotides of clade 1, the nucleotides present at each signature position in clade 1 strains 97AE3-12, *Arcobacter marinus* CL-S1 and *Arcobacter halophilus* LA31B are shown in Table 6. The nucleotides at all of the signature positions together, for each of these strains, identifies these strains as *Arcobacter* sp. clade 1, while there are differences from the *Arcobacter* sp. clade 1 consensus nucleotides among the signature positions for *Arcobacter* sp clade 2 and clade 3 species.

The majority of the signature positions identified were located in the hypervariable regions of the 16S rDNA, with positions designated by nucleotides of the 16S rDNA sequence from *E. coli:* hypervariable region 1 between positions 44 and 110 hypervariable region 2 between positions 120 and 300 hypervariable region 3 between positions 365 and 500 hypervariable region 4 between positions 574 and 750 hypervariable region 5 between positions 820 and 880 hypervariable region 6 between positions 990 and 1050 hypervariable region 7 between positions 1115 and 1175 hypervariable region 8 between positions 1240 and 1370 hypervariable region 9 between positions 1415 and 1465

The identified signature sequences in the 16S rDNA sequence may be used to identify microorganism strains as belonging to *Arcobacter* clade 1 as opposed to *Arcobacter* sp. clade 2 or 3. A composite degenerate 16S rDNA sequence for *Arcobacter* sp. clade 1 that contains all of the degenerate signature sequences in Table 6 is SEQ ID NO:40. This degenerate sequence includes insertion/deletion positions in Table 6. Known or newly isolated microbial strains may be identified as belonging to *Arcobacter* sp. clade 1 by having 16S rDNA that is of SEQ ID NO:40. The most prevalent, or dominant consensus 16S rDNA sequence for *Arcobacter* sp. clade 1 16S rDNA is SEQ ID NO:39. 16S rDNA sequences containing all of the signature sequences in Table 6 for *Arcobacter* clades 2 and 3 are SEQ ID NOs:41 and 42, respectively. An alignment of the 16S rDNA sequences for *Arcobacter* clade 1 dominant consensus, *Arcobacter* clade 1 degenerate consensus, strain 97AE3-12, *Arcobacter* clade 2 degenerate consensus, and *Arcobacter* clade 3 degenerate consensus is shown in FIG. 3. The differences between the 16S rDNA signature sequences for clades 1, 2, and 3 are in bold and underlined. Explanations for the notations in FIG. 3A-D:

No bracket around "N" or "–" (insertion or deletion, respectively) means that is the dominant and only sequence (it may be degenerate as indicated by the letter used).

[N] means the nucleotide exists in more than one reference sequence; it is prevalent but also a "–" exists in our isolates and nearest neighbors.

(N) means the nucleotide only exists in one reference sequence and is dominated by a "–" at that position.

TABLE 6

16S rDNA signature sequences for distinguishing *Arcobacter* Clade 1 from *Arcobacter* Clades 2 and 3, including nucleotides for *Arcobacter* Clade 1 dominant and degenerate consensus signature sequences and for strains 97AE3-12, *Arcobacter marinus*, and *Arcobacter halophilus* at the signature postitions using coordinates of *E. coli* 16S rDNA

| *E. coli* K12 W3110 rraB Coordinate No. | 97AE3-12 | *Arcobacter marinus* | *Arcobacter halophilus* | *Arcobacter* Clade 1 Dominant Consensus Signature | *Arcobacter* Clade 1 Degenerate Consensus Signature | *Arcobacter* Clade 2 BSL1 Degenerate Consensus Signature | *Arcobacter* Clade 3 BSL2 Degenerate Consensus Signature |
|---|---|---|---|---|---|---|---|
| 44-48 | GTGCT | GTGCT | GTGCT | GTGCT | GTGCT | GTGCT | GTGCT |
| 69-70 | AG | AG | AG | AG | AG | AG | AG |
| 79 | 1 n.t.* deletion | 1 n.t. deletion | A | A | 1 n.t. deletion or A | A | A |
| 73-83 | CGGGAT--TAGC | CGGGAT--TAGC | CGGATT**A**TAGC | CGGGATATAGC | CGGRWT[**A**]TAGC | CGGRTT**A**WAGC | CGGATT**A**TAGC |
| 89 | | | 1 n.t. insertion | 1 n.t. insertion T | 1 n.t. insertion T or no insertion | 1 n.t. insertion T | 1 n.t. insertion T |
| 86-93 | GCTAATCT | GCTAATCT | GCTATAATT | GCTA(T)AATT | GCTA(T)AWYT | GCTW(W)WWYT | GCTA(T)ARTT |
| 100 | 1 n.t. insertion T | 1 n.t. insertion T | 1 n.t. insertion T | 1 n.t. insertion T | 1 n.t. insertion T | 1 n.t. insertion T | 1 n.t. insertion T |
| 94-100 | GTCAGCTA | GTCAGCTA | GTCAGCTA | GTCAGCTA | GTCAGCTA | GTCAGCTA | GTCAGCTA |
| 108 | C | C | C | C | C | C | C |

TABLE 6 -continued 16S rDNA signature sequences for distinguishing *Arcobacter* Clade 1 from *Arcobacter* Clades 2 and 3, including nucleotides for *Arcobacter* Clade 1 dominant and degenerate consensus signature sequences and for strains 97AE3-12, *Arcobacter marinus*, and *Arcobacter halophilus* at the signature postitions using coordinates of *E. coli* 16S rDNA

| *E. coli* K12 W3110 rraB Coordinate No. | 97AE3-12 | *Arcobacter marinus* | *Arcobacter halophilus* | *Arcobacter* Clade 1 Dominant Consensus Signature | *Arcobacter* Clade 1 Degenerate Consensus Signature | *Arcobacter* Clade 2 BSL1 Degenerate Consensus Signature | *Arcobacter* Clade 3 BSL2 Degenerate Consensus Signature |
|---|---|---|---|---|---|---|---|
| 122-126 | ATATA | ATATA | ATATA | ATATA | RTATA | RTATA | RTATA |
| 132 | 1 n.t. insertion G | 1 n.t. insertion G | 1 n.t. insertion G | 1 n.t. insertion G | 1 n.t. insertion R | M | A |
| 128-133 | GTAACGT | GTAACGT | GTAACGT | GTAACGT | GTAACRT | GTAACMT | GTAATAT |
| 137-149 | TTACAAGAGG GGGA | TTCAAGAGG GGGA | TCTAAGAGGG GGA | TTCAAGAGG GGGA | YYYAAGAGGG GGA | CTMDAGARR RGRA | TCTTACTAAG GGA |
| 154-156 | AGA | AGA | AGA | AGA | AGW | AGW | ARW |
| 165-167 | TCT | TCT | TCT | TCT | WCT | WCT | WYT |
| 173-178 | AACCCC | GACCCC | TACCTT | AACCCC | DRYCYY | CACCCC | TACCTT |
| 182-188 | TGCCTTT | TGCCTTT | TGCCTTT | TGCCTTT | TGCCTTT | TGCCTTT | YTCCWYY |
| 189-204 | AATGCGAAA GTATGCA | AATACAAAA GTATGAA | AATACGAAAGT ATGCA | AATACGAAA GTATGCA | AATRCDAAAGT ATGMA | AAKACHYAW GTYTGCA | YYAWCHWAA GWTRRWA |
| 211 | | | 1 n.t. insertion C | | 1 n.t. insertion C or no insertion | | |
| 206-219 | GGGAAATAT TTATA | GGGAAATAT TTATA | GGGAAA**C**GCT TTAGT | GGGAAATAT TTATA | GGGAAA(**C**)KY TTWAKW | GGGAAACAT TTATG | GGGAAAGATT TATT |
| 221-226-230-233 | CTTGAA CGGC | CTTGAA CGGC | CTTAGA CGGC | CTTGAA CGGC | CTTRRR TGGC | CTCTAG KGGY | GTAAGA TAGC |
| 235-242 | TGTACAGT | TGTACAGT | TGTACAGT | TGTACAGT | TGTAYWGT | TGTAYRGT | TGTATTGT |
| 245 | C | C | C | C | C | C | C |
| 248-250 | ATA | ATA | CTA | ATA | MTA | MTM | TTA |
| 253 | T | T | T | T | T | T | T |
| 257-59 | GAG | GAG | GAG | GAG | GRG | GAG | GGG |
| 264-265 | TA | TA | TA | TA | KA | TG | TG |
| 267-269 | CTC | CTC | CTC | CTC | CYY | CTC | CCT |
| 273 | A | A | A | A | A | A | A |
| 276-280 | TCAAT | TCAAT | GCAAT | TCAAT | DCAAT | RCAAT | ACDAT |
| 283-288 | CGCTTAA | CGCTTAA | CGCTTAA | CGCTTAA | CGCWTAA | CRCYTAA | CGCATAA |
| 295 | T | T | T | T | T | T | T |
| 307 | T | T | T | T | T | T | T |
| 311 | T | T | T | T | T | T | T |
| 378-385 | GGGAAACC | GGAAACC | GGGAAACC | GGGAAACC | GGGRAACC | ACGAAAGT | ACGAAAGT |
| 396-398 | AAC | AAC | AAC | AAC | AAC | AAC | AAC |
| 407-419 | GAGGATGAC ACAT | GAGGATGAC ACAT | GAGGATGACA CAT | GAGGATGAC ACAT | GAGGATGACA CAT | GAGGATGAC ACAT | GAGGATGACA CAT |
| 425-427 | TGC | TGC | TGC | TGC | TGC | TGC | TGC |
| 433-435 | CTC | CTC | CTC | CTC | CTC | CTC | CTC |

TABLE 6 -continued 16S rDNA signature sequences for distinguishing *Arcobacter* Clade 1 from *Arcobacter* Clades 2 and 3, including nucleotides for *Arcobacter* Clade 1 dominant and degenerate consensus signature sequences and for strains 97AE3-12, *Arcobacter marinus*, and *Arcobacter halophilus* at the signature postitions using coordinates of *E. coli* 16S rDNA

| *E. coli* K12 W3110 rraB Coordinate No. | 97AE3-12 | *Arcobacter marinus* | *Arcobacter halophilus* | *Arcobacter* Clade 1 Dominant Consensus Signature | *Arcobacter* Clade 1 Degenerate Consensus Signature | *Arcobacter* Clade 2 BSL1 Degenerate Consensus Signature | *Arcobacter* Clade 3 BSL2 Degenerate Consensus Signature |
|---|---|---|---|---|---|---|---|
| 440-449 | TATATAAGAA | TATATAAGAA | TATATAGGAA | TATATAAGAA | TATATARGAA | TATATAGGAA | TATATAAGAA |
| 452-479 | 25 n.t. deletion -- | 25 n.t. deletion -- | 25 n.t. deletion - | 25 n.t. deletion -- | 25 n.t. deletion -- | 25 n.t. deletion -- | 25 n.t. deletion -- |
| 477-479 | TAA | TAA | AAA | TAA | WAA | TAA | TAA |
| 484-497 | GGTATTATAT GAAT | GGTATTATAT GAAT | GGTACTATATG AAT | GGTATTATAT GAAT | GGTAYTATATG AAT | GGTACYATA TGAAT | GGTATTATAT GAAT |
| 502 | A | A | G | A | R | A | A |
| 539 | A | A | A | A | A | A | R |
| 543 | T | T | C | T | Y | T | T |
| 554 | C | C | C | C | C | C | C |
| 562 | C | C | C | C | C | Y | C |
| 576-582 | AGCGTGT | AGCGTGT | AGCGTGT | AGCGTGT | AGCGTGT | AGCRTGT | AGCRTGT |
| 589-593 | ATAGA | ATAGA | ATAGA | ATAGA | ATMRA | GTAWW | ATTRA |
| 599-603 | CAGAA | CAGAA | TAGGA | CAGAA | YAGRA | YDGAA | TTGAA |
| 613-620 | AATAGCTT | AATAGCTT | TATGGCTC | AATAGCTT | WATRGCTY | WATRGCTY | TATAGCTT |
| 624-627 | TATT | TATT | CATA | TATT | YATW | YATW | TATA |
| 635-641 | TTTTGAA | TTTTGAA | TTCTAA | TTTTGAA | TTYTRAA | TTCCAAA | TTTGAAA |
| 646-658 | TCTATCTAGA GTA | TCTATCTAGA GTA | TCTATCTAGAG TA | TCTATCTAGA GTA | TYWATCTAGA GTA | KTAACCTAG AATR | TTAACCTAGA ATG |
| 705 | G | G | G | G | G | K | G |
| 734-738 | ATCTA | ATCTA | ATCTA | ATCTA | ATCTA | ATCTA | ATCTA |
| 744-751 | ACATAACT | ACATAACT | ACATAACT | ACATAACT | ACATAACT | ACAYWATT | ACAHTATT |
| 758-764 | GAGACGC | GAGACGC | GAGACGC | GAGACGC | GAGACGC | GAGAYGC | GAGAYGC |
| 822-824 | TAC | TAC | TAC | TAC | TAC | YAC | TAC |
| 835-840 | GCTATG | GCTATG | GCCATG | GCTATG | GCYATR | GTGAGG | GTGAGR |
| 842-848 | CGACATA | CGACATA | CGACATG | CGACATA | CGACATD | AGACCTT | YGAYCTT |
| 878 | A | A | A | A | A | R | A |
| 903 | A | A | A | A | R | A | A |
| 948 | C | C | C | C | Y | C | C |
| 971 | G | G | G | G | G | R | A |
| 989 | T | T | T | T | T | W | A |
| 998-1002 | AGTAA | AGTAA | AGTAA | AGTAA | AGWAA | AGWAA | AGTAA |
| 1006-1011 | CCATTT | CCATTT | CCATTT | CCATTT | YHMTYY | CNTWHY | YKWTYW |
| 1027-1028 | TC | TC | TC | TC | YY | YY | TC |
| 1028> | 4 n.t. insertion TGCT | 4 n.t. insertion TGCT | 4 n.t. insertion TGCT | 4 n.t. insertion TGCT | 4 n.t. insertion WGCT | 4 n.t. insertion WGCT | 4 n.t. insertion TGCT |

TABLE 6 -continued 16S rDNA signature sequences for distinguishing *Arcobacter* Clade 1 from *Arcobacter* Clades 2 and 3, including nucleotides for *Arcobacter* Clade 1 dominant and degenerate consensus signature sequences and for strains 97AE3-12, *Arcobacter marinus*, and *Arcobacter halophilus* at the signature postitions using coordinates of *E. coli* 16S rDNA

| *E. coli* K12 W3110 rraB Coordinate No. | 97AE3-12 | *Arcobacter marinus* | *Arcobacter halophilus* | *Arcobacter* Clade 1 Dominant Consensus Signature | *Arcobacter* Clade 1 Degenerate Consensus Signature | *Arcobacter* Clade 2 BSL1 Degenerate Consensus Signature | *Arcobacter* Clade 3 BSL2 Degenerate Consensus Signature |
|---|---|---|---|---|---|---|---|
| 1030-1034 | GCAGA | GCAGA | GCAGA | GCAGA | GCWRR | GCWRR | GCAGA |
| 1036 | A | A | G | A | R | R | A |
| 1038-1043 | TTATAT | TTATAT | TTATAT | TTATAT | TTWYAT | TWWYAT | TTRYAT |
| 1116-1117 | CG | CG | CG | CG | CG | CG | CG |
| 1119-1123 | CATTA | CATTA | CGTTA | CATTA | CRTTA | SDTTA | CBTTA |
| 1133-1134 | AC | AC | AG | AC | AS | AG | AG |
| 1136 | T | T | A | T | W | T | T |
| 1140 | G | G | C | G | S | C | C |
| 1152-1154 | ATG | ATG | ACG | ATG | AYG | AHS | ARS |
| 1164-1165 | AC | AC | GG | AC | RS | RS | RS |
| 1167 | 1 n.t. deletion | 1 n.t. deletion | 1 n.t. deletion | 1 n.t. deletion | 1 n.t. deletion | 1 n.t. deletion | 1 n.t. deletion |
| 1168 | C | C | C | C | C | Y | C |
| 1171-1172 | GT | GT | CC | GT | SY | SY | GT |
| 1189 | C | C | C | C | C | C | Y |
| 1216 | A | A | A | A | A | W | T |
| 1244 | G | G | G | G | G | G | R |
| 1251-1252 | AA | AA | AA | AA | AA | AA | RW |
| 1257 | A | A | A | A | A | A | N |
| 1260 | G | G | A | G | R | R | R |
| 1263 | ACAGT | ACAGT | ACAGT | ACAGT | ACRGY | ACRGT | ACGGT |
| 1270 | TG | TG | TG | TG | YG | YG | CG |
| 1278 | A | A | A | A | R | R | A |
| 1284-1286 | AA-- | AA-- | AA-- | AA-- | HA-- | YA-- | YA[--] or (**T**) |
| 1286 | 1 n.t. deletion | 1 n.t. deletion | 1 n.t. deletion | 1 n.t. deletion | 1 n.t. deletion | 1 n.t. deletion | 1 n.t. deletion or T substitution |
| 1290-1293 | ATAC | ATAC | ATAC | ATAC | ATRY | ATRY | ATRY |
| 1297 | C | C | C | C | Y | C | C |
| 1308 | T | T | A | T | W | W | T |
| 1310 | T | T | T | T | T | W | T |

TABLE 6 -continued 16S rDNA signature sequences for distinguishing *Arcobacter* Clade 1 from *Arcobacter* Clades 2 and 3, including nucleotides for *Arcobacter* Clade 1 dominant and degenerate consensus signature sequences and for strains 97AE3-12, *Arcobacter marinus*, and *Arcobacter halophilus* at the signature postitions using coordinates of *E. coli* 16S rDNA

| *E. coli* K12 W3110 rraB Coordinate No. | 97AE3-12 | *Arcobacter marinus* | *Arcobacter halophilus* | *Arcobacter* Clade 1 Dominant Consensus Signature | *Arcobacter* Clade 1 Degenerate Consensus Signature | *Arcobacter* Clade 2 BSL1 Degenerate Consensus Signature | *Arcobacter* Clade 3 BSL2 Degenerate Consensus Signature |
|---|---|---|---|---|---|---|---|
| 1327-1329 | ACA | ACA | ACT | ACA | ACR | RCY | ACA |
| 1343-1344 | GC | GC | GC | GC | (sometimes) 1 n.t. insertion G>(G)< C | GC | GC |
| 1355-1356 | AG | AG | AG | AG | AG | AG | AG |
| 1361 | 1 n.t. insertion >C< | 1 n.t. insertion >C< | 1 n.t. insertion >C< | 1 n.t. insertion >C< | 1 n.t. insertion >C< | 1 n.t. insertion >C< | 1 n.t. insertion >C< |
| 1362 | A | A | A | A | W | W | T |
| 1364 | T | T | T | T | Y | T | T |
| 1367 | T | T | T | T | T | W | T |
| 1370 | | | | | | | 1 n.t. insertion (**A**) |
| 1396 | T | T | T | T | W | T | T |
| 1419 | G | G | G | G | G | G | G |
| 1421-1426 | TGATTT | TGATTT | TGATTT | TGATTT | TGAWTT | TGAWYT | TGAACT |
| 1428-1332 | ACTCG | ACTCG | ACTCG | ACTCG | ACYCG | ATTCG | ATTCG |
| 1436-1440 | CGGGG | CGGGG | CGGGG | CGGGG | CRGGG | CGGRG | CGGGG |
| 1444 | C | C | C | C | Y | C | C |
| 1448-1449 | GA | GA | GA | GA | RR | AR | AR |
| 1451-1456 | 6 n.t. deletion -- | 6 n.t. deletion -- | 6 n.t. deletion -- | 6 n.t. deletion -- | 6 n.t. deletion -- | 6 n.t. deletion -- | 6 n.t. deletion -- |
| 1458 | G | G | G | G | R | G | G |
| 1464 | C | C | C | C | Y | Y | T |
| 1468 | A | A | A | A | H | A | A |
| 1475 | A | A | A | A | W | W | T |
| 1477 | T | T | T | T | Y | Y | Y |
| 1503 | A | A | A | A | R | R | A |

R = A/G;
K = G/T;
S = C/G;
Y = C/T;
M = A/C;
W = A/T;
D = A/G/T not C;
H = A/C/T not G;
B = C/G/T not A;
V = A/C/G not T
*n.t. is nucleotide Example 3

Riboprinting to Determine Strain Differences

The *Arcobacter* sp. strains isolated in Example 1: 97AE3-12, 97AE3-1, 97AE 3-3, 97AE 3-7, 97AE 4-6, 97AE 4-5, and 97AE4-1 were subjected to automated Riboprinter® analysis, as described in General Methods, to determine whether these isolated strains were unique with respect to one another. As a reference strain, *Arcobacter* halophilus (ATCC strain BAA-1022), which has 16S rDNA with 96.4% sequence identity to strain 97AE3-12, was included in the analysis. While all of these strains have significant sequence identity to one another in the 16S rDNA, several unique rDNA RiboPrint™ patterns were obtained. As shown in FIG. 4, the patterns of EcoRI restriction fragments which hybridized to 16S and 23S rDNA probes were different for *Arcobacter* sp. representative strains 97AE3-12 (ATCC #PTA-11409), 97AE3-3 (ATCC #PTA-11410), and 97AE3-1. This analysis showed that the genomic sequences surrounding the 16S and 23 rRNA genes in these strains are different from one another and also are different from the tested comparator strain *Arcobacter halophilus.*

Example 4

Screening of Bacterial Isolate 97AE3-12 for Growth in the Presence of Oil Under Low and High Salt Conditions Cultures of strain 97AE3-12 were grown anaerobically in the presence of oil using both a low salt minimal salts medium and a high salt synthetic brine formulation. The high salt synthetic brine used had a salinity of 64 ppt, which is about two times the salinity of sea water: The high salt synthetic brine was composed of the following: NaCl, 55.0 g/L, $NH_4Cl$, 0.1 g/L, $KH_2PO_4$, 0.05 g/L, $Na_2SO_4$, 0.1 g/L, selenite-tungstate solution [NaOH, 0.5 g/L, $Na_2SeO_3.5H_2O$, 6.0 mg/L, $Na_2WO_4.2H_2O$, 8.0 mg/L], 1 mL/L, $NaHCO_3$, 0.2 g/L, vitamin solution [Vitamin B12, 100 mg/L, p-aminobenzoic acid, 80 mg/L, D(+)-Biotin, 20 mg/L, Nicotinic acid, 200 mg/L, Calcium pantothenate, 100 mg/L, Pyridoxine hydrochloride, 300 mg/L, Thiamine-HCl.$2H_2O$, 200 mg/L, Alpha-lipoic acid, 50 mg/L], 1 mL/L, SL-10 trace metal solution [25% HCl, 10 mL/L, $FeCl_2.4H_2O$, 1.50 g/L, $ZnCl_2$, 70 mg/L, $MnCl_2.4H_2O$, 100 mg/L, $H_3BO_3$, 6 mg/L, $CoCl_2.6H_2O$, 190 mg/L, $CuCl_2.2H_2O$, 2 mg/L, $NiCl_2.6H_2O$, 24 mg/L, $Na_2MoO_4.2H_2O$, 36 mg/L], 1 mL/L, $CaCl_2.2\ H_2O$, 8.8 g/L, $NaNO_3$, 2.0 g/L, KCl, 0.86 g/L, $MgCl_2.6\ H_2O$, 6.4 g/L, and supplemented with $NaNO_3$, 2.0 g/L, pH 6.7 and 64 ppt salinity.

The low salt medium was composed of NaCl, 10 g/L, $NH_4Cl$, 1.0 g/L, $KH_2PO_4$, 0.5 g/L, $KSO_4$, 0.1 g/L, selenite-tungstate solution [NaOH, 0.5 g/L, $Na_2SeO_3.5\ H_2O$, 6.0 mg/L, $Na_2WO_4.2H_2O$, 8.0 mg/L], 1 mL/L, $NaHCO_3$, 2.5 g/L, vitamin solution [Vitamin B12, 100 mg/L, p-aminobenzoic acid, 80 mg/L, D(+)-Biotin, 20 mg/L, Nicotinic acid, 200 mg/L, Calcium pantothenate, 100 mg/L, Pyridoxine hydrochloride, 300 mg/L, Thiamine-HCl.$2H_2O$, 200 mg/L, Alpha-lipoic acid, 50 mg/L], 1 mL/L, SL-10 trace metal solution [25% HCl, 10 mL/L, $FeCl_2.4\ H_2O$, 1.50 g/L, $ZnCl_2$, 70 mg/L, $MnCl_2.4\ H_2O$, 100 mg/L, $H_3BO_3$, 6 mg/L, $CoCl_2.6\ H_2O$, 190 mg/L, $CuCl_2.2\ H_2O$, 2 mg/L, $NiCl_2.6\ H_2O$, 24 mg/L, $Na_2MoO_4.2\ H_2O$, 36 mg/L], 1 mL/L, $CaCl_2.2\ H_2O$, 0.1 g/L, $MgCl_2.6\ H_2O$, 0.2 g/L, yeast extract, 0.5 g/L, and $NaNO_3$, 2.0 g/L, pH 6.9 and 15 ppt salinity.

Both low and high salt media were tested for their ability to support growth of *Arcobacter* sp. 97AE3-12 with and without sodium lactate added as a carbon source at about 1 g/L (sodium lactate 60% syrup, 1.3 ml/L). Sodium nitrate was added at 2 g/L in media as the electron acceptor for all test samples. Media was degassed and 12 mL added to 20 mL serum vials. 6.0 mL of degassed autoclaved petroleum oil from Well #2 in the Wainwright field in the province of Alberta, Canada was added to each vial. This oil was the sole carbon source in the samples lacking lactate. 0.45 ml of 97AE3-12 grown in an undefined medium (Sea salts (Sigma S9883), 60.0 g/L, Peptone 5.0 g/L, Yeast Extract 5.0 g/L Casamino Acids 5.0 g/L, NaFeEDTA 133 mg/L, with pH adjusted to between 6.4-6.6 and filter sterilized) was added as inoculum to the anaerobic test cultures to about $5\times10^7$ cells of inoculum per ml of medium. Test cultures which contained 97AE3-12 inoculum were prepared in duplicate. A single non-inoculated control (NIC) per test medium was prepared as an abiotic control. Nitrate reduction was analyzed as a measurement of cell growth in each medium by IC as described in General Methods. 97AE3-12 reduced 100% of the nitrate provided to nitrite within 6 days of incubation at 25° C. in low salt medium supplemented with lactate, and reduced 50-77% of the nitrate to nitrogen in the high salt medium supplemented with lactate. Results in Table 7 show that *Arcobacter* sp. strain 97AE3-12 was able to grow using lactate as a carbon source in the presence of petroleum from the Wainwright Well, in both a low and a high salts medium.

TABLE 7

Nitrate reduction in cultures of 97AE3-12 in the presence of oil, in low or high salt media

| | % Nitrate Reduction | | | | |
|---|---|---|---|---|---|
| Day: | 1 | 2 | 6 | 17 | 29 |
| Test1: low salt plus lactate | 32.7% | 75.0% | 100.0% | 100.0% | 98.1% |
| NIC low salt- plus lactate | 23.6% | −4.2% | −3.9% | 0.0% | −1.6% |
| Test2: low salt no lactate | 12.1% | 6.3% | 11.5% | 0.0% | 22.9% |
| NIC-low salt no lactate | 14.0% | −2.2% | −1.4% | 0.0% | 9.6% |
| Test3: high salt plus lactate | 11.2% | 32.4% | 77.0% | 50.3% | 62.2% |
| NIC-high salt plus lactate | 11.6% | −1.7% | −0.8% | 0.0% | 13.9% |
| Test4: high salt no lactate | 11.7% | 6.1% | −15.6% | 0.0% | 27.8% |
| NIC-high salt no lactate | 16.4% | 10.8% | −21.8% | 0.0% | 30.9% |

Example 5

Screening Bacterial Isolates for their Ability to Form Biofilms and Plug Flow

*Arcobacter* strains 97AE 3-12, 97AE3-1, 97AE 3-3, 97AE 4-6, 97AE 4-5, 97AE 3-7, and 97AE4-1, that were isolated from a Canadian oil reservoir as described in Example 1 above, were tested for their ability form biofilms to inhibit flow in medium porosity (median pore diameter=10 microns) sintered glass filters as described in General Methods. The high salt medium used for testing had the following composition: NaCl, 54 g/L, $NH_4Cl$, 0.1 g/L, $KH_2PO_4$, 0.05 g/L, $Na_2SO_4$, 0.1 g/L, selenite-tungstate solution [NaOH, 0.5 g/L, $Na_2SeO_3.5\ H_2O$, 6.0 mg/L, $Na_2WO_4.2\ H_2O$, 8.0 mg/L], 1 mL/L, $NaHCO_3$, 0.2 g/L, vitamin solution [Vitamin B12, 100 mg/L, p-Aminobenzoic acid, 80 mg/L, D(+)-Biotin, 20 mg/L, Nicotinic acid, 200 mg/L, Calcium pantothenate, 100 mg/L, Pyridoxine hydrochloride, 300 mg/L, Thiamine-HCl.2$H_2O$, 200 mg/L, Alpha-lipoic acid, 50 mg/L], 1 mL/L, SL-10 trace metal solution [25% HCl, 10 mL/L, $FeCl_2$.4 $H_2O$, 1.50 g/L, $ZnCl_2$, 70 mg/L, $MnCl_2$.4 $H_2O$, 100 mg/L, $H_3BO_3$, 6 mg/L, $CoCl_2$.6 $H_2O$, 190 mg/L, $CuCl_2$.2 $H_2O$, 2 mg/L, $NiCl_2$.6 $H_2O$, 24 mg/L, $Na_2MoO_4$.2 $H_2O$, 36 mg/L], 1 mL/L, $CaCl_2$.2 $H_2O$, 8.8 g/L, KCl, 0.86 g/L, $MgCl_2$.6 $H_2O$, 6.4 g/L, disodium fumarate, 3275 g/L, sodium lactate, 1 g/L. This medium has salinity of 75 ppt.

Each *Arcobacter* strain was inoculated into medium of the above composition and incubated aerobically for 48 h. To initiate the test run 1 mL of a 48 h culture was added to 25 mL of the same medium in triplicate. Triplicate filter assemblies containing the inoculated medium were individually sealed in 125 mL incubation vessels under anaerobic conditions and placed in an incubator/shaker at 28° C. at 100 rpm for 2 weeks. In addition triplicate, uninoculated controls with the same medium formulation, but without the strain inoculum were run in parallel with the inoculated test samples.

After two weeks, flow rates were checked by passing 1 mL of deionized water, gravity driven, through the filters. Time for water passage was measured three times in succession for each of the test and control filters. Flow rates were calculated and post incubation values were compared to preincubation values for each filter. Results in Table 8 show that all strains tested caused a significant decrease in flow rate versus the controls, which had an average of 27% increase in flow rate. The increased flow rate resulted from better water saturation of the frit pores after two weeks of submersed incubation. These results demonstrate the capability of the isolated *Arcobacter* strains to form biofilms and plug pores in sand.

TABLE 8

Changes in flow rate through medium porosity glass filters after two week incubation with *Arcobacter* isolates

| | flow, ml/sec | | | | | | |
|---|---|---|---|---|---|---|---|
| | pre incubation | post incubation values* | | | | % change in | Mean % change in flow |
| treatment | value | #1 | #2 | #3 | mean | flow rate[1] | rate |
| control 1 | 0.077 | 0.091 | 0.100 | 0.100 | 0.097 | +26 | +27 |
| control 2 | 0.083 | 0.100 | 0.100 | 0.100 | 0.100 | +21 | |
| control 3 | 0.083 | 0.111 | 0.111 | 0.111 | 0.111 | +34 | |
| 97AE 3-12 | 0.067 | 0.029 | 0.029 | 0.031 | 0.029 | −57 | −56 |
| Replicate | 0.063 | 0.026 | 0.029 | 0.029 | 0.028 | −56 | |
| Replicate | 0.063 | 0.028 | 0.029 | 0.031 | 0.029 | −54 | |
| 97AE 3-3 | 0.111 | 0.083 | 0.083 | 0.083 | 0.083 | −25 | −48 |
| Replicate | 0.111 | 0.040 | 0.043 | 0.045 | 0.043 | −61 | |
| Replicate | 0.143 | 0.056 | 0.059 | 0.059 | 0.058 | −59 | |
| 97AE 4-6 | 0.143 | 0.071 | 0.077 | 0.071 | 0.073 | −49 | −52 |
| Replicate | 0.071 | 0.031 | 0.033 | 0.036 | 0.033 | −54 | |
| Replicate | 0.053 | 0.024 | 0.026 | 0.027 | 0.025 | −53 | |
| 97AE 4-5 | 0.100 | 0.037 | 0.042 | 0.042 | 0.040 | −60 | −61 |
| Replicate | 0.125 | 0.042 | 0.045 | 0.048 | 0.045 | −64 | |
| Replicate | 0.063 | 0.025 | 0.027 | 0.026 | 0.026 | −59 | |
| 97AE 3-7 | 0.067 | 0.027 | 0.029 | 0.031 | 0.029 | −57 | −57 |
| Replicate | 0.091 | 0.033 | 0.038 | 0.038 | 0.037 | −59 | |
| Replicate | 0.050 | 0.022 | 0.022 | 0.023 | 0.022 | −56 | |
| 97AE 4-1 | 0.091 | 0.059 | 0.059 | 0.067 | 0.061 | −33 | −50 |
| Replicate | 0.111 | 0.037 | 0.038 | 0.040 | 0.038 | −66 | |
| Replicate | | | | | | | |

*3 successive measurements/replicate.

[1]calculated as ((mean post incubation, mL/sec/preincubation, mL/sec) − 1) × 100

Example 6

97AE3-12 *Arcobacter* Strain Biofilm Assay in Low and High Salt Media with Lactate as Carbon Source Strain 97AE3-12 was assayed for the ability to form biofilms on sintered glass filters as described in General Methods using three different media ranging in salinity from 15 ppt to 68 ppt. Salinity of each media was measured by refractometer. 97AE3-12 was grown anaerobically in growth media of the following compositions:

Medium 1: minimal salts medium; NaCl, 10 g/L, $NH_4Cl$, 1.0 g/L, $KH_2PO_4$, 0.5 g/L, $KSO_4$, 0.1 g/L, selenite-tungstate solution [NaOH, 0.5 g/L, $Na_2SeO_3$.5 $H_2O$, 6.0 mg/L, $Na_2WO_4$.2$H_2O$, 8.0 mg/L], 1 mL/L, $NaHCO_3$, 2.5 g/L, vitamin solution [Vitamin B12, 100 mg/L, p-aminobenzoic acid, 80 mg/L, D(+)-Biotin, 20 mg/L, Nicotinic acid, 200 mg/L, Calcium pantothenate, 100 mg/L, Pyridoxine hydrochloride, 300 mg/L, Thiamine-HCl.2$H_2O$, 200 mg/L, Alpha-lipoic acid, 50 mg/L], 1 mL/L, SL-10 trace metal solution [25% HCl, 10 mL/L, $FeCl_2$.4 $H_2O$, 1.50 g/L, $ZnCl_2$, 70 mg/L, $MnCl_2$.4 $H_2O$, 100 mg/L, $H_3BO_3$, 6 mg/L, $CoCl_2$.6 $H_2O$, 190 mg/L, $CuCl_2$.2 $H_2O$, 2 mg/L, $NiCl_2$.6 $H_2O$, 24 mg/L, $Na_2MoO_4$.2 $H_2O$, 36 mg/L], 1 mL/L, $CaCl_2$.2$H_2O$, 0.1 g/L, $MgCl_2$.6$H_2O$, 0.2 g/L, yeast extract, 0.025 g/L, $NaNO_3$, 2.0 g/L, sodium lactate 60% syrup, 1.3 ml/L, Bromothymol blue solution, 0.4%, 3 mL. The salinity of this medium is 15 ppt.

Medium 2 equals Medium 1 in composition but with NaCl increased to 30 g/L. The salinity of this medium is 35 ppt.

Medium 3 is a high salts medium which includes higher levels of NaCl and the cations Ca++ and Mg++: NaCl, 51.5 g/L, $NH_4Cl$, 0.1 g/L, $KH_2PO_4$, 0.05 g/L, $Na_2SO_4$, 0.1 g/L, selenite-tungstate solution [NaOH, 0.5 g/L, $Na_2SeO_3$.5 $H_2O$, 6.0 mg/L, $Na_2WO_4$.2 $H_2O$, 8.0 mg/L], 1 mL/L, $NaHCO_3$, 0.2 g/L, vitamin solution [Vitamin B12, 100 mg/L, p-aminobenzoic acid, 80 mg/L, D(+)-Biotin, 20 mg/L, Nicotinic acid, 200 mg/L, Calcium pantothenate, 100 mg/L, Pyridoxine hydrochloride, 300 mg/L, Thiamine-HCl.2$H_2O$, 200 mg/L, Alpha-lipoic acid, 50 mg/L], 1 mL/L, SL-10 trace metal solution [25% HCl, 10 mL/L, $FeCl_2$.4 $H_2O$, 1.50 g/L, $ZnCl_2$, 70 mg/L, $MnCl_2$.4 $H_2O$, 100 mg/L, $H_3BO_3$, 6 mg/L, $CoCl_2$.6 $H_2O$, 190 mg/L, $CuCl_2$.2 $H_2O$, 2 mg/L, $NiCl_2$.6 $H_2O$, 24 mg/L, $Na_2MoO_4$.2 $H_2O$, 36 mg/L], 1 mL/L, $CaCl_2$.2 $H_2O$, 8.8 g/L, yeast extract, 0.025 g/L, $NaNO_3$, 2.0 g/L, sodium lactate 60% syrup, 1.3 ml/L, KCl, 0.86 g/L, $MgCl_2$.6 $H_2O$, 6.4 g/L, Bromothymol blue solution, 0.4%, 1 mL. The salinity of this medium is 68 ppt.

The experiment and flow rate tests after 2 weeks of incubation were performed as described in General Methods. Medium inoculated with *Arcobacter* sp. 97AE3-12 were prepared in triplicate; non inoculated controls were prepared in duplicate. While the flow rate increased in the controls as in Example 5, strain 97AE3-12 caused a significant decrease in flow rate (Table 9). The flow rates in the control treatments increased by an average of 54, 35 and 46% for Medium 1, 2 and 3, respectively. The test treatments containing the 97AE3-12 inoculum showed a mean decline of 80, 80 and 46% in flow rate for medium 1, 2 and 3, respectively which had salinities of 15, 35 and 68 ppt, respectively.

TABLE 9

Changes in flow rate through medium porosity glass filters after two weeks incubation.

| | pre-incubation Mean flow rate, ml/sec | post incubation flow rate, ml/sec 1 | flow rate, ml/sec 2 | flow rate, ml/sec 3 | Mean flow rate, ml/sec | % change in flow rate[1] | % change in mean flow rate |
|---|---|---|---|---|---|---|---|
| test1 15 ppt | 0.111 | 0.017 | 0.018 | 0.017 | 0.017 | −84 | −80 |
| test2 15 ppt | 0.100 | 0.020 | 0.020 | 0.020 | 0.020 | −80 | |
| test3 15 ppt | 0.091 | 0.022 | 0.022 | 0.022 | 0.022 | −76 | |
| control1 15 ppt | 0.143 | 0.200 | 0.200 | 0.167 | 0.189 | 32 | 54 |
| control2 15 ppt | 0.143 | 0.250 | 0.250 | 0.250 | 0.250 | 75 | |
| test1 35 ppt | 0.143 | 0.030 | 0.031 | 0.031 | 0.031 | −78 | −80 |
| test2 35 ppt | 0.143 | 0.027 | 0.024 | 0.024 | 0.025 | −82 | |
| test3 35 ppt | 0.125 | 0.026 | 0.027 | 0.028 | 0.027 | −78 | |
| control1 35 ppt | 0.100 | 0.125 | 0.111 | 0.125 | 0.120 | 20 | 35 |
| control2 35 ppt | 0.111 | 0.167 | 0.167 | 0.167 | 0.167 | 50 | |
| test1 68 ppt | 0.091 | 0.067 | 0.071 | 0.077 | 0.072 | −21 | −46 |
| test1 68 ppt | 0.125 | 0.056 | 0.056 | 0.059 | 0.057 | −55 | |
| test1 68 ppt | 0.111 | 0.043 | 0.043 | 0.038 | 0.042 | −62 | |
| control1 68 ppt | 0.111 | 0.200 | 0.200 | 0.200 | 0.200 | 80 | 46 |
| control2 68 ppt | 0.111 | 0.125 | 0.125 | 0.125 | 0.125 | 13 | |

*3 successive measurements

[1]calculated as ((mean post incubation, mL/sec/preincubation, mL/sec) − 1) × 100

Example 7

Aggregation of Silica Particles

*Arcobacter* strain 97AE3-12 was tested for its ability to aggregate grains of crystalline silica as described in General Methods. The medium used for testing had the following composition: NaCl, 54 g/L, $NH_4Cl$, 0.1 g/L, $KH_2PO_4$, 0.05 g/L, $Na_2SO_4$, 0.1 g/L, selenite-tungstate solution [NaOH, 0.5 g/L, $Na_2SeO_3.5H_2O$, 6.0 mg/L, $Na_2WO_4.2H_2O$, 8.0 mg/L], 0.5 mL/L, $NaHCO_3$, 0.1 g/L, vitamin solution [Vitamin B12, 100 mg/L, p-Aminobenzoic acid, 80 mg/L, D(+)-Biotin, 20.00 mg/L, Nicotinic acid, 200 mg/L, Calcium pantothenate, 100 mg/L, Pyridoxine hydrochloride, 300 mg/L, Thiamine-HCl.$2H_2O$, 200 mg/L, Alpha-lipoic acid, 50 mg/L], 1.0 mL/L, SL-10 trace metal solution [25% HCl, 10 mL/L, $FeCl_2.4H_2O$, 1.50 g/L, $ZnCl_2$, 70 mg/L, $MnCl_2.4H_2O$, 100 mg/L, $H_3BO_3$, 6 mg/L, $CoCl_2.6H_2O$, 190 mg/L, $CuCl_2.2H_2O$, 2 mg/L, $NiCl_2.6H_2O$, 24 mg/L, $Na_2MoO_4.2H_2O$, 36 mg/L], 1.0 mL/L, $CaCl_2.2H_2O$, 4.4 g/L, 0.25 g yeast extract, 0.5 g casein peptone, KCl, 0.86 g/L, $MgCl_2.6H_2O$, 6.4 g/L, and sodium citrate, 1 g/L. Separate media had as the electron acceptor either $NaNO_3$, 2 g/L or NaFumarate 3.7 g/mL. The salinity is 64 ppt.

Duplicate samples of each medium were inoculated with 200 μL of an aerobic culture of strain 97AE3-12. Duplicate control tubes were not inoculated. Tubes were statically incubated for 7 days at 30° C. After seven days the mean OD600 of the duplicate, inoculated tubes and duplicate uninoculated control tubes was about 0.04. When treatment tubes were mixed vigorously by 10 seconds of vortexing, turbidity increased dramatically due to resuspension of the crystalline silica, which had settled to the tube bottoms. The decline in turbidity due to settling of the crystalline silica was monitored over time after mixing by measuring OD600. Results in Table 10 showed that turbidity declined much more rapidly in the inoculated treatments than in the controls as indicated by the percent reduction in OD600 for the inoculated culture vs the control at 1 min and 10 min after mixing.

This resulted from the silica particles forming large clumps, up to 100 microns in diameter as determined by microscopic examination, in the inoculated treatments, which settled rapidly compared to the dispersed, unaggregated, 2-20μ particles in the uninoculated control tubes. The contrasting behavior of the silica particles showed that strain 97AE3-12 formed a strong adhesive interaction with adjacent crystalline silica particles causing clumping of the particles. Aggregation occurred for strain 97AE3-12 cultures in both nitrate and fumarate media, though more aggregation occurred with nitrate as the electron acceptor.

TABLE 10

Settling of silica particles due to microbial induced particle aggregation.

| Electron Donor and Acceptor | Optical density (OD), 600 nm Treatment | Optical density (OD), 600 nm, before mixing | Optical density (OD), 600 nm, 1 minute after mixing | Optical density (OD), 600 nm, 10 minutes after mixing |
|---|---|---|---|---|
| 1000 ppm | uninoculated control, #1 | −0.0013 | 0.4597 | 0.4430 |
| Citrate | uninoculated control, #2 | 0.0013 | 0.4794 | 0.4699 |
| 2000 ppm | Mean | 0 | 0.4696 | 0.4565 |
| $NaNO_3$ | inoculated test #1 | 0.0852 | 0.1738 | 0.1527 |
| | inoculated test #2 | 0.0826 | 0.1393 | 0.112 |
| | Mean | 0.0839 | 0.1566 | 0.1324 |
| | % reduction in OD | Not applicable | 66.7% | 71.0% |

TABLE 10-continued

Settling of silica particles due to microbial induced particle aggregation.

| Electron Donor and Acceptor | Optical density (OD), 600 nm Treatment | Optical density (OD), 600 nm, before mixing | Optical density (OD), 600 nm, 1 minute after mixing | Optical density (OD), 600 nm, 10 minutes after mixing |
|---|---|---|---|---|
| 1000 ppm | uninoculated control, #1 | 0.011 | 0.444 | 0.339 |
| Citrate | uninoculated control, #2 | 0.011 | 0.486 | 0.360 |
| 3500 ppm | Mean | 0.011 | 0.465 | 0.350 |
| NaFumarate | inoculated test #1 | 0.018 | 0.265 | 0.217 |
| | inoculated test #2 | 0.025 | 0.272 | 0.213 |
| | Mean | 0.021 | 0.268 | 0.215 |
| | % reduction in OD | Not applicable | 42.3% | 38.6% |

Example 8

Control Slim Tube Pressure Drop Measurements

The slim tube set-up described in General Methods was used to measure pressure changes of a control sand sample over time. Brine #1 that had been filter sterilized was fed continuously 8 days to slim tube 9*a* while the pressure drop across the slim tube was measured (day 4 through day 12 in FIG. 7). The pressure drop remained about 3 psi (0.0207 mega Pascal). This illustrates the stability of the packed sand in the slim tube while being flooded with the filtered injection brine, as no change in the pressure drop across the slim tube was observed experimentally. This is contrast to the treated slim tubes described below in Examples 9 and 10 that showed marked changes in pressure drop as a result of the microbial treatment.

Example 9

Inoculated, Batch Fed Slim Tube Pressure Drop Measurements

Slim tube 9*a* of Example 8 was pre-inoculated with 60 ml of live injection water (Brine #1 which was not filter sterilized) at a rate of 15 ml/hour for 4 hours. Following this pre-inoculation, an effluent sample was collected from slim tube 9*a* and cell counts were measured and are shown in Table 11 (Cell Count 1: 9*a*).

One day after pre-inoculation with unfiltered live injection water (Brine #1), the slim tube was inoculated with strain 97AE3-12 (ATCC NO: PTA-11409). A 1:1 dilution of a growing culture of strain 97AE3-12 with unfiltered live injection water was grown in Brine #5 and incubated at room temperature for 48 hours with agitation, and then diluted 1:30 in Brine #5 to inoculate slim tube 9*a*. Cell counts of this inoculum were determined and are shown in Table 11 (Cell Count 2: 9*a*). A 50 ml volume of this inoculum was pumped into the slim tube at a rate of about 0.25 ml/min. The process of slim tube inoculation took about 4 h to complete. Following inoculation the slim tube was shut in for 6 days. An effluent sample was taken after the 6 day shut in period and cell counts were measured and are shown in Table 11 (Cell Count 3: 9*a*).

Starting on day 20, upon completion of the aging period, Brine #2 was fed to slim tube 9*a* in 4 to 8 hr pulses at a rate of 3.6 ml/hour twice a week (once every 3 or 4 days) for about 25 days (ending on day 45, FIG. 8). The pressure drop was measured across slim tube 9*a* throughout the regiment of pulse feeding. Four hr pulses were fed on days, 20, and 24. Eight hr pulses were fed on days 27, 32, 34, 41, and 44. Between each of these nutrient pulses Brine #1 was fed at a rate of 3.6 ml/hr. The pressure drop was initially about 3 psi (0.0207 mega Pascal). Ten days after initiating pulse feeding on slim tube 9*a* there was a discernable increase in pressure drop that became more pronounced with time (FIG. 8). At the end of the experiment on day 45 the pressure drop was nearly 3 times the control (Example 8). At this point in time an effluent sample was taken and cell counts were measure and are shown in Table 11 (Cell Count 4: 9*a*). This substantial increase in pressure demonstrates the potential for *Arcobacter* sp. 97AE3-12 (ATCC NO: PTA-11409) to effectively modify the permeability of porous rock when it is fed batch wise with nutrients.

Example 10

Continuously-Fed Core Sand Slim Tube and Pressure Drop Measurements

Slim tube 9*b* (General Methods) was pre-inoculated with live injection water from the test well site (unfiltered Brine #1), sampled for cell counts in the effluent of the slim tube (Table 11, Cell count 1: 9*b*), and inoculated with strain 97AE3-12 as in Example 9, except that *Arcobacter* sp. strain 97AE3-12 was not diluted 1:1 with unfiltered injection Brine #1. The cell count was measured in this inoculum and is shown in Table 11 (Cell Count 2: 9*b*). Following inoculation with *Arcobacter* sp. strain 97AE3-12 the slim tube 9*b* was aged for 6 days as above. An effluent sample was taken and cell counts were measured after inoculation and are shown in Table 11 (Cell Count 3: 9*b*). Brine #2 nutrient feed was continuously fed to slim tube 9*b* at a rate of 3.6 ml/hour for the duration of the experiment while the pressure drop across it was measured (FIG. 9). Initially the pressure drop was about 2 psi (0.0137 mega Pascal) as shown in FIG. 9 (see day 20). By day 32, the observed pressure drop for slim tube 9*b* had increased by about a factor of 2 to 3 compared to the initial pressure drop at day 20. At day 32.8, feeding of Brine #2 was stopped due to a pump failure. In order to restart the pump, it had to be primed at a high flow rate. This pump priming operation appeared to reduce the pressure drop as seen after day 32.8 in FIG. 9. However, after day 33, nutrient feed Brine #3 was fed again at a rate of 3.6 ml/hour and the pressure drop climbed again so that it was about a factor of 2 higher at the end of the experiment at day 45 as compared to the initial pressure drop at day 20. At this point in time an effluent sample was taken and cell counts were measure and are shown in Table 11 (Cell Count 4: 9*b*). This substantial increase in pressure demonstrates the potential for *Arcobacter* sp. 97AE3-12 (ATCC NO: PTA-11409) to effectively modify the permeability of porous rock when fed continuously with nutrients.

TABLE 11

Cell counts in different slim tube experiment samples

| Analysis | Slim tube 9a | Slim tube 9b |
|---|---|---|
| Cell count 1: effluent of slim tube following pre-inoculation with live brine | $2.3 \times 10^4$ CFU/ml | $2.3 \times 10^5$ CFU/ml |
| Cell count 2 of the *Arcobacter* inoculum | $1.1 \times 10^6$ CFU/ml | $1.7 \times 10^5$ CFU/ml |
| Cell count 3 in slim tube effluent after 6 day aging with *Arcobacter* inoculum | $5.2 \times 10^6$ CFU/ml | $7.6 \times 10^5$ CFU/ml |
| Cell count 4: MPNs in effluent | $1.2 \times 10^7$ CFU/ml | $3.1 \times 10^5$ CFU/ml |

What is claimed is:

1. A composition for producing a plugging biofilm useful for enhancing oil recovery comprising:

a) at least one isolated strain of *Arcobacter* comprising a partial 16S rDNA sequence selected from the group consisting of SEQ ID NOs; 1, 33, 34, 35, 36, 37, and 38;

b) one or more electron acceptors, wherein the electron acceptor is one or more ionic salts of nitrate, one or more ionic salts of nitrite or any combination of ionic salts of nitrate or nitrite; and c) at least one carbon source selected from the group consisting of lactate, acetate, formate and succinate;

wherein the population of *Arcobacter* is enhanced under denitrifying conditions using the one or more electron acceptors of (b) and the at least one carbon source of (c) and wherein the plugging biofilm is produced by the isolated strain of *Arcobacter*.

2. The composition of claim 1 wherein the strain of *Arcobacter* is selected from the group consisting of 97AE3-3 (ATCC No. PTA-11410) and 97AE3-12 (ATCC No. PTA-11409).

3. The composition of claim 1, further comprising one or more additional microorganisms.

4. The composition of claim 3, wherein said one or more additional microorganisms grows in the presence of oil under denitrifying conditions.

5. The composition of claim 4, wherein said one or more additional microorganisms comprises a *Shewanella* species or *Thauera* sp. AL9:8 (ATCC # PTA-949).

6. The composition of claim 5 wherein the *Shewanella* species comprises a 16S rDNA comprising the degenerate signature sequences of SEQ ID NOs: 48, 50 and 52.

* * * * *